US011929160B2

(12) United States Patent
Edwards et al.

(10) Patent No.: US 11,929,160 B2
(45) Date of Patent: Mar. 12, 2024

(54) MEDICAMENT DELIVERY DEVICES WITH WIRELESS CONNECTIVITY AND COMPLIANCE DETECTION

(71) Applicant: KALEO, INC., Richmond, VA (US)

(72) Inventors: Eric S. Edwards, Moseley, VA (US); Evan T. Edwards, Charlottesville, VA (US); Paul F. Meyers, Fishers, IN (US); Michael J. Roe, Powhatan, VA (US)

(73) Assignee: kaleo, Inc., Richmond, VA (US)

( * ) Notice: Subject to any disclaimer, the term of this patent is extended or adjusted under 35 U.S.C. 154(b) by 569 days.

(21) Appl. No.: 17/260,423

(22) PCT Filed: Jul. 15, 2019

(86) PCT No.: PCT/US2019/041823
§ 371 (c)(1),
(2) Date: Jan. 14, 2021

(87) PCT Pub. No.: WO2020/018433
PCT Pub. Date: Jan. 23, 2020

(65) Prior Publication Data
US 2021/0257075 A1    Aug. 19, 2021

Related U.S. Application Data

(60) Provisional application No. 62/698,863, filed on Jul. 16, 2018.

(51) Int. Cl.
*G16H 20/17* (2018.01)
*A61M 5/142* (2006.01)
(Continued)

(52) U.S. Cl.
CPC ........ *G16H 20/17* (2018.01); *A61M 5/14248* (2013.01); *A61M 5/1723* (2013.01);
(Continued)

(58) Field of Classification Search
CPC ....... G16H 20/17; G16H 40/67; H04W 4/026; H04W 4/027; H04W 4/029; H04W 4/35; H04W 4/80
See application file for complete search history.

(56) References Cited

U.S. PATENT DOCUMENTS 2,960,087 A    11/1960   Uytenbogaart
3,055,362 A     9/1962   Uytenbogaart
(Continued)

FOREIGN PATENT DOCUMENTS

AU    2004231230      6/2006
EP    1287840 A1      3/2003
(Continued)

OTHER PUBLICATIONS

"Allerject Canada's first "talking"epinephrine auto-injector" by Sanofi Canada. Posting date: Jan. 25, 2013. Retrieval date Oct. 18, 2022. Retrieved from the internet: https://www.newswire.ca/news-releases/allerject-canadas-first-talking-epinephrine-auto-injector-511884451.html (Year: 2013).
(Continued)

*Primary Examiner* — Omer S Khan
(74) *Attorney, Agent, or Firm* — Ambrose, Mills & Lazarow, PLLC

(57) ABSTRACT

A computer-implemented method includes receiving a signal associated with a characteristic of an actuation event of a medicament delivery device. The method includes establishing a communications link (e.g., via a short-range wireless protocol), between a mobile computing device and a medicament delivery device. A wireless first signal associated with a first motion profile of the medicament delivery device is then received from the medicament delivery device. A second signal associated with a second motion profile of the mobile computing device is generated. The method then includes producing a notification via the mobile
(Continued)

computing device when A) a magnitude of the first motion profile is outside of a first threshold and B) a magnitude of the second motion profile is outside of a second threshold.

10 Claims, 45 Drawing Sheets

(51) Int. Cl.
    *A61M 5/172*     (2006.01)
    *A61M 5/20*     (2006.01)
    *A61M 5/315*     (2006.01)
    *A61M 15/00*     (2006.01)
    *A61M 15/08*     (2006.01)
    *G16H 40/67*     (2018.01)

(52) U.S. Cl.
    CPC ...... *A61M 5/2053* (2013.01); *A61M 5/31533* (2013.01); *A61M 5/3157* (2013.01); *A61M 15/009* (2013.01); *A61M 15/08* (2013.01); *G16H 40/67* (2018.01); *A61M 2005/14288* (2013.01); *A61M 2205/3303* (2013.01); *A61M 2205/3553* (2013.01); *A61M 2205/505* (2013.01); *A61M 2205/52* (2013.01); *A61M 2205/8206* (2013.01)

(56) References Cited

U.S. PATENT DOCUMENTS

| | | |
|---|---|---|
| 3,115,133 A | 12/1963 | Morando |
| 3,426,448 A | 2/1969 | Sarnoff |
| 3,688,765 A | 9/1972 | Gasaway |
| 3,768,472 A | 10/1973 | Hodosh et al. |
| 3,795,061 A | 3/1974 | Sarnoff et al. |
| 3,945,379 A | 3/1976 | Pritz et al. |
| 4,108,177 A | 8/1978 | Pistor |
| 4,226,235 A | 10/1980 | Sarnoff et al. |
| 4,360,019 A | 11/1982 | Portner et al. |
| 4,424,057 A | 1/1984 | House |
| 4,441,629 A | 4/1984 | Mackal |
| 4,484,910 A | 11/1984 | Sarnoff |
| 4,524,243 A | 6/1985 | Shapiro |
| 4,573,976 A | 3/1986 | Sampson et al. |
| 4,596,556 A | 6/1986 | Morrow et al. |
| 4,610,666 A | 9/1986 | Pizzino |
| 4,613,328 A | 9/1986 | Boyd |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,853,521 A | 8/1989 | Claeys et al. |
| 4,865,582 A | 9/1989 | Sibalis |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,843 A | 3/1992 | Monroe et al. |
| 5,125,898 A | 6/1992 | Kaufhold, Jr. et al. |
| 5,167,625 A | 12/1992 | Jacobsen et al. |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,281,198 A | 1/1994 | Haber et al. |
| 5,286,258 A | 2/1994 | Haber et al. |
| 5,298,023 A | 3/1994 | Haber et al. |
| 5,312,326 A | 5/1994 | Myers et al. |
| 5,314,412 A | 5/1994 | Rex |
| 5,314,502 A | 5/1994 | McNichols et al. |
| 5,343,519 A | 8/1994 | Feldman |
| 5,344,407 A | 9/1994 | Ryan |
| 5,347,453 A | 9/1994 | Maestre |
| 5,354,284 A | 10/1994 | Haber et al. |
| 5,356,376 A | 10/1994 | Milijasevic et al. |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,394,866 A | 3/1995 | Ritson et al. |
| 5,399,163 A | 3/1995 | Peterson et al. |
| 5,405,362 A | 4/1995 | Kramer et al. |
| 5,417,660 A | 5/1995 | Martin |
| 5,466,217 A | 11/1995 | Myers et al. |
| 5,505,192 A | 4/1996 | Samiotes et al. |
| 5,514,135 A | 5/1996 | Earle |
| 5,544,647 A | 8/1996 | Jewett et al. |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,610,992 A | 3/1997 | Hickman |
| 5,615,771 A | 4/1997 | Hollister |
| 5,616,132 A | 4/1997 | Newman |
| 5,642,731 A | 7/1997 | Kehr |
| 5,645,534 A | 7/1997 | Chanoch |
| 5,662,612 A | 9/1997 | Niehoff |
| 5,681,291 A | 10/1997 | Galli |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |
| 5,728,074 A | 3/1998 | Castellano et al. |
| 5,740,794 A | 4/1998 | Smith et al. |
| 5,752,235 A | 5/1998 | Kehr et al. |
| 5,772,635 A | 6/1998 | Dastur et al. |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,397 A | 9/1998 | Goodman et al. |
| 5,814,020 A | 9/1998 | Gross |
| 5,823,346 A | 10/1998 | Weiner |
| 5,823,363 A | 10/1998 | Cassel |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,852,590 A | 12/1998 | de la Huerga |
| 5,853,292 A | 12/1998 | Eggert et al. |
| 5,868,713 A | 2/1999 | Klippenstein |
| 5,868,721 A | 2/1999 | Marinacci |
| D407,487 S | 3/1999 | Greubel et al. |
| 5,905,653 A | 5/1999 | Higham et al. |
| 5,925,021 A | 7/1999 | Castellano et al. |
| 5,928,195 A | 7/1999 | Malamud |
| 5,941,857 A | 8/1999 | Nguyen et al. |
| 5,954,641 A | 9/1999 | Kehr et al. |
| 5,964,739 A | 10/1999 | Champ |
| 5,970,457 A | 10/1999 | Brant et al. |
| 5,971,953 A | 10/1999 | Bachynsky |
| 5,991,655 A | 11/1999 | Gross et al. |

(56) References Cited

U.S. PATENT DOCUMENTS

| | | |
|---|---|---|
| 6,002,781 A | 12/1999 | Takayama et al. |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,144,310 A | 11/2000 | Morris |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,175,752 B1 | 1/2001 | Say |
| 6,179,812 B1 | 1/2001 | Botich et al. |
| 6,190,326 B1 | 2/2001 | McKinnon et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,249,717 B1 | 6/2001 | Nicholson et al. |
| 6,258,063 B1 | 7/2001 | Haar et al. |
| 6,259,654 B1 | 7/2001 | de la Huerga |
| 6,264,629 B1 | 7/2001 | Landau |
| 6,270,455 B1 | 8/2001 | Brown |
| 6,285,757 B1 | 9/2001 | Carroll et al. |
| 6,297,737 B1 | 10/2001 | Irvin |
| 6,312,412 B1 | 11/2001 | Saied et al. |
| 6,317,630 B1 | 11/2001 | Gross et al. |
| 6,321,070 B1 | 11/2001 | Clark et al. |
| 6,321,654 B1 | 11/2001 | Robinson |
| 6,323,780 B1 | 11/2001 | Morris |
| 6,334,070 B1 | 12/2001 | Nova et al. |
| 6,364,866 B1 | 4/2002 | Furr et al. |
| 6,371,939 B2 | 4/2002 | Bergens et al. |
| 6,377,848 B1 | 4/2002 | Garde et al. |
| 6,387,078 B1 | 5/2002 | Gillespie, III |
| 6,398,760 B1 | 6/2002 | Danby |
| 6,405,912 B2 | 6/2002 | Giannou |
| 6,411,567 B1 | 6/2002 | Niemiec et al. |
| 6,413,236 B1 | 7/2002 | Van Dyke |
| 6,425,897 B2 | 7/2002 | Overes et al. |
| 6,427,684 B2 | 8/2002 | Ritsche et al. |
| 6,428,517 B1 | 8/2002 | Hochman et al. |
| 6,428,528 B2 | 8/2002 | Sadowski |
| 6,475,181 B1 | 11/2002 | Potter et al. |
| 6,478,769 B1 | 11/2002 | Parker |
| 6,482,185 B1 | 11/2002 | Hartmann |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,539,281 B2 | 3/2003 | Wan et al. |
| 6,540,672 B1 | 4/2003 | Simonsen et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,560,471 B1 | 5/2003 | Heller |
| 6,565,509 B1 | 5/2003 | Say |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,589,229 B1 | 7/2003 | Connelly et al. |
| 6,595,956 B1 | 7/2003 | Gross et al. |
| 6,597,794 B2 | 7/2003 | Cole et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,648,850 B2 | 11/2003 | Landau |
| 6,659,980 B2 | 12/2003 | Moberg et al. |
| 6,676,630 B2 | 1/2004 | Landau et al. |
| 6,679,862 B2 | 1/2004 | Diaz et al. |
| 6,689,093 B2 | 2/2004 | Landau |
| 6,702,778 B2 | 3/2004 | Hill et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,784,798 B2 | 8/2004 | Morris |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,805,686 B1 | 10/2004 | Fathallah et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,923,764 B2 | 8/2005 | Aceti et al. |
| 6,936,029 B2 | 8/2005 | Mann et al. |
| 6,937,150 B2 | 8/2005 | Medema et al. |
| 6,942,646 B2 | 9/2005 | Langley et al. |
| 6,945,961 B2 | 9/2005 | Miller et al. |
| 6,946,299 B2 | 9/2005 | Neel et al. |
| 6,949,082 B2 | 9/2005 | Langley et al. |
| 6,950,028 B2 | 9/2005 | Zweig |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,029,455 B2 | 4/2006 | Flaherty et al. |
| 7,048,141 B2 | 5/2006 | Abdulhay |
| 7,072,738 B2 | 7/2006 | Bonney et al. |
| 7,074,211 B1 | 7/2006 | Heiniger et al. |
| 7,093,595 B2 | 8/2006 | Nesbitt |
| 7,102,526 B2 | 9/2006 | Zweig |
| 7,104,972 B2 | 9/2006 | Moller et al. |
| 7,113,101 B2 | 9/2006 | Peterson et al. |
| 7,116,233 B2 | 10/2006 | Zhurin |

(56) References Cited

U.S. PATENT DOCUMENTS

| | | |
|---|---|---|
| 7,118,553 B2 | 10/2006 | Scherer |
| 7,126,879 B2 | 10/2006 | Snyder |
| 7,158,011 B2 | 1/2007 | Brue |
| 7,191,916 B2 | 3/2007 | Clifford et al. |
| 7,229,458 B2 | 6/2007 | Boecker et al. |
| 7,278,983 B2 | 10/2007 | Ireland et al. |
| 7,299,981 B2 | 11/2007 | Hickle et al. |
| 7,343,914 B2 | 3/2008 | Abrams et al. |
| 7,351,223 B2 | 4/2008 | Call |
| 7,416,540 B2 | 8/2008 | Edwards et al. |
| 7,544,188 B2 | 6/2009 | Edwards et al. |
| 7,630,788 B1 | 12/2009 | Reese |
| 7,635,348 B2 | 12/2009 | Raven et al. |
| 7,648,482 B2 | 1/2010 | Edwards et al. |
| 7,648,483 B2 | 1/2010 | Edwards et al. |
| 7,657,849 B2 | 2/2010 | Chaudhri et al. |
| 7,670,328 B2 | 3/2010 | Miller et al. |
| 7,682,155 B2 | 3/2010 | Raven et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,871,393 B2 | 1/2011 | Monroe |
| 7,875,022 B2 | 1/2011 | Wenger et al. |
| 7,938,802 B2 | 5/2011 | Bicknell et al. |
| 7,947,017 B2 | 5/2011 | Edwards et al. |
| 8,021,344 B2 | 9/2011 | Edwards et al. |
| 8,123,719 B2 | 2/2012 | Edwards et al. |
| 8,149,111 B2 | 4/2012 | Monroe |
| 8,172,082 B2 | 5/2012 | Edwards et al. |
| 8,206,360 B2 | 6/2012 | Edwards et al. |
| 8,212,658 B2 | 7/2012 | Monroe |
| 8,226,610 B2 | 7/2012 | Edwards et al. |
| 8,229,392 B2 | 7/2012 | Bumiller et al. |
| 8,231,573 B2 | 7/2012 | Edwards et al. |
| 8,424,517 B2 | 4/2013 | Sutherland et al. |
| 8,544,645 B2 | 10/2013 | Edwards et al. |
| 8,556,865 B2 | 10/2013 | Krulevitch et al. |
| 8,556,867 B2 | 10/2013 | Krulevitch et al. |
| 8,627,816 B2 | 1/2014 | Edwards et al. |
| 8,639,288 B1 | 1/2014 | Friedman |
| 8,670,865 B2 | 3/2014 | Coe |
| 8,690,827 B2 | 4/2014 | Edwards et al. |
| 8,789,748 B2 | 6/2014 | Waugh et al. |
| 8,807,131 B1 | 8/2014 | Tunnell et al. |
| 8,849,449 B2 | 9/2014 | Waugh et al. |
| 8,910,299 B2 | 12/2014 | Michalske |
| 8,922,367 B2 | 12/2014 | Denny et al. |
| 8,926,594 B2 | 1/2015 | Edwards et al. |
| 8,939,943 B2 | 1/2015 | Edwards et al. |
| 9,022,980 B2 | 5/2015 | Edwards et al. |
| 9,035,765 B2 | 5/2015 | Engelhard et al. |
| 9,053,530 B2 | 6/2015 | Vik et al. |
| 9,084,849 B2 | 7/2015 | Edwards et al. |
| 9,173,999 B2 | 11/2015 | Edwards et al. |
| 9,179,260 B2 | 11/2015 | Ostrander et al. |
| 9,327,077 B2 | 5/2016 | Edwards et al. |
| 9,542,826 B2 | 1/2017 | Edwards et al. |
| 9,566,395 B2 | 2/2017 | Denny et al. |
| 9,643,770 B2 | 5/2017 | Denny et al. |
| 9,671,241 B2 | 6/2017 | Tang |
| 9,672,328 B2 | 6/2017 | Saint et al. |
| 9,838,858 B2 | 12/2017 | Anand et al. |
| 10,080,841 B2 | 9/2018 | Levine et al. |
| 10,839,669 B2 | 11/2020 | Edwards et al. |
| 2001/0005781 A1 | 6/2001 | Bergens et al. |
| 2002/0000225 A1 | 1/2002 | Schuler et al. |
| 2002/0016567 A1 | 2/2002 | Hochman et al. |
| 2002/0025267 A1 | 2/2002 | Lieber et al. |
| 2002/0042596 A1 | 4/2002 | Hartlaub et al. |
| 2002/0072784 A1 | 6/2002 | Sheppard, Jr. et al. |
| 2002/0074345 A1 | 6/2002 | Schneider et al. |
| 2002/0076679 A1 | 6/2002 | Aman |
| 2002/0090601 A1 | 7/2002 | Strupat et al. |
| 2002/0096543 A1 | 7/2002 | Juselius |
| 2002/0169439 A1 | 11/2002 | Flaherty |
| 2002/0183721 A1 | 12/2002 | Santini, Jr. et al. |
| 2003/0028145 A1 | 2/2003 | Duchon et al. |
| 2003/0040717 A1 | 2/2003 | Saulenas et al. |
| 2003/0060765 A1 | 3/2003 | Campbell et al. |
| 2003/0065536 A1 | 4/2003 | Hansen et al. |
| 2003/0106824 A1 | 6/2003 | Wilmot et al. |
| 2003/0120212 A1 | 6/2003 | Dedig et al. |
| 2003/0130853 A1 | 7/2003 | Maire |
| 2003/0132128 A1 | 7/2003 | Mazur |
| 2003/0135388 A1 | 7/2003 | Martucci et al. |
| 2003/0171717 A1 | 9/2003 | Farrugia et al. |
| 2003/0233070 A1 | 12/2003 | De La Serna et al. |
| 2004/0010207 A1 | 1/2004 | Flaherty et al. |
| 2004/0015125 A1 | 1/2004 | Alexandre et al. |
| 2004/0019326 A1 | 1/2004 | Gilbert et al. |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0042596 A1 | 3/2004 | Kim et al. |
| 2004/0054327 A1 | 3/2004 | Gillespie, III |
| 2004/0069667 A1 | 4/2004 | Tomellini et al. |
| 2004/0078001 A1 | 4/2004 | Langley et al. |
| 2004/0084047 A1 | 5/2004 | Hickle |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0147818 A1 | 7/2004 | Levy et al. |
| 2004/0159364 A1 | 8/2004 | Landau et al. |
| 2004/0210199 A1 | 10/2004 | Atterbury et al. |
| 2004/0215369 A1 | 10/2004 | Rosenblum |
| 2004/0220524 A1 | 11/2004 | Sadowski et al. |
| 2004/0225255 A1 | 11/2004 | Ono |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0055014 A1 | 3/2005 | Coppeta et al. |
| 2005/0062603 A1 | 3/2005 | Fuerst et al. |
| 2005/0088289 A1 | 4/2005 | Rochkind |
| 2005/0090781 A1 | 4/2005 | Baba et al. |
| 2005/0134433 A1 | 6/2005 | Sweeney, II |
| 2005/0137530 A1 | 6/2005 | Campbell et al. |
| 2005/0148931 A1 | 7/2005 | Juhasz |
| 2005/0148945 A1 | 7/2005 | Chen |
| 2005/0150488 A1 | 7/2005 | Dave |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0182358 A1 | 8/2005 | Veit et al. |
| 2005/0183982 A1 | 8/2005 | Giewercer |
| 2005/0190941 A1 | 9/2005 | Yang |
| 2005/0192530 A1 | 9/2005 | Castellano |
| 2005/0197654 A1 | 9/2005 | Edman et al. |
| 2005/0209558 A1 | 9/2005 | Marx |
| 2005/0209569 A1 | 9/2005 | Ishikawa et al. |
| 2005/0261742 A1 | 11/2005 | Nova et al. |
| 2005/0267403 A1 | 12/2005 | Landau et al. |
| 2005/0273059 A1 | 12/2005 | Mernoe et al. |
| 2005/0277891 A1 | 12/2005 | Sibbitt |
| 2006/0022806 A1 | 2/2006 | Auerbach |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0074519 A1 | 4/2006 | Barker et al. |
| 2006/0089592 A1 | 4/2006 | Kadhiresan et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129090 A1 | 6/2006 | Moberg et al. |
| 2006/0169611 A1 | 8/2006 | Prindle |
| 2006/0169773 A1 | 8/2006 | Lyons et al. |
| 2006/0189938 A1 | 8/2006 | Hommann et al. |
| 2006/0200077 A1 | 9/2006 | Righi et al. |
| 2006/0204939 A1 | 9/2006 | Bardsley et al. |
| 2006/0247578 A1 | 11/2006 | Arguendas et al. |
| 2006/0247579 A1 | 11/2006 | Friedman |
| 2006/0265186 A1 | 11/2006 | Holland et al. |

(56) References Cited

U.S. PATENT DOCUMENTS

| | | |
|---|---|---|
| 2006/0281435 A1 | 12/2006 | Shearer et al. |
| 2007/0008113 A1 | 1/2007 | Spoonhower et al. |
| 2007/0074722 A1 | 4/2007 | Giroux et al. |
| 2007/0111175 A1 | 5/2007 | Raven et al. |
| 2007/0149954 A1 | 6/2007 | Hood et al. |
| 2007/0184847 A1 | 8/2007 | Hansen et al. |
| 2007/0186923 A1 | 8/2007 | Poutiatine et al. |
| 2007/0210147 A1 | 9/2007 | Morrone et al. |
| 2007/0213598 A1 | 9/2007 | Howard et al. |
| 2007/0233001 A1 | 10/2007 | Burroughs et al. |
| 2007/0239116 A1 | 10/2007 | Follman et al. |
| 2007/0239140 A1 | 10/2007 | Chechelski et al. |
| 2007/0260210 A1 | 11/2007 | Conroy |
| 2007/0276320 A1 | 11/2007 | Wall et al. |
| 2007/0285238 A1 | 12/2007 | Batra |
| 2007/0285258 A1 | 12/2007 | Hartman |
| 2008/0021521 A1 | 1/2008 | Shah et al. |
| 2008/0097311 A1 | 4/2008 | Dacquay et al. |
| 2008/0111685 A1 | 5/2008 | Olson et al. |
| 2008/0140018 A1 | 6/2008 | Enggaard et al. |
| 2008/0160492 A1 | 7/2008 | Campbell et al. |
| 2008/0228143 A1 | 9/2008 | Stamp |
| 2008/0230057 A1 | 9/2008 | Sutherland |
| 2008/0234625 A1 | 9/2008 | Dacquay et al. |
| 2009/0030285 A1 | 1/2009 | Andersen |
| 2009/0062728 A1 | 3/2009 | Woo |
| 2009/0067973 A1 | 3/2009 | Eliuk et al. |
| 2009/0069787 A1 | 3/2009 | Estes et al. |
| 2009/0131875 A1 | 5/2009 | Green |
| 2009/0143761 A1 | 6/2009 | Cantor et al. |
| 2009/0194104 A1 | 8/2009 | Van Sickle |
| 2009/0299156 A1 | 12/2009 | Simpson et al. |
| 2010/0060464 A1 | 3/2010 | Larsen |
| 2010/0111066 A1 | 5/2010 | Mehta |
| 2010/0169111 A1 | 7/2010 | Brue et al. |
| 2010/0192948 A1 | 8/2010 | Sutherland et al. |
| 2010/0208146 A1 | 8/2010 | Reams |
| 2010/0211005 A1 | 8/2010 | Edwards et al. |
| 2010/0214095 A1 | 8/2010 | Davide |
| 2010/0217244 A1* | 8/2010 | Mann ............... A61M 5/14244 604/891.1 |
| 2010/0250280 A1 | 9/2010 | Sutherland |
| 2010/0250697 A1 | 9/2010 | Hansen et al. |
| 2010/0267357 A1 | 10/2010 | Holmstrom et al. |
| 2010/0268303 A1 | 10/2010 | Mitchell et al. |
| 2010/0286612 A1 | 11/2010 | Cirillo |
| 2010/0309012 A1* | 12/2010 | Edwards ............ A61M 5/2046 604/93.01 |
| 2011/0046698 A1 | 2/2011 | Kivi et al. |
| 2011/0112473 A1 | 5/2011 | Bochenko et al. |
| 2011/0144574 A1 | 6/2011 | Kamen et al. |
| 2011/0264033 A1 | 10/2011 | Jensen et al. |
| 2011/0295215 A1 | 12/2011 | Nielsen et al. |
| 2012/0015335 A1 | 1/2012 | Smith et al. |
| 2012/0046613 A1 | 2/2012 | Plumptre |
| 2012/0052837 A1 | 3/2012 | Reich et al. |
| 2012/0071819 A1 | 3/2012 | Bruggemann et al. |
| 2012/0081225 A1 | 4/2012 | Waugh et al. |
| 2012/0083666 A1 | 4/2012 | Waugh et al. |
| 2012/0101444 A1 | 4/2012 | Muller-Pathle et al. |
| 2012/0107783 A1 | 5/2012 | Julian et al. |
| 2012/0165747 A1 | 6/2012 | Lanin et al. |
| 2012/0217184 A1* | 8/2012 | Edwards ............ A61K 31/485 128/200.14 |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0271243 A1 | 10/2012 | Plumptre et al. |
| 2013/0072897 A1 | 3/2013 | Day et al. |
| 2013/0079708 A1 | 3/2013 | Wimpenny et al. |
| 2013/0079725 A1 | 3/2013 | Shang et al. |
| 2013/0110050 A1 | 5/2013 | Boyd et al. |
| 2013/0131601 A1 | 5/2013 | Pommerau et al. |
| 2013/0138040 A1 | 5/2013 | Weinandy |
| 2013/0138444 A1 | 5/2013 | George |
| 2013/0151162 A1 | 6/2013 | Harris et al. |
| 2013/0236872 A1 | 9/2013 | Laurusonis et al. |
| 2013/0266919 A1 | 10/2013 | Baker et al. |
| 2014/0004808 A1 | 1/2014 | Li et al. |
| 2014/0081662 A1* | 3/2014 | Bradrick ............ A61B 5/14503 705/2 |
| 2014/0082501 A1 | 3/2014 | Bae et al. |
| 2014/0155827 A1 | 6/2014 | Ostrander et al. |
| 2014/0207099 A1 | 7/2014 | Nagar |
| 2014/0243749 A1 | 8/2014 | Edwards et al. |
| 2014/0257241 A1 | 9/2014 | Sutkin et al. |
| 2014/0276385 A1 | 9/2014 | Baker et al. |
| 2014/0296824 A1 | 10/2014 | Edwards et al. |
| 2014/0354998 A1 | 12/2014 | Bock et al. |
| 2014/0371714 A1 | 12/2014 | Edwards et al. |
| 2014/0379874 A1 | 12/2014 | Starr et al. |
| 2015/0045729 A1 | 2/2015 | Denzer et al. |
| 2015/0051538 A1 | 2/2015 | Hata et al. |
| 2015/0112707 A1 | 4/2015 | Manice et al. |
| 2015/0196711 A1 | 7/2015 | Edwards et al. |
| 2015/0202367 A1 | 7/2015 | Plaschkes et al. |
| 2015/0208981 A1 | 7/2015 | Oh et al. |
| 2015/0294551 A1* | 10/2015 | Edwards ................. G09B 9/00 340/635 |
| 2016/0018872 A1 | 1/2016 | Tu et al. |
| 2016/0021470 A1 | 1/2016 | Gustafsson |
| 2016/0121056 A1 | 5/2016 | Edwards et al. |
| 2016/0129182 A1 | 5/2016 | Schuster et al. |
| 2016/0157816 A1 | 6/2016 | Denny |
| 2016/0166768 A1 | 6/2016 | Edwards et al. |
| 2016/0184535 A1 | 6/2016 | Edwards et al. |
| 2016/0235916 A1 | 8/2016 | Edwards et al. |
| 2016/0256639 A1 | 9/2016 | Van Sickle et al. |
| 2016/0296716 A1 | 10/2016 | Cabiri et al. |
| 2016/0320210 A1 | 11/2016 | Nelson et al. |
| 2016/0325058 A1 | 11/2016 | Samson et al. |
| 2016/0342748 A1 | 11/2016 | Gulfo et al. |
| 2017/0049954 A1 | 2/2017 | Edwards et al. |
| 2017/0068799 A1 | 3/2017 | Mesinger et al. |
| 2017/0092101 A1 | 3/2017 | Edwards et al. |
| 2017/0106178 A1 | 4/2017 | Altschul et al. |
| 2017/0109498 A1 | 4/2017 | Childress et al. |
| 2017/0196771 A1 | 7/2017 | Hooven et al. |
| 2017/0270276 A1 | 9/2017 | Saint et al. |
| 2017/0286638 A1 | 10/2017 | Searle et al. |
| 2017/0328931 A1 | 11/2017 | Zhang et al. |
| 2018/0028142 A1 | 2/2018 | Bhatia et al. |
| 2018/0028755 A1 | 2/2018 | Philip et al. |
| 2018/0033286 A1 | 2/2018 | Edwards et al. |
| 2018/0102066 A1 | 4/2018 | Edwards et al. |
| 2018/0103908 A1* | 4/2018 | Balczewski ......... A61B 5/0031 |
| 2018/0110923 A1 | 4/2018 | Kaplan et al. |
| 2018/0140788 A1 | 5/2018 | Calderon Oliveras et al. |
| 2018/0151053 A1 | 5/2018 | Edwards et al. |
| 2018/0158374 A1 | 6/2018 | Zamierowski et al. |
| 2018/0204636 A1 | 7/2018 | Edwards et al. |
| 2018/0207366 A1 | 7/2018 | Marcoz et al. |
| 2018/0289901 A1 | 10/2018 | Bøggild-damkvist et al. |
| 2018/0304018 A1* | 10/2018 | Blondino ............ G09B 23/285 |
| 2019/0046727 A1 | 2/2019 | Aneas |
| 2019/0151548 A1 | 5/2019 | Edwards et al. |
| 2019/0217004 A1 | 7/2019 | Edwards et al. |
| 2019/0279756 A1 | 9/2019 | Edwards et al. |
| 2019/0358399 A1 | 11/2019 | Edwards et al. |
| 2020/0086069 A1 | 3/2020 | Riebe et al. |
| 2020/0168124 A1 | 5/2020 | Baker et al. |
| 2020/0206438 A1 | 7/2020 | Baker et al. |
| 2020/0214625 A1 | 7/2020 | Hooven et al. |
| 2021/0244894 A1 | 8/2021 | Edwards et al. |
| 2022/0355034 A1 | 11/2022 | Edwards et al. |

FOREIGN PATENT DOCUMENTS

| | | |
|---|---|---|
| EP | 1712178 A2 | 10/2006 |
| EP | 1095668 | 4/2007 |
| EP | 1777984 A1 | 4/2007 |
| EP | 1883268 A2 | 1/2008 |
| WO | WO 93/02720 | 2/1993 |
| WO | WO 93/23096 | 11/1993 |

(56) References Cited

FOREIGN PATENT DOCUMENTS

| WO | WO 95/26009 | | 9/1995 |
|---|---|---|---|
| WO | WO 96/25965 | | 8/1996 |
| WO | WO 98/52632 | | 11/1998 |
| WO | WO 99/07425 | | 2/1999 |
| WO | WO 99/10031 | | 3/1999 |
| WO | WO 99/43283 | | 9/1999 |
| WO | WO 2001/003758 | | 1/2001 |
| WO | WO 2001/024690 | | 4/2001 |
| WO | WO 2001/026020 | | 4/2001 |
| WO | WO 2001/088828 | | 11/2001 |
| WO | WO 2001/093926 | | 12/2001 |
| WO | WO 2003/095001 | | 11/2003 |
| WO | WO 2004/022138 | | 3/2004 |
| WO | WO 2005/050526 | | 6/2005 |
| WO | WO 2005/074790 | | 8/2005 |
| WO | WO 2005/039673 | | 5/2006 |
| WO | WO 2006/045525 | | 5/2006 |
| WO | WO 2006/109778 | | 10/2006 |
| WO | WO 2006/123956 | | 11/2006 |
| WO | WO 2006/125692 | | 11/2006 |
| WO | WO 2007/087304 | | 8/2007 |
| WO | WO 2008/005315 | | 1/2008 |
| WO | WO 2008/008451 | | 1/2008 |
| WO | WO 2008/148864 | | 12/2008 |
| WO | WO 2010/114392 | | 10/2010 |
| WO | WO 2012/063172 | | 5/2012 |
| WO | WO 2012/164402 | A2 | 12/2012 |
| WO | WO 2013/033467 | A1 | 3/2013 |
| WO | WO 2013/043063 | | 3/2013 |
| WO | WO 2013/154954 | | 10/2013 |
| WO | WO 2013/164628 | A1 | 11/2013 |
| WO | WO 2014/008393 | A1 | 1/2014 |
| WO | WO 2014/036308 | A2 | 3/2014 |
| WO | WO 2014/089083 | A1 | 6/2014 |
| WO | WO 2014/116987 | A1 | 7/2014 |
| WO | WO 2014/143815 | A1 | 9/2014 |
| WO | WO 2014/144096 | A1 | 9/2014 |
| WO | WO 2015/044102 | A1 | 4/2015 |
| WO | WO 2015/044112 | A1 | 4/2015 |
| WO | WO2015/055588 | | 4/2015 |
| WO | WO 2016/151042 | A1 | 9/2016 |
| WO | WO 2016/210404 | | 12/2016 |
| WO | WO 2017/013463 | | 1/2017 |
| WO | WO 2017/013464 | | 1/2017 |
| WO | WO 2017/132577 | | 8/2017 |
| WO | WO 2017/178865 | | 10/2017 |
| WO | WO 2018/013419 | | 1/2018 |
| WO | WO 2017/221242 | A1 | 12/2018 |
| WO | WO 2019/063307 | A1 | 4/2019 |
| WO | WO 2020/018443 | A1 | 1/2020 |

OTHER PUBLICATIONS

"How to Use Auvi-Q?" posted by user NorthCoAllergyAsthma. Posting date: Mar. 18, 2013. Retrieval date: Oct. 18, 2018. Retrieved from the Internet: https://www.youtube.com/watch?v+bZ15vXwZUOg (Year: 2013).

Examination report No. 1 for AU Application No. 2018210313, dated Aug. 12, 2022.

"Solutions for Medical Devices," 3M Brochure, © 3M, (2006), 80-6201-3490-0, 8 pages.

Tingelstad, M., "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=articlePrint&ArticleID=CA6332947>, 3 pages.

"Flexible circuits / Flex circuits / Flexible Technology Ltd.," Flexible Technology Limited [online] [retrieved on Aug. 28, 2006] Retrieved from the Internet <URL: http://www.flexibletechnology.com/ >, 2 pages.

"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible circuits Capability.htm >, 2 pages.

"Flex Circuits/flexible circuits design guide," [online] [retrieved on Aug. 28, 2006] Retrieved from the Internet <URL: http://flexiblecircuit.co.uk/Flex Circuits Design Guide.htm >, 7 pages.

"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html>, 3 pages.

"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/product catalogue.asp >, 9 pages.

"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1>, 3 pages.

Allan, R., "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>, 3 pages.

RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >, 2 pages.

"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8>, 3 pages.

Scholz, O., "Drug depot in a tooth," [online] [retrieved on Feb. 6, 2007] Retrieved from the Internet <URL: http://www.fraunhofer.de/fhg/EN/press/pi/2007/02Mediendienst22007Thema2.jsp?print=true>, 1 page.

Heartsine Technology, samaritan™ Pad Accessories [online] [retrieved on Jun. 1, 2007] Retrieved from the Internet <URL: http://www.heartsine.com/aboutsam-accessories.htm>, 4 pages.

CliniSense Corporation, "Drug delivery devices A potentially harsh environment for drugs," Stability [online] [retrieved on Jun. 1, 2007] Retrieved from the Internet <URL: http://www.clinisense.com/devices.htm>, 2 pages.

CliniSense Corporation, "LifeTrack Technology A new method to detect improper storage." Stability [online] [retrieved on Jun. 1, 2007] Retrieved from the Internet <URL: http://www.clinisense.com/tech.htm>, 2 pages.

AED Professionals™ Brochure [online] [retrieved on Jun. 1, 2007] Retrieved from the Internet <URL: http://www.aedprofessionals.com>, 4 pages.

Ruppar, D., "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/drugdelivery/200702/templates/pageviewer_print?pg=44&pm=8 >, 8 pages.

Meridian Medical Technologies, Inc., "Pralidoxime Chloride Trainer," 2006. [retrieved on Feb. 16, 2007] Retrieved from the Internet <URL: http://www.meridianmeds.com/auto-injectors/2pamcl_trainer.html/>, 1 pages.

Gosbee, L. L., "Nuts! I Can't Figure Out How to Use My Life-Saving Epinephrine Auto-Injector," Joint Commision Journal on Quality and Safety, 30(4):220-223 (Apr. 2004).

Amgen, "Using Aranesp prefilled SureClick autoinjector is a simple 3-step process," 2006. [retrieved on Feb. 16, 2007] Retrieved from the Internet <URL: http://www.aranesp.com/patient/cia/sureclick/using_three_steps.jsp/>, 4 pages.

Apple, Inc., "Bluetooth Accessory Design Guidelines for Apple Products," Release R7, (Sep. 18, 2013), 40 pages.

Stuart, M., "Cellnovo's Mobile Health Approach to Diabetes Care," In Vivo: The Business & Medicine Report, (Dec. 2010), pp. 40-44.

Knapp, Louise. "A Faster Way to Call 911," Wired.com [online], [retrieved Jul. 26, 2017] Retrieved from the Internet <https://www.wired.com/2001/03/a-faster-way-to-call-911> (Mar. 10, 2001), 9 pages.

(56) References Cited

OTHER PUBLICATIONS

Libov, Charlotte. "EpiPen 101," Everyday Health [online], [retrieved Jul. 26, 2017] Retrieved from the internet <http://www.everydayhealth.com/allergy/epipen-101.aspx> (Feb. 23, 2012), 2 pages.

Enable Injections. "Enable Connections: A Bluetooth-Connected Wearable, On-Body Injector," OnDrugDelivery Magazine, Retrieved from the internet <http://www.ondrugdelivery.com> (Jun. 21, 2016), 4 pages.

Anonymous: "Bluetooth—Wikipedia, the free encyclopedia", Oct. 11, 2012 (Oct. 11, 2012), XP055295137, retrieved from the Internet: URL: https://en.wikipedia.org/w/index.php?title=Bluetooth&oldid=517244384 (retrieved on Aug. 9, 2019).

Anonymous: "Emergency Call Button on Lock Screen—Apple Community", May 14, 2011 (May 14, 2011), XP055494181, Retrieved from the Internet: URL: https://discussions.apple.com/thread/2783061 (retrieved on May 7, 2020).

Office Action for U.S. Appl. No. 14/142,287, dated Apr. 6, 2017.

Office Action for Australia Patent Application No. 2015249064, dated Aug. 25, 2017.

International Search Report and Written Opinion for International Application No. PCT/US2018/013855, dated Jul. 5, 2018.

Office Action for U.S. Appl. No. 15/872,162, dated Oct. 18, 2018.

Office Action for Australian Patent Application No. 2017258859, dated Jul. 16, 2019.

Examination Report for EP Application No. 13867489.0, dated Jul. 26, 2019.

Invitation to Pay Additional Fees for PCT Application No. PCT/US19/41823, dated Sep. 18, 2019.

International Search Report & Written Opinion for International Application No. PCT/US2019/041844, dated Oct. 4, 2019.

International Search Report and Written Opinion for PCT/US19/41823, dated Nov. 20, 2019.

Office Action for CA Application No. 2,896,708, dated Dec. 2, 2019.

Office Action for U.S. Appl. No. 16/421,639, dated Jun. 26, 2020.

Final Office for U.S. Appl. No. 16/145,974, dated Aug. 24, 2020.

Extended European Search Report for EP Application No. 18741166.5, dated Sep. 21, 2020.

\* cited by examiner

MEDICAMENT DELIVERY DEVICES WITH WIRELESS CONNECTIVITY AND COMPLIANCE DETECTION

CROSS-REFERENCE TO RELATED APPLICATIONS

This application is a U.S. national stage filing under 35 U.S.C. § 371 of International Application No. PCT/US2019/041823, entitled "Medicament Delivery Devices with Wireless Connectivity and Compliance Detection," filed Jul. 15, 2019, which claims benefit of priority to U.S. Provisional Application No. 62/698,863, entitled "Medicament Delivery Devices with Wireless Connectivity and Compliance Detection," filed Jul. 16, 2018, each of which is incorporated herein by reference in its entirety.

BACKGROUND

The embodiments described herein relate generally to a medical device, and more particularly to a medicament delivery device and/or a simulated medicament delivery device having wireless connectivity. The embodiments described herein can include apparatus and methods to detect and validate a delivery event. The embodiments described herein include apparatus and methods to detect, collect, assess and/or monitor compliance activities and/or pharmacovigilant activities. The embodiments described herein also relate to devices for interacting with and/or monitoring (e.g., wirelessly) such medicament delivery devices and/or simulated medicament delivery devices via a wireless communication module.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure. Because emergency medical facilities may not be available when an individual is suffering from an allergic reaction, some individuals carry a medicament delivery device, such as, for example, an auto-injector, to rapidly self-administer a medicament in response to an allergic reaction.

As another example, naloxone is a medicament that prevents and/or reverses the life-threatening breathing effects of opioids. Known formulations of naloxone can be used, for example, to treat respiratory depression and other indications that result from opioid toxicity. For example, known formulations for naloxone can be used to reverse and/or mitigate the effects of an overdose of a drug containing opioids, such as, for example, prescription opioids like oxycodone or illicit opiates like heroin. In such situations, it is desirable to deliver the naloxone formulation quickly and in a manner that will produce a rapid onset of action. Known methods for delivering naloxone intranasally or via injection, however, often involve completing a series of operations that, if not done properly, can limit the effectiveness of the naloxone formulation. Moreover, because naloxone is often administered during an emergency situation, even experienced and/or trained users may be subject to confusion and/or panic, thereby compromising the delivery of the naloxone formulation.

As yet another example, glucagon is a medicament that is administered to treat patients suffering from hypoglycemia. In certain situations, the onset of hypoglycemia can cause the patient to lose motor coordination and/or lose consciousness. Thus, glucagon is often administered by a care-giver during an emergency situation.

Some known medicament delivery devices, such as, for example, auto-injectors, pen injectors, inhalers, nasal delivery systems, and/or simulated medicament delivery devices are configured to be carried with the user. Although such devices may improve the likelihood of compliance, such portable devices can be susceptible to shortcomings, such as inadequate instructions for use, difficulty of use for untrained users, and the possibility of improper use. Additionally, because such portable devices are small, there is an increased likelihood that such devices will be forgotten and/or misplaced.

In addition to the issues relating to improper use of medicament delivery devices, monitoring the patient's compliance with known medicament delivery devices can also be problematic. For example, many children carry an auto-injector to deliver epinephrine in the event of an allergic reaction. Known epinephrine auto-injectors, however, do not provide robust mechanisms (or communication systems) for alerting a parent or caregiver when the child has enabled and/or used the auto-injector. For example, some known systems produce a notification when an auto-injector is removed from a case. Although this information can be helpful, it does not provide any confirmation of actual use of the device (i.e., delivery of the medicament). Additionally, simply providing an alert upon opening a container and/or removing an auto-injector can result numerous "false positives" when a user simply opens the container and/or removes the device in a situation unrelated to an actual emergency.

Moreover, known medicament delivery devices do not provide a suitable mechanism (or communication systems) for alerting the parent or caregiver when the child is not carrying (or within a suitable range of) the device or provide associated information related to ensuring the device is kept on or with a user at all times. For example, although some known systems produce a notification when a medicament delivery device is not within a predetermined distance from the user's phone, such known systems do not accommodate different usage patterns for different devices that may be owned by the user. For example, known compliance tracking systems do not differentiate between a device that is typically carried with the user and a device that is stored at a predetermined location (e.g., an auto-injector maintained at school or work). Moreover, known compliance tracking systems employ complicated algorithms to determine whether the device is "in range" of the user's phone and are therefore susceptible to false results.

Some known treatment regimens include multiple doses of a medicament that must be administered in a timely fashion and/or in a particular order to ensure effectiveness, especially in more chronic diseases (e.g., insulin for diabetes, certain biologic therapies for inflammatory conditions or certain vaccination regimens). Thus, in addition to alerting a caregiver in an emergency situation, monitoring the patient's adherence to a medication regimen is an important aspect in ensuring that the treatment method will be both safe and effective. Some known medicament delivery systems include a medicament delivery device and an accompanying electronic system to assist the user in setting the proper dosage and/or maintaining a compliance log. Such known medicament delivery systems and the accompanying electronic systems can be large and therefore not conveniently carried by the user. Such known medicament delivery systems and the accompanying electronic systems can also be complicated to use and/or expensive to manufacture. These known systems also do not provide true delivery event detection as they may only rely on one detection sensor or do not have a reliable algorithm for administration detection to ensure adherence to the medicament regimen.

In addition, an extended shelf life may be desirable for some medicament delivery devices, such as devices intended to be carried by a user on a daily basis. For example, an auto-injector intended to be carried by a user on a daily basis may be expected to work after weeks, months, or years without user maintenance. As another example, known emergency-use auto-injectors are single-use devices that are expected to be carried for years before a potential use. The disposable nature and/or extended shelf-life of such devices can further exacerbate the shortcomings described above. For example, the electronics of known stationary devices, particularly known devices having electronic communication means (e.g., for compliance tracking), may not be efficient enough to provide sufficiently long battery life for use in a portable, extended shelf life device. Furthermore, efficient power management may be desirable to extend the useful life of a medicament delivery device, particularly for a device having limited battery capacity, limited or no user replaceable batteries, and/or limited or no charging capacity.

As another way to enhance the likelihood of proper use, some known medicament delivery devices are associated with simulated medicament delivery devices (e.g., "trainers") to provide a method for users to practice using the medicament delivery device without being exposed to the medicament and/or needles typically contained therein. Such simulated medicament delivery devices, however, can also include inadequate use instructions as described above.

Thus, a need exists for medicament delivery systems and/or devices that allow a medicament delivery device to be quickly identified and located, alert the user if the medicament delivery device is forgotten, and provide instructions that can be easily understood by a user in any type of situation. Additionally, a need exists for simulated medicament delivery systems and/or devices that can provide instructions and that can be reused multiple times. Moreover, a need exists for medicament delivery systems and/or devices that can provide compliance information associated with the use of the device and/or that can communicate electronically with other communications devices.

SUMMARY

System and methods to facilitate wireless communications with medicament delivery devices and simulated medicament delivery devices are described herein. In some embodiments, a method includes receiving a signal associated with a characteristic of an actuation event of a medicament delivery device. The method includes establishing a communications link (e.g., via a short-range wireless protocol), between a mobile computing device and a medicament delivery device. A wireless first signal associated with a first motion profile of the medicament delivery device is then received from the medicament delivery device. A second signal associated with a second motion profile of the mobile computing device is generated. The method then includes producing a notification via the mobile computing device when A) a magnitude of the first motion profile is outside of a first threshold and B) a magnitude of the second motion profile is outside of a second threshold.

In some embodiments, a computer-implemented method includes receiving, in response to an input prompt, a user input selecting an output script associated with a medicament delivery device. A communications link is established (e.g., via a short-range wireless protocol), between a mobile computing device and the medicament delivery device. A wireless signal providing instructions to an electronic circuit system of the medicament delivery device to execute the output script when the electronic circuit system of the medicament delivery device is actuated is then transmitted from the mobile computing device.

In some embodiments, a computer-implemented method includes establishing a communications link, via a short-range wireless protocol, between a mobile computing device and a medicament delivery device. The medicament delivery device includes a medicament container, an actuator, and an electronic circuit system. The actuator is configured to initiate delivery of a medicament from the medicament container. The electronic circuit system includes at least one actuation sensor configured to produce an actuation signal in response to at least one of a movement of the actuator relative to the medicament container or a delivery characteristic of delivery of the medicament from the medicament container. A first wireless signal associated with the first actuation signal is received from the medicament delivery device. An event detection notification based on the first wireless signal is then produced. A second wireless signal is transmitted to an emergency response system. The second wireless signal is associated with the event detection notification.

In some embodiments, an apparatus includes a battery housing, a battery, a first clip, and a second clip. The battery housing has an outer surface and a first connector. The first connector defines a connector volume and a keyway. The keyway is configured to be matingly coupled to a second connector of a battery wire. The battery is contained within the battery housing, and has a positive terminal and a negative terminal. The first clip is coupled about the battery housing and the battery. The first clip has a first contact portion, a second contact portion, and a first terminal. The first contact portion is engaged with the outer surface of the battery housing and the second contact portion is engaged with the positive terminal of the battery. The first terminal is within the connector volume. The second clip has a third contact portion and a second terminal. The third contact portion is engaged with the negative terminal of the battery and the second terminal is within the connector volume.

DETAILED DESCRIPTION

Figure 1A:
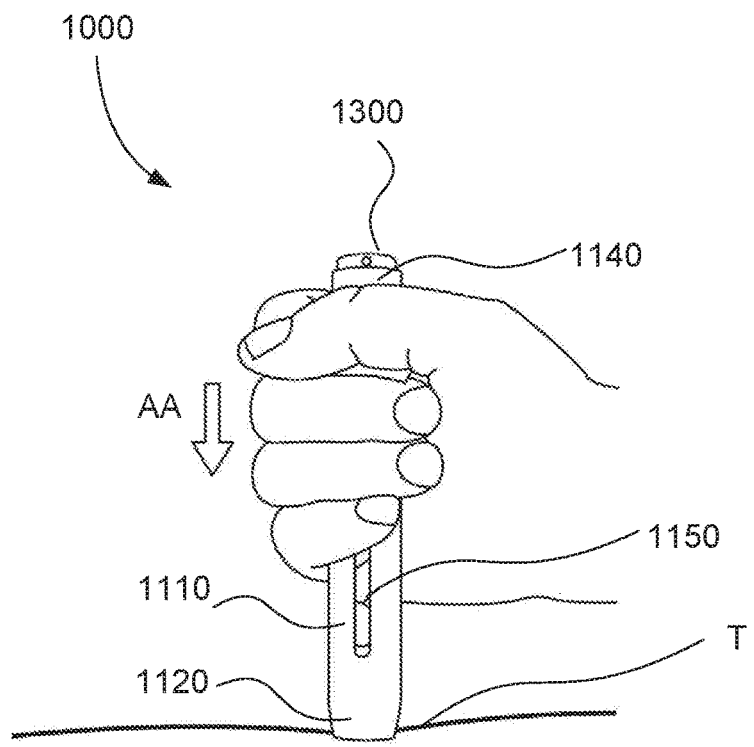
FIGS. 1A-1C are perspective views of a medical injector according to an embodiment of the invention, in a first configuration (FIG. 1A), a second configuration (FIG. 1B), and a third configuration (FIG. 1C).

This application describes devices that are related to and/or can be used with the devices and systems described in U.S. Pat. No. 8,172,082, entitled "Devices Systems and Methods for Medicament Delivery," filed Feb. 5, 2007, U.S. Pat. No. 8,231,573, entitled "Medicament Delivery Device Having an Electronic Circuit System," filed May 12, 2008, and U.S. Pat. No. 8,361,026, entitled Apparatus and Methods for Self-Administration of Vaccines and Other Medicaments," filed Nov. 10, 2009, each of which is incorporated herein by reference in its entirety.

The medicament delivery systems shown and described herein, including any of the service delivery architectures described herein, can be used in conjunction with any suitable medicament delivery device and/or medicament container such that the medicament delivery device and/or medicament container can be easily accessed, identified, located and used, as described herein. In some embodiments, the medicament delivery device can be a medical injector (such as a pen injector, a prefilled syringe, or an auto-injector), an inhaler, a nasal delivery device or the like.

In some embodiments, a simulated medicament delivery device can produce an indication associated with an operation of the simulated medicament delivery device. In response, a recorded speech output can be generated and information associated with the operation can be stored in a memory. A training script can be updated based on the information stored in the memory.

In some embodiments, a computer-implemented method includes receiving an indication associated with an operation from a set of operations associated with a simulated medicament delivery device. The set of operations can be, for example, a series of operations to be taken when actuating an actual medicament delivery device that corresponds to the simulated device. In response to the indication, a recorded speech output associated with a first training script is produced. Additionally, in response to the indication, use information associated with the plurality of operations associated with a simulated medicament delivery device is updated. The method further includes producing, in response to the updated use information, a second training script.

In some embodiments, a computer-implemented method includes establishing a communications link, via a short-range wireless protocol, between a mobile computing device and a medicament delivery device. A user input selecting a motion profile of the medicament delivery device is then received in response to an input prompt. A wireless signal is received from the medicament delivery device, the wireless signal associated with an actual motion profile of the medicament delivery device. A notification is produced to indicate a motion difference between the actual motion profile and the target motion profile. In some embodiments, the method optionally includes modifying the target motion profile based on the motion profile over a time period of at least one week, the notification indicating a motion difference between the motion profile and the modified target motion profile.

In some embodiments, any of the medicament delivery devices (including the devices, housings, containers, or casings) described herein can track and transmit information associated with a motion profile of the medicament delivery device. For example, in some embodiments, a computer-implemented method includes transmitting, from a radio of an electronic circuit system associated with a medicament delivery device, a first wireless signal to establish a communications link between a mobile computing device and the medicament delivery device. A motion signal is received, from a sensor of the electronic circuit system. The motion signal is associated with at least one of a position, a velocity, an acceleration, or an orientation of the medicament delivery device. A motion profile of the medicament delivery device is stored in a memory of the electronic circuit system. The motion profile includes the motion signal received during a time period. A second wireless signal associated with the motion profile of the medicament delivery device is then transmitted from the radio.

In some embodiments, the computer-implemented method can include learning or predicting the expected motion of the medicament delivery device. For example, in some embodiments, in the method above the time period can be at least one week. The method can further include producing, via a predictive module implemented in at least one of the memory or a processing device of the electronic circuit system, a target motion profile based on the motion profile over the time period. A motion difference between the motion profile at a first time and the target motion profile is then stored in the memory. A third wireless signal associated with the motion difference is then transmitted from the radio.

In some embodiments, an apparatus includes a medicament delivery device and an electronic circuit system. The electronic circuit system is coupled to at least one of a housing of the medicament delivery device or a cover configured to receive a portion of the medicament delivery device. The electronic circuit system includes a sensor, a motion module, and a radio. The sensor is configured to produce a motion signal associated with at least one of a position, a velocity, an acceleration, or an orientation of at least one of the housing or the cover. The motion module is implemented in at least one of a memory or a processing device, and receives the motion signal. The motion module is configured to determine, based on the motion signal, a motion profile associated with the medicament delivery device. The radio is configured to electronically communicate with a computing device via a short-range wireless communication protocol. The radio sends a first wireless signal to establish a communications link between the computing device and the medicament delivery device. The radio sends a second wireless signal associated with the motion profile of the medicament delivery device.

In some embodiments, an apparatus includes a medicament delivery device and an electronic circuit system. The medicament delivery device includes a housing, a medicament container at least partially within the housing, an actuator, and a safety member movably coupled to the housing. The safety member is configured to prevent movement of the actuator when the safety member is in a first position. The actuator is movable to actuate the medicament delivery device when the safety member is a second position. The electronic circuit system is coupled to at least one of the housing of the medicament delivery device or the safety member. The electronic circuit system includes a processing device, an output device, a first sensor, a second sensor, and a power management module. The electronic circuit system is configured to produce a first electronic output via the output device when the first sensor produces a safety signal. The safety member configured to actuate the first sensor when the safety member is moved from the first position to the second position. The electronic circuit system is configured to produce a second electronic output when the second sensor produces an actuation signal. The actuator is configured to actuate the second sensor when the actuator is moved. The power management module is implemented in at least one of a memory or the processing device, and is configured to modify the first electronic output when a number of times the safety member has actuated the first sensor exceeds a threshold safety member number.

In some embodiments, an apparatus includes a medicament delivery device and an electronic circuit system. The medicament delivery device includes a housing, a medicament container at least partially within the housing, and an actuator. The actuator is configured to move relative to the housing to initiate delivery of a medicament from the medicament container. The electronic circuit system is coupled to at least one of the housing or a cover configured to receive at least a portion of the medicament delivery device. The electronic circuit system includes a processing device, an output device, a set of sensors, a power source and a power management module. The electronic circuit system is configured to produce a set of electronic outputs via the output device in response to a set of signals produced by any of the sensors. The signals are associated with at least one of a use of the medicament delivery device, a movement of the medicament delivery device, or a position of the medicament delivery device. The power management module is implemented in at least one of a memory or the processing device, and is configured to modify at least one of the plurality of electronic outputs based on a power level of the power source. In some embodiments, for example, the power management module is configured to suppress at least one of the electronic outputs.

In some embodiments, an apparatus includes a medicament delivery device and an electronic circuit system. The medicament delivery device includes a housing, a medicament container at least partially within the housing, and an actuator. The actuator is configured to move relative to the housing to initiate delivery of a medicament from the medicament container. The electronic circuit system is coupled to at least one of the housing or a cover configured to receive at least a portion of the medicament delivery device. The electronic circuit system includes a processing device, an output device, a radio, a set of sensors, a power source and a power management module. The electronic circuit system is configured to produce a set of electronic outputs via the output device in response to a set of signals produced by any of the sensors. The signals are associated with at least one of a use of the medicament delivery device, a movement of the medicament delivery device, or a position of the medicament delivery device. The electronic circuit system is configured to produce a set of wireless communication signals via the radio in response to the set of signals produced by any of the sensors. The power management module is implemented in at least one of a memory or the processing device, and is configured to suppress at least one of the wireless communication signals while maintaining the electronic outputs based on a power level of the power source.

In some embodiments, a computer-implemented method includes establishing a communications link, via a short-range wireless protocol, between a mobile computing device and a medicament delivery device. The communications link established within a first application executed by a processor of the mobile computing device. A wireless signal associated with a characteristic of the medicament delivery device is received from the medicament delivery device. Information associated with the medicament delivery device is received from a second application executed by the processor of the mobile computing device. A notification based on the characteristic and the information is then produced via a user interface of the first application.

The term "about" when used in connection with a referenced numeric indication means the referenced numeric indication plus or minus up to 10% of that referenced numeric indication. For example, "about 100" means from 90 to 110.

As used herein, the term "medicament" includes any constituent of a therapeutic substance. A medicament can include such constituents regardless of their state of matter (e.g., solid, liquid or gas). Moreover, a medicament can include the multiple constituents that can be included in a therapeutic substance in a mixed state, in an unmixed state and/or in a partially mixed state. A medicament can include both the active constituents and inert constituents of a therapeutic substance. Accordingly, as used herein, a medicament can include non-active constituents such as, water, colorant or the like.

In a similar manner, term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±10% of the stated geometric construction, numerical value, and/or range. Furthermore, although a numerical value modified by the term "substantially" can allow for and/or otherwise encompass a tolerance of the stated numerical value, it is not intended to exclude the exact numerical value stated.

As used herein, the term "set" can refer to multiple features or a singular feature with multiple parts. For example, when referring to a set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method).

As used in this specification and the appended claims, the words "proximal" and "distal" refer to direction closer to and away from, respectively, an operator of the medical device. Thus, for example, the end of the medicament delivery device contacting the patient's body would be the distal end of the medicament delivery device, while the end opposite the distal end would be the proximal end of the medicament delivery device.

Figure 1B:
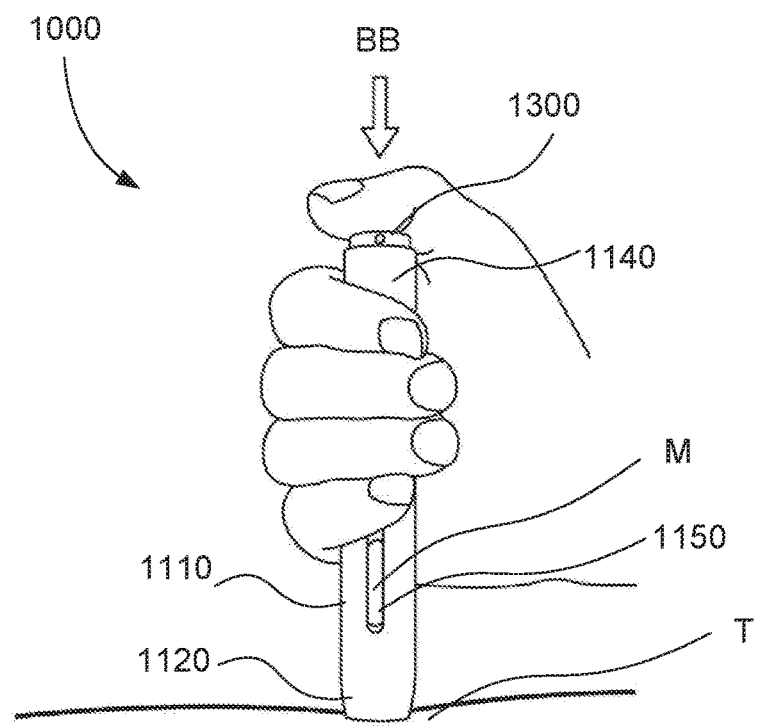
Figure 1C:
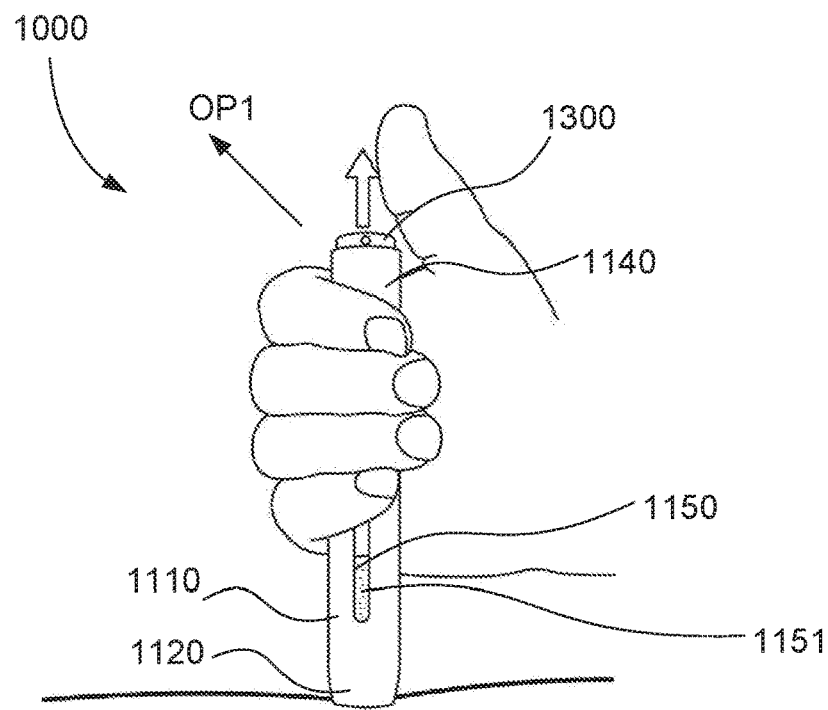

The methods and systems described herein can be used in conjunction with any suitable medicament delivery device, including any of the delivery devices (or drug products) described herein. For example, FIGS. 1A-1C show a medical injector 1000 according to an embodiment having an electronic circuit system (not shown) that has wireless connectivity. The medical injector 1000 can be included in any of the connected health medicament delivery systems shown and described herein, such as the connected health medicament delivery systems 5800, 6800, and 7800 described herein. The medical injector 1000 can include any of the features of any of the devices shown and described herein, including the features shown and described with reference to the device 4000. For example, the medical injector 1000 can include a carrier, that functions similar to the carrier 4520, that holds and/or moves a medicament container during use.

The medical injector 1000 includes, among other components, a housing 1110, an actuator 1300, and an electronic circuit system (not shown). The housing 1100 contains the components of the medical injector 1000, and includes a proximal end portion 1140 and a distal end portion 1120. The housing 1110 defines a status indicator aperture 1150. The status indicator aperture 1150 can allow a patient to monitor the status and/or contents of a medicament container, identified as the medicament M in FIG. 1A (the medicament container is not shown but is located within the housing 1110). For example, by visually inspecting the status indicator aperture 1150, a patient can determine whether the medicament container contains the medicament M and/or whether a medicament has been dispensed. The distal end portion 1120 of the housing includes a surface that can be pressed against a target location T during a delivery event, as shown by the arrow AA in FIG. 1A. The target location T can be any location on the body, such as the patient's thigh, arm, abdomen, or any other desired location for delivery.

The actuator 1300 is coupled to the proximal end portion 1140 (i.e., the non-delivery end) of the housing 1110, and can be moved relative to the housing 1110 to actuate the medical injector 1000. Similarly stated, the actuator 1300 can be manually manipulated (as shown by the arrow BB in FIG. 1B) to initiate delivery of a medicament from the medicament container within the housing 1110. In some embodiments, the actuator 1300 can also be used to set or adjust a dose of the medicament to be delivered. For example, in some embodiments, the medical injector 1000 can include multiple doses (e.g., for a chronic care condition), and the actuator can be rotated, twisted, or otherwise moved to adjust the amount of medicament to be delivered. In some embodiments, the electronic circuit system can provide instructions to the user to assist in setting the dose, can produce one or more electronic outputs (e.g., voice prompts, beeps, wireless signals) that confirm the dose setting, or the like.

In some embodiments, the medical injector 1000 includes an energy storage member (not shown), such as a spring, a compressed gas container, a chemical energy storage member or the like. When the actuator 1300 is manipulated, the energy storage member can produce a force that inserts a delivery member (e.g., a needle), conveys a dose of medicament from the medical injector, or both of these functions. In some embodiments, the medical injector 1000 can be a pen injector that does not produce an automatic needle insertion, but rather relies up on the user to manually insert the needle into the target location T.

Although not shown in FIGS. 1A-1C, the medicament container of the medical injector 1000 can be any suitable medicament container. For example, in some embodiments, the medicament container can be a sealed container similar to the container 4560 described herein. The medicament container can be coupled to and/or supported by a carrier or other structure within the housing that facilitates actuation of the device. In other embodiments, the medicament container can be a prefilled syringe that is not sealed at its distal end. Such prefilled syringes can include a staked needle, or in other embodiments, a coupleable needle (e.g., via a Luer fitting or the like). For example, the medicament container (and any of the medicament containers herein) can be similar to the prefilled syringe assemblies shown and described in International Patent Publication No. WO2017/004345, entitled "Auto-Injectors for Administration of a Medicament within a Prefilled Syringe," which is incorporated herein by reference in its entirety. The medical injector 1000 can include and delivery any suitable volume of any of the medicaments described herein.

The electronic circuit system of the medical injector 1000 can include any suitable components to perform any of the functions described herein, including functions associated with the electronic circuit systems 4900, 5900 described herein. Specifically, the electronic circuit system of the medical injector 1000 can include any of a printed circuit board, a battery assembly, an audio output device, light emitting diodes (LEDs), a series of sensors and switches, and a processor that includes wireless communication functionality. The electronic circuit system can be coupled to or within the medical injector 1000 in any suitable fashion. For example, in some embodiments, the electronic circuit system can be coupled within the housing 1110. In other embodiments, the electronic circuit system can be coupled to an outer surface of the housing 1110 (e.g., as a wrap-on label). In some embodiments, for example, the electronic circuit system can include a housing that snaps on to (i.e., forms an interference fit with) a portion of the housing 1110, such as for example, the electronic circuit system 5900 shown in FIGS. 35-41. In this manner, the electronic circuit system can be assembled separately from the medical injector and later coupled to the medical injector. This modular approach can allow the electronic circuit system and its associated functions to be an optional part of the drug delivery system. For example, in some embodiments, any of the electronic circuit systems can be a modular ("snap on") system of the types shown in International Patent Publication No. WO2017/004345, entitled "Auto-Injectors for Administration of a Medicament within a Prefilled Syringe," which is incorporated herein by reference in its entirety.

The electronic circuit system is configured to output one or more electronic outputs, including wireless signals, associated with the use of the medical injector 1000. The electronic circuit system can therefore communicate with (either directly or indirectly via a network) other devices within any of the connected health medicament delivery systems shown and described herein, such as the connected health medicament delivery systems 5800, 6800, and 7800 described herein.

To use the medical injector 1000, the medical injector 1000 and the target location T are first prepared for delivery (e.g., removal of a safety guard, cleansing of the target location, etc.) The distal end portion 1120 of the housing 1110 is then pressed against the target location T, as shown by the arrow AA in FIG. 1A. The actuator 1300 is then manipulated as shown by the arrow BB in FIG. 1B to initiate delivery of the medicament M. Upon completion of the medicament delivery, a status indicator 1151 is visible via the status aperture 1150. The status indicator 1151 can be a portion of a carrier, a portion of a plunger, a sleeve, or any other component within the housing 1110 that moves into view of the status aperture 1150 after successful delivery of the dose. In some embodiments, the status indicator 1151 can be an electronic indicator (e.g., an LED, electronic paper, or other indicator) that is produced by the electronic circuit system to indicate successful delivery of the dose.

Figure 3:
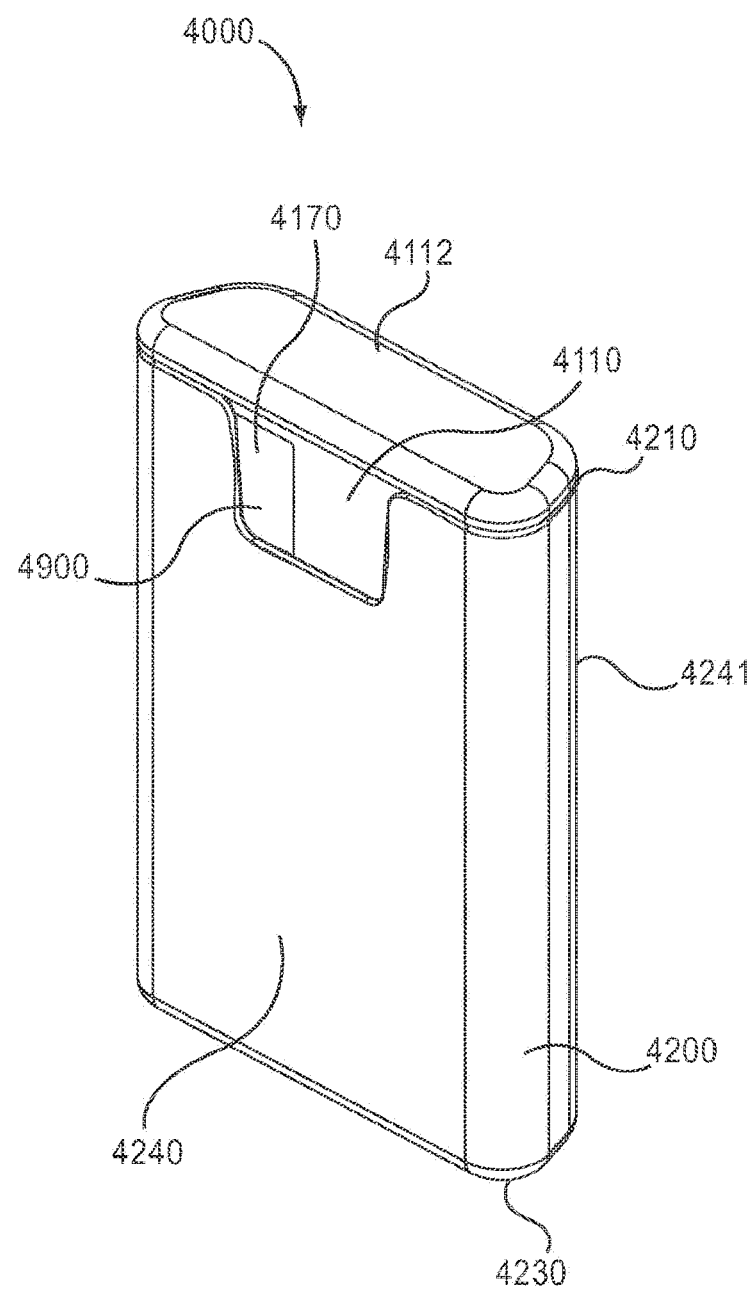
FIGS. 3 and 4 are perspective views of a medical injector according to an embodiment of the invention, in a first configuration.

The electronic circuit system can produce any number of electronic outputs, indicated as OP1 in FIG. 3, at any time before, during, or after the delivery event. The electronic output OP1 can be any of the outputs described herein (audible output, visual output, wireless communication signal, etc.). For example, in some embodiments, the electronic circuit system can output a wireless electronic output that is received by a computing device (e.g., a user's mobile phone, such as the computing device 7801 described herein). Such wireless outputs can be any wireless outputs of the types shown and described herein.

Figure 2:
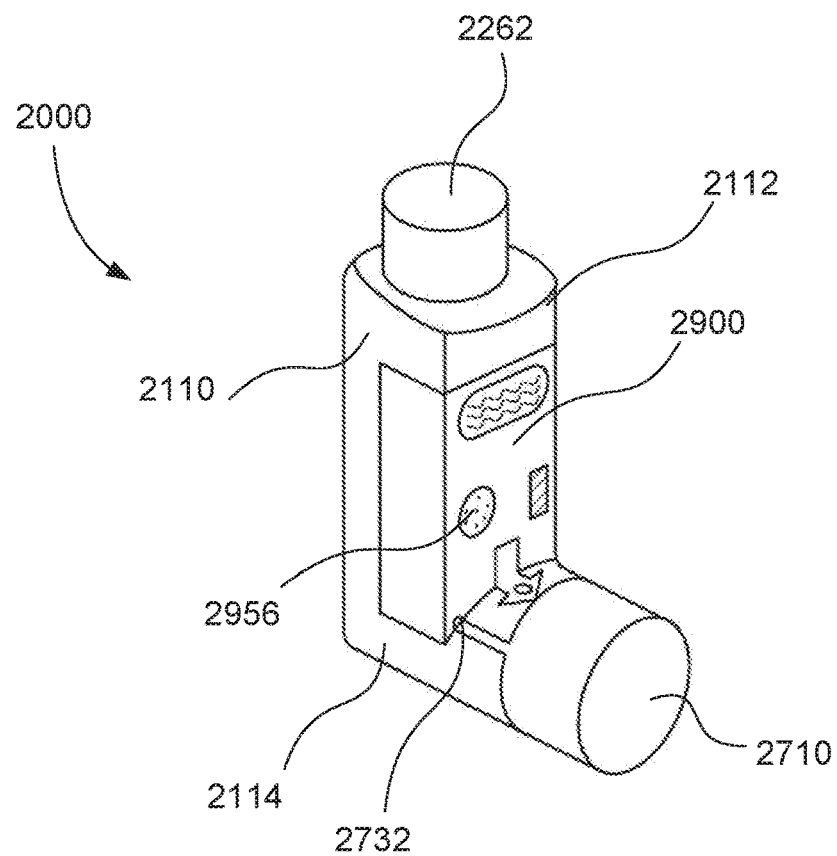
FIG. 2 is a perspective view of an inhaler according to an embodiment.

FIG. 2 shows an inhaler 2000 according to an embodiment. The inhaler 2000 includes a housing 2110, a medicament container 2262 movably disposed within the housing 2110, and an electronic circuit system 2900. The medicament container 2262 is configured to discharge a predetermined volume of medicament when the inhaler 2000 is actuated. The medicament container can contain any of the medicaments described herein. The housing 2110 has a proximal end portion 2112 and a distal end portion 2114. The proximal end portion 2112 defines an opening within which the medicament container 2262 is received. The distal end portion 2114 of the housing 2110 includes a mouthpiece about which a protective cap 2710 is disposed.

The electronic circuit system 2900 can include any suitable components to perform any of the functions described herein, including functions associated with the electronic circuit systems 4900, 5900 described herein. Specifically, the electronic circuit system 2900 can include any of a printed circuit board, a battery assembly, an audio output device, light emitting diodes (LEDs), a series of sensors and switches, and a processor that includes wireless communication functionality. The electronic circuit system 2900 can be coupled to or within the housing 2110 in any suitable fashion. For example, in some embodiments, the electronic circuit system can be coupled within the housing 2110. In other embodiments, as shown in FIG. 2, the electronic circuit system 2900 can be coupled to an outer surface of the housing 2110 (e.g., as a wrap-on label). In some embodiments, for example, the electronic circuit system 2900 can include a housing that snaps on to (i.e., forms an interference fit with) a portion of the housing 2110, such as for example, the electronic circuit system 5900 shown in FIGS. 35-41. In this manner, the electronic circuit system can be assembled separately from the inhaler 2000 and later coupled to the inhaler.

Prior to use, the inhaler 2000 is first enabled by removing the protective cap 2710. In some embodiments, the protective cap 2710 includes an actuator 2732 that actuates the electronic circuit system 2920 to trigger a predetermined output (e.g., wireless signal) or sequence of outputs when the protective cap 2710 is removed. In some embodiments, the actuator 2732 can include a protrusion that is received by an actuation portion of the electronic circuit system 2900, in a similar manner as described herein with respect to the medical injector 4000. In other embodiments, the actuator 2732 can be configured to engage a microswitch that can be repeatedly moved between a first state and a second state. After the inhaler 2000 is enabled and placed within the mouth of the patient, the inhaler 2000 is actuated by moving the medicament container 2262 distally within housing 2110. In some embodiments, the medicament container 2262 can include an actuator (not shown) that actuates the electronic circuit system 2900, in a manner similar to those described above, to trigger a predetermined output or sequence of outputs. For example, in some embodiments, the processor can output an electronic signal associated with recorded speech to a speaker 2956. Such an electronic signal can be, for example, associated with a recorded message notifying the user that the delivery is complete, instructing the user on post-delivery procedures, instructing the user on post-delivery medical treatment or the like. Moreover, the electronic output produced by the electronic circuit system 2900 can be any of the outputs described herein (audible output, visual output, wireless communication signal, etc.). For example, in some embodiments, the electronic circuit system 2900 can output a wireless electronic output that is received by a computing device (e.g., a user's mobile phone, such as the computing device 7801 described herein). Such wireless outputs can be any wireless outputs of the types shown and described herein.

Figure 4:
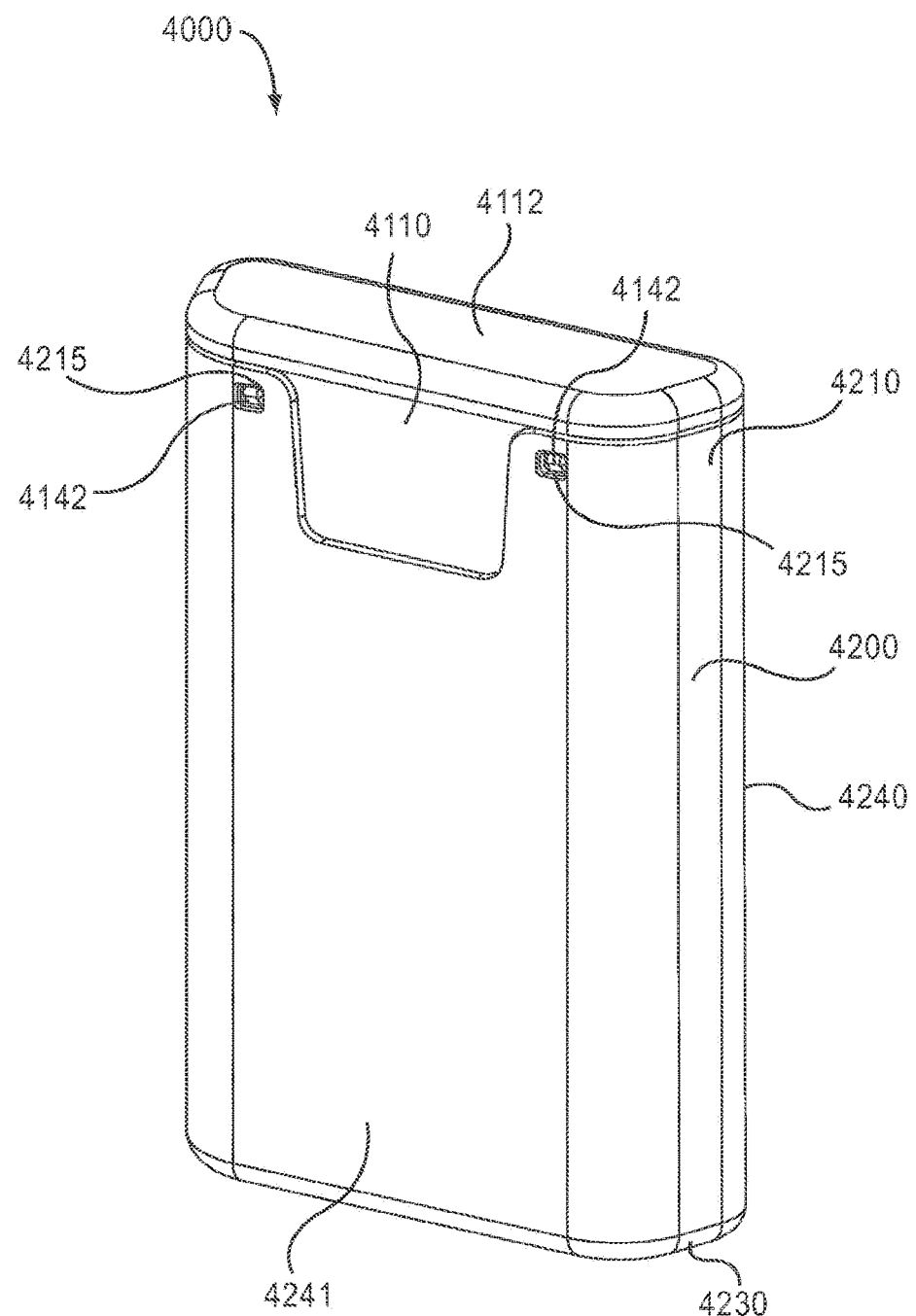
Figure 5:
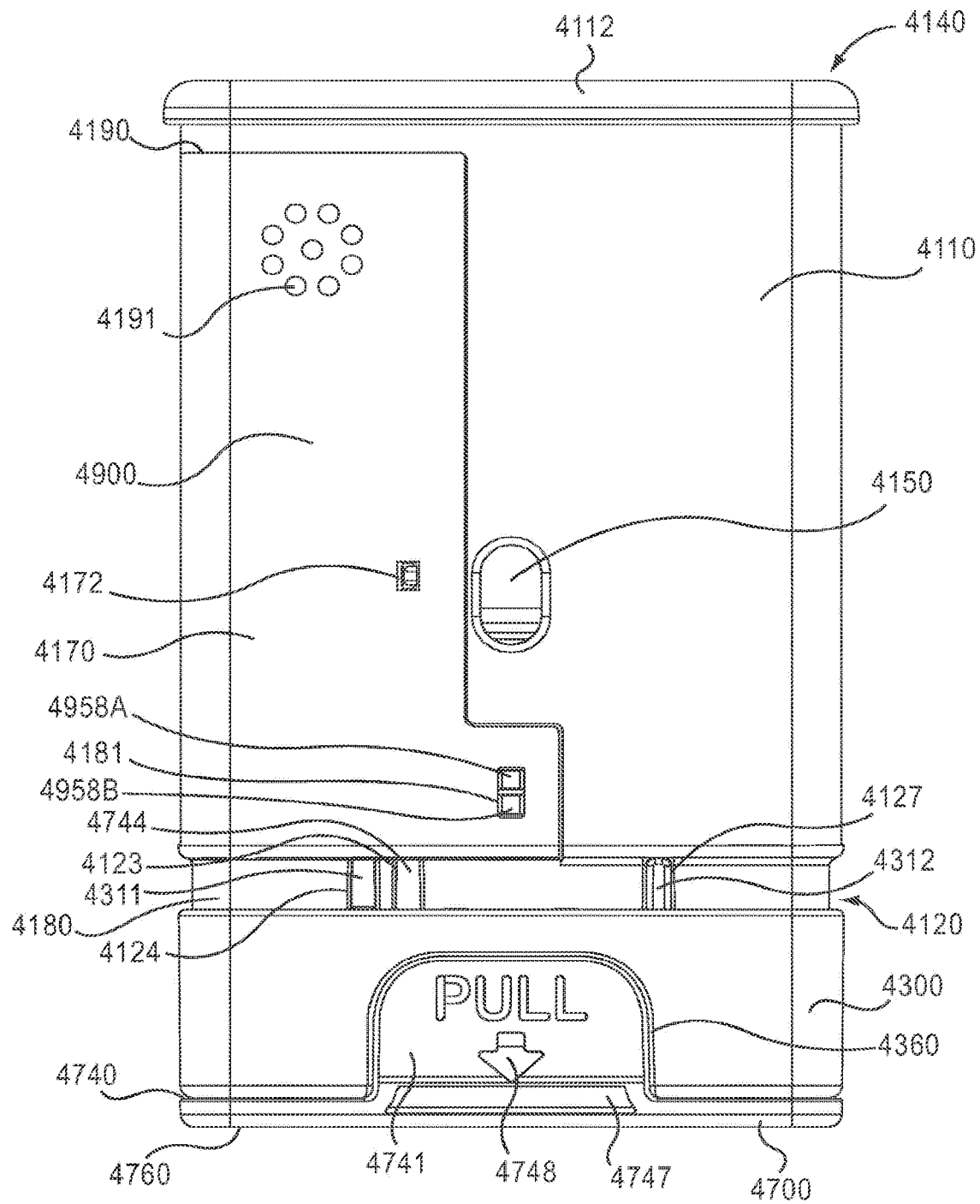
FIGS. 5 and 6 are a front view and a back view, respectively, of the medical injector illustrated in FIG. 3 with the cover removed.

FIGS. 3-34 show a medical injector 4000 as another example of a delivery device that can be used in conjunction with and/or as a part of the delivery systems and methods described herein. FIGS. 3-4 are perspective views of the medical injector 4000 in a first configuration (i.e., prior to use). The medical injector 4000 includes a housing 4110, a delivery mechanism 4500 (see e.g., FIG. 12), an electronic circuit system 4900 (see e.g., FIGS. 13-23), a cover 4200 (see e.g., FIGS. 24-25), a safety lock 4700 (see e.g., FIGS. 26-29) and a base 4300 (see e.g., FIGS. 30-31). A discussion of the components of the medical injector 4000 will be followed by a discussion of the operation of the medical injector 4000.

As shown in FIGS. 5-11, the housing 4110 has a proximal end portion 4140 and a distal end portion 4120. The housing 4110 defines a first status indicator aperture 4150 and a second status indicator aperture 4151. The first status indicator aperture 4150 defined by the housing 4110 is located on a first side of the housing 4110, and the second status indicator aperture 4151 of the housing 4110 is located on a second side of the housing 4110. The status indicator apertures 4150, 4151 can allow a patient to monitor the status and/or contents of a medicament container 4560. For example, by visually inspecting the status indicator apertures 4150, 4151, a patient can determine whether the medicament container 4560 contains a medicament and/or whether a medicament has been dispensed.

Figure 9:
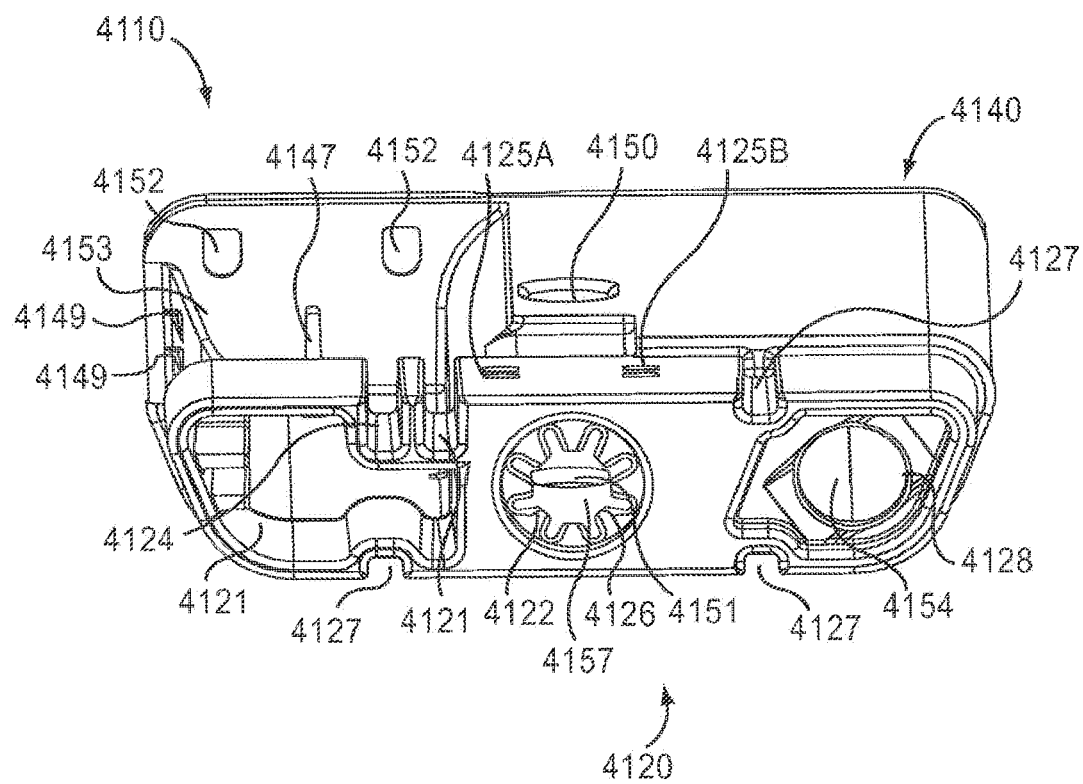
FIG. 9 is a bottom perspective view of a housing of the medical injector illustrated in FIG. 3.
Figure 10:
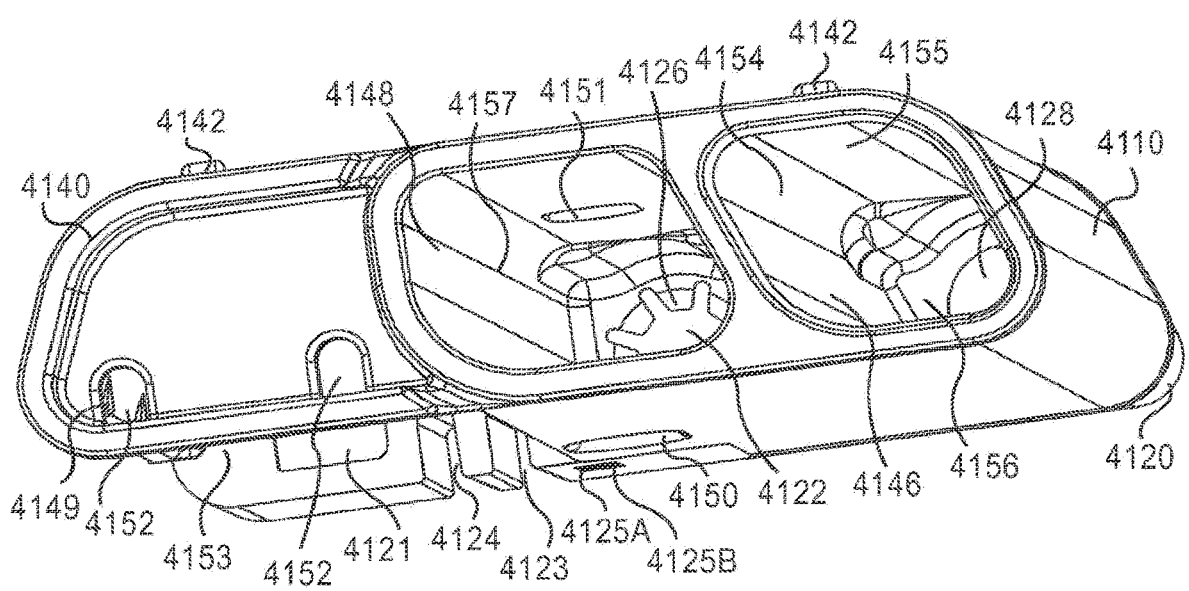
FIGS. 10 and 11 are perspective views of a housing and a proximal cap of the housing, respectively, of the medical injector illustrated in FIG. 3.

As shown in FIGS. 9 and 10, the housing 4110 defines a gas cavity 4154, a medicament cavity 4157 and an electronic circuit system cavity 4153. The gas cavity 4154 has a proximal end portion 4155 and a distal end portion 4156. The gas cavity 4154 is configured to receive the gas container 4570 and the release member 4540 of the medicament delivery mechanism 4500 (see e.g., FIG. 12) as described in further detail herein. The proximal end portion 4155 of the gas cavity 4154 is configured to receive the gas container retention member 4580 of the proximal cap 4112 of the housing 4110, as described in further detail herein. The gas cavity 4154 is in fluid communication with the medicament cavity 4157 via a gas passageway 4144, as described in further detail herein, and the gas cavity 4154 is in fluid communication with a region outside the housing 4110 via a safety lock aperture 4128.

The medicament cavity 4157 is configured to receive a portion of the delivery mechanism 4500. In particular, the carrier 4520, the moveable member 4530 and the needle 4512 of the medicament delivery mechanism 4500 are movably disposed in the medicament cavity 4157. The medicament cavity 4157 is in fluid communication with a region outside the housing 4110 via a needle aperture 4122.

The electronic circuit system cavity 4153 is configured to receive the electronic circuit system 4900. The housing 4110 has protrusions 4149 (see e.g., FIG. 8) configured to stabilize the electronic circuit system 4900 when the electronic circuit system 4900 is disposed within the electronic circuit system cavity 4153. The housing 4110 also defines connection apertures 4152 configured to receive connection protrusions 4171 of the electronic circuit system 4900, and aperture 4145 (see e.g., FIG. 6) configured to receive a portion of a protrusion 4174 of the electronic circuit system 4900. In this manner, the electronic circuit system 4900 can be coupled to the housing 4110 within the electronic circuit system cavity 4153. In other embodiments, the electronic circuit system 4900 can be coupled within the electronic circuit system cavity 4153 by other suitable means such as an adhesive, a clip and/or the like.

The electronic circuit system cavity 4153 is fluidically and/or physically isolated from the gas cavity 4154 and/or the medicament cavity 4157 by a sidewall 4148. The sidewall 4148 can be any suitable structure to isolate the electronic circuit system cavity 4153 within the housing 4110 from the gas cavity 4154 and/or the medicament cavity 4157 within the housing 4110. Similarly, the gas cavity 4154 and the medicament cavity 4157 are separated by a sidewall 4146. In some embodiments, sidewall 4146 can be similar to the sidewall 4148, which isolates the gas cavity 4154 and the medicament cavity 4157 from the electronic circuit system cavity 4153. In other embodiments the gas cavity 4154 can be fluidically and/or physically isolated from the medicament cavity 4157.

Figure 6:
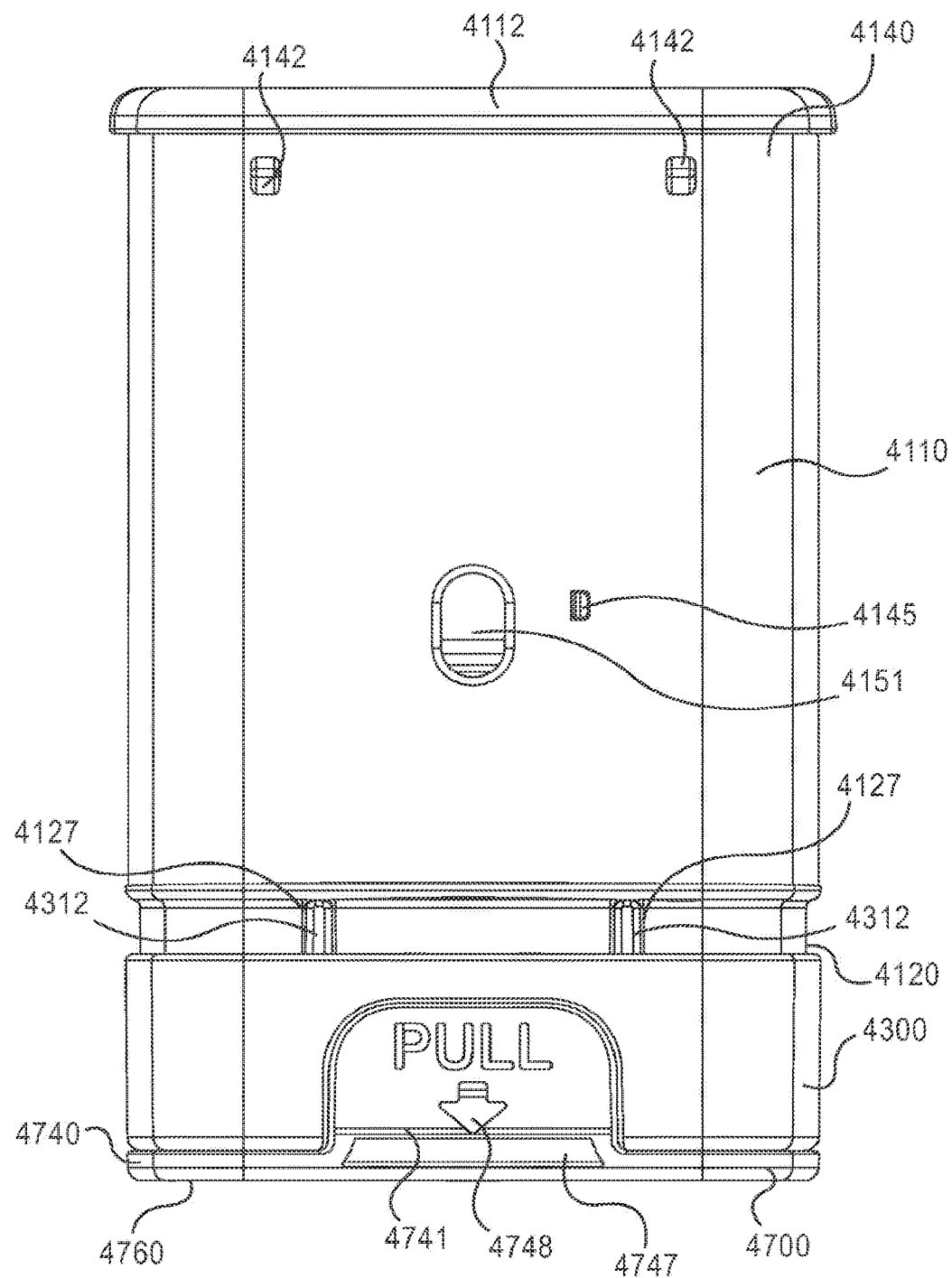

The proximal end portion 4140 of the housing 4110 includes a proximal cap 4112, a speaker protrusion 4147 (see e.g., FIGS. 8 and 9), and cover retention protrusions 4142 (see e.g., FIGS. 4 and 6). The speaker protrusion 4147 is configured to maintain a position of an audio output device 4956 of the electronic circuit system 4900 relative to the housing 4110 when the electronic circuit system 4900 is attached to the housing 4110, as described herein. Cover retention protrusions 4142 are configured to be received within corresponding openings 4215 on the cover 4200. In this manner, as described in more detail herein, the cover 4200 can be removably coupled to and disposed about at least a portion of the housing 4110.

Figure 11:
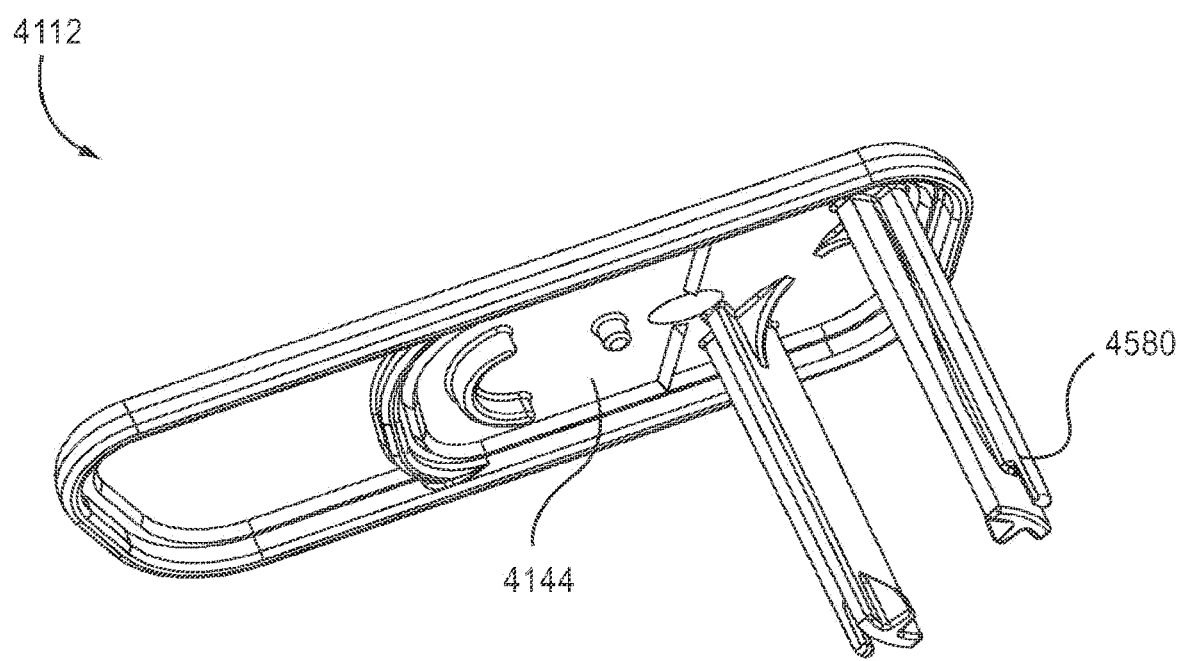

As shown in FIG. 11, the proximal cap 4112 includes a gas container retention member 4580 and defines a gas passageway 4144. The gas container retention member 4580 is configured to receive and/or retain a gas container 4570 that can contain a pressurized gas. The gas passageway 4144 is configured to allow for the passage of gas contained in the gas container 4570 from the gas cavity 4154 to the medicament cavity 4157, as further described herein. Said another way, the gas passageway 4144 places the gas cavity 4154 in fluid communication with the medicament cavity 4157.

Figure 7:
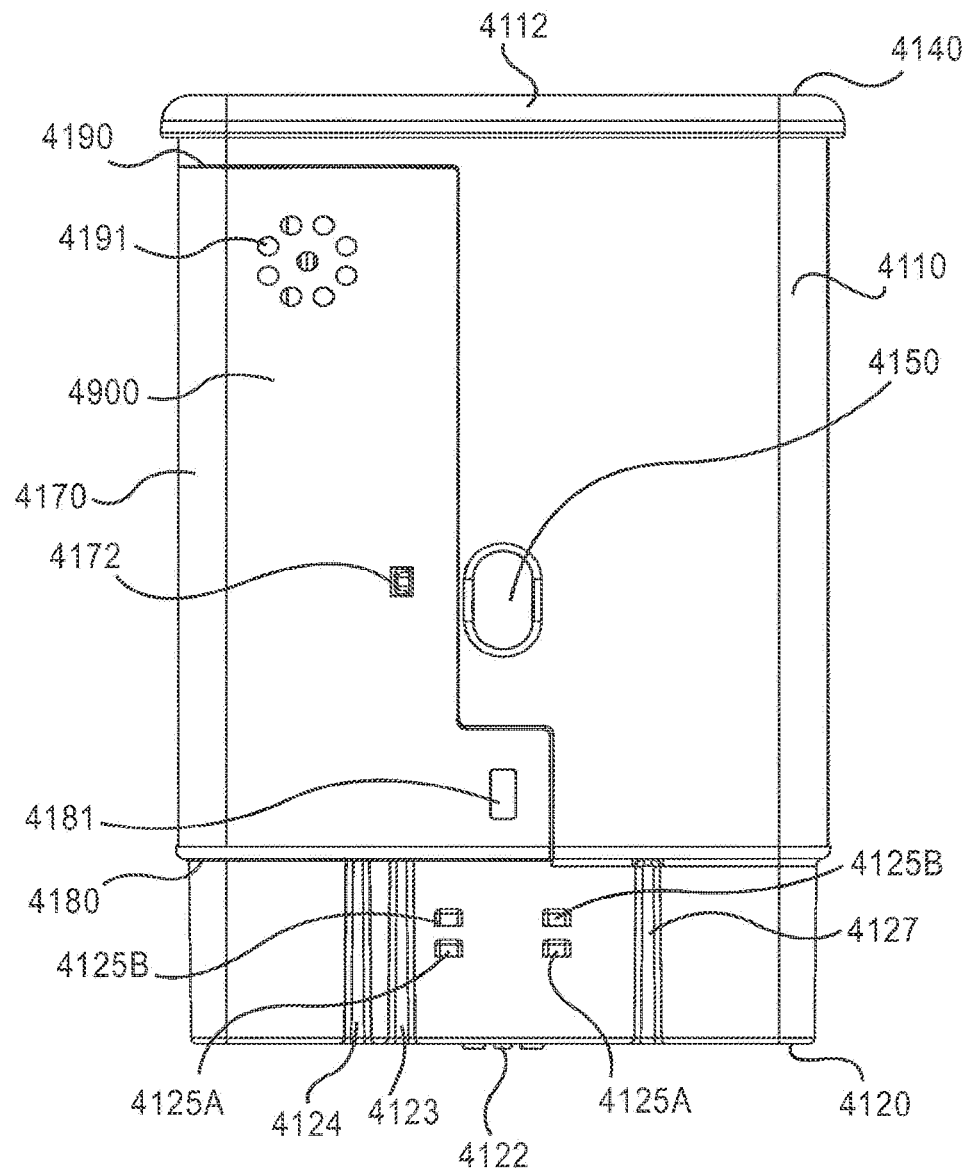
FIG. 7 is a front view of a portion of the medical injector illustrated in FIG. 3.
Figure 8:
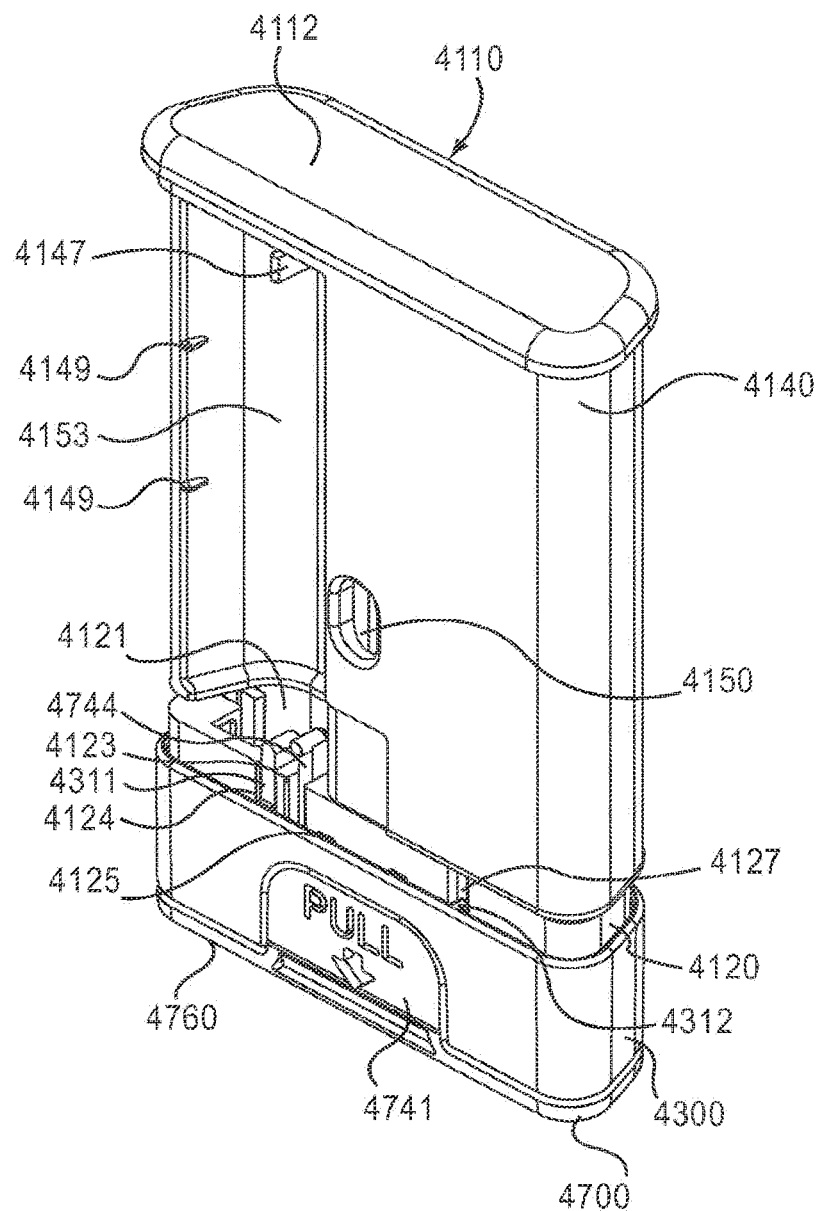
FIG. 8 is a perspective view of a portion of the medical injector illustrated in FIG. 3.

As shown in FIGS. 7 and 9, the distal end portion 4120 of the housing 4110 defines a battery isolation protrusion aperture 4121, a needle aperture 4122, a safety lock actuator groove 4123, a safety lock aperture 4128, a base actuator groove 4124, base retention recesses 4125A, 4125B, and base rail grooves 4127. The battery isolation protrusion aperture 4121 is configured to receive the battery isolation protrusion 4235 of the cover 4200 (see e.g., FIG. 25), as described in further detail herein.

The needle aperture 4122 is configured to allow the needle 4512 (see e.g., FIG. 12) to exit the housing 4110 when the medical injector 4000 is actuated. The portion of the sidewall of the housing 4110 that defines the needle aperture 4122 includes multiple sheath retention protrusions 4126. In some embodiments, the sheath retention protrusions can interact with a plurality of ribs 4728 of the needle sheath 4720 (see e.g. FIG. 29) to maintain a position of the needle sheath 4720 relative to the safety lock 4700 when the safety lock 4700 is coupled to the housing 4110 and/or when the safety lock 4700 is being removed from the housing 4110.

The safety lock actuator groove 4123 is configured to receive an actuator 4744 of the safety lock 4700. As described in more detail herein, the actuator 4744 is configured to engage and/or activate the electronic circuit system 4900 when the safety lock 4700 is moved with respect to the housing 4110. The safety lock aperture 4128 is configured to receive a safety lock protrusion 4742 (see e.g., FIGS. 25 and 26). As described in more detail below, the safety lock protrusion 4742 is received within an opening 4554 between extensions 4552 of a release member 4540 such that activation of the medical injector 4000 is prevented when the safety lock 4700 is in place. The safety lock 4700, its components and functions are further described herein.

The distal base retention recesses 4125A are configured to receive the base connection knobs 4358 of the base 4300 (see e.g., FIG. 30) when the base 4300 is in a first position relative to the housing 4110. The proximal base retention recesses 4125B are configured to receive the base connection knobs 4358 of the base 4300 when the base 4300 is in a second position relative to the housing 4110. The base retention recesses 4125A, 4125B have a tapered proximal sidewall and a non-tapered distal sidewall. This allows the base retention recesses 4125A, 4125B to receive the base connection knobs 4358 such that the base 4300 can move proximally relative to the housing 4110, but cannot move distally relative to the housing 4110. Said another way, the distal base retention recesses 4125A are configured to prevent the base 4300 from moving distally when the base 4300 is in a first position and the proximal base retention recesses 4125B are configured to prevent the base 4300 from moving distally when the base 4300 is in a second position. Similarly stated, the proximal base retention recesses 4125B and the base connection knobs 4358 cooperatively prevent "kickback" after the medical injector 4000 is actuated.

The base actuator groove 4124 is configured to receive an actuator 4311 of the base 4300. As described in more detail herein, the actuator 4311 of the base 4300 is configured to engage the electronic circuit system 4900 when the base 4100 is moved with respect to the housing 4110. The base rail grooves 4127 are configured to receive the guide members 4312 of the base 4300. The guide members 4312 of the base 4300 and the base rail grooves 4127 of the housing 4110 engage each other in a way that allows the guide members 4312 of the base 4300 to slide in a proximal and/or distal direction within the base rail grooves 4127 while limiting lateral movement of the guide members 4312. This arrangement allows the base 4300 to move in a proximal and/or distal direction with respect to the housing 4110 but prevents the base 4300 from moving in a lateral direction with respect to the housing 4110.

Figure 12:
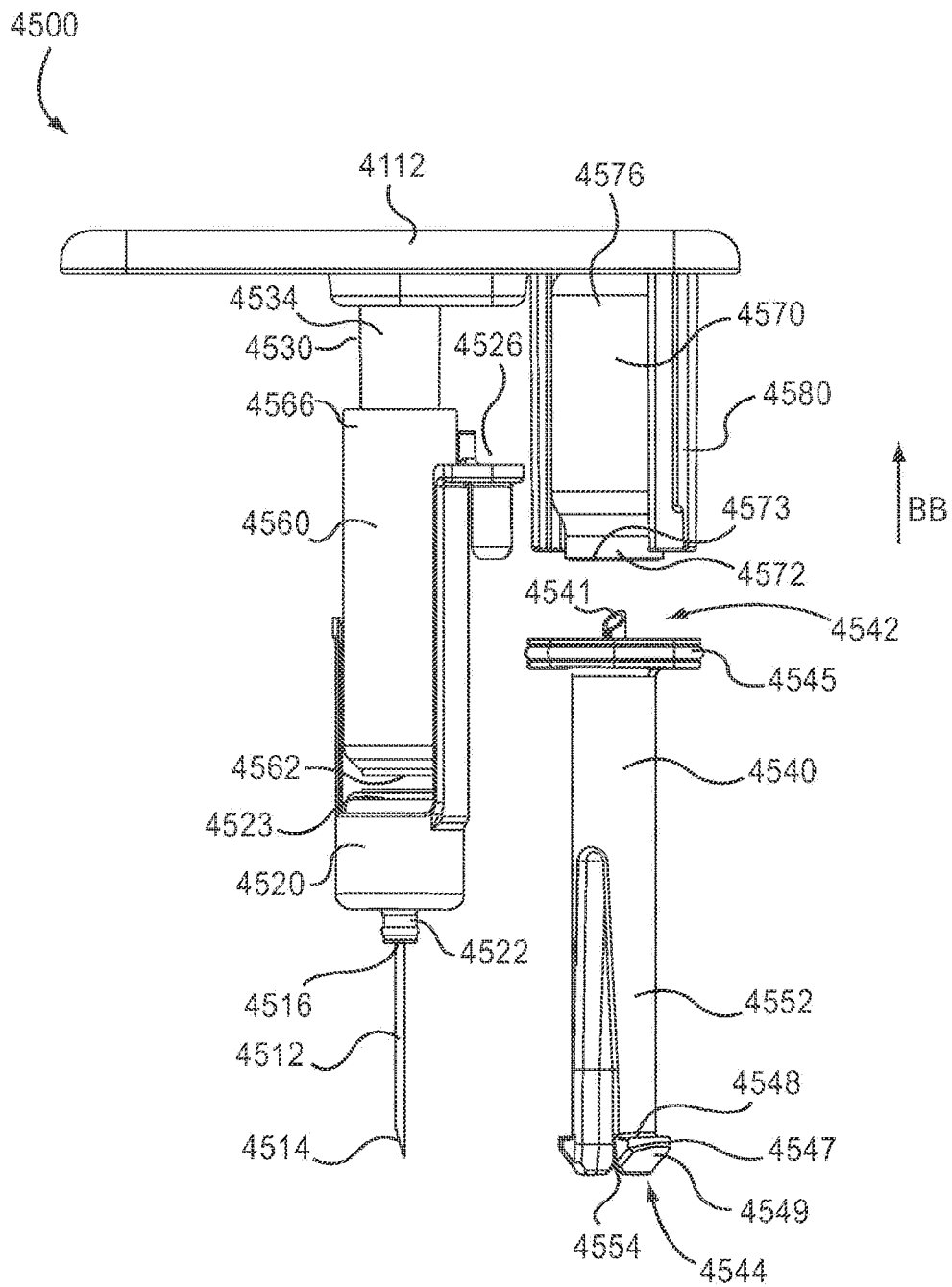
FIG. 12 is a front view of a medicament delivery mechanism of the medical injector illustrated in FIG. 3.
Figure 13:
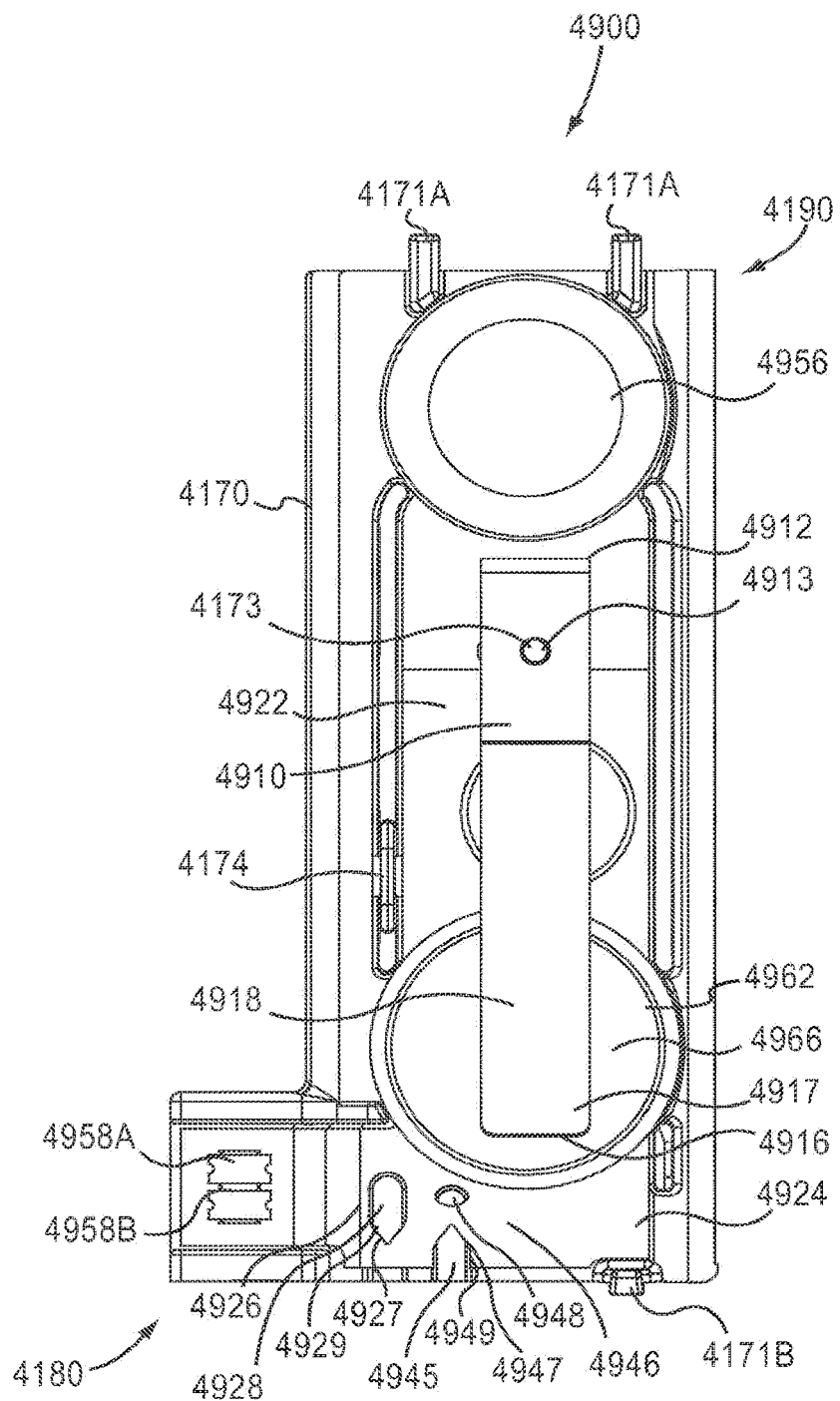
FIGS. 13 and 14 are a back view and a front view, respectively, of an electronic circuit system of the medical injector illustrated in FIG. 3.
Figure 14:
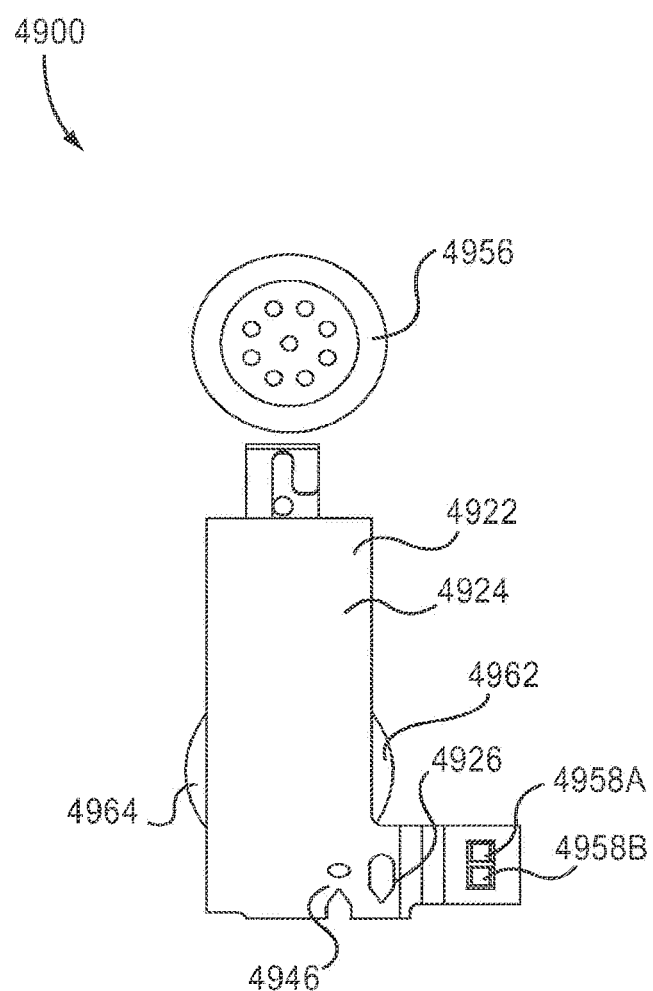
Figure 15:
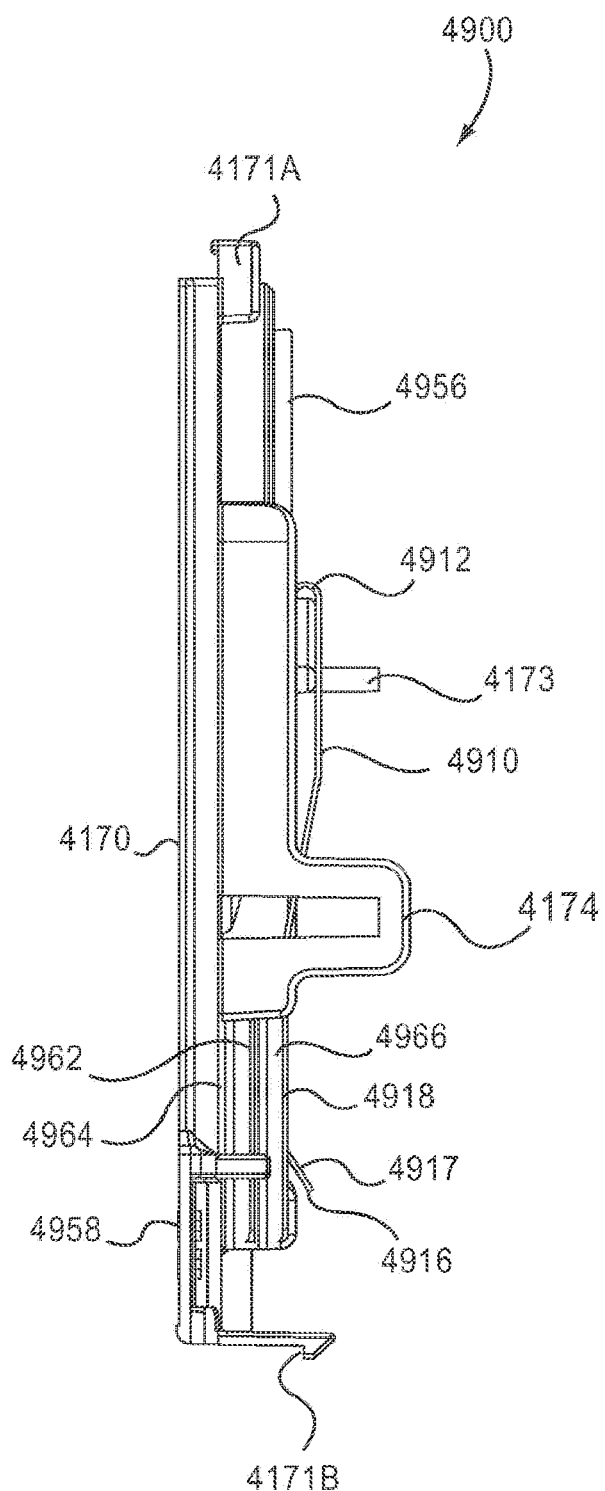
FIG. 15 is a side view of the electronic circuit system of the medical injector illustrated in FIG. 13.

FIG. 12 shows the medicament delivery mechanism 4500 of the medical injector 4000. The medical injector 4000 is similar to the auto-injectors described in U.S. Pat. No. 7,648,482, entitled "Devices, Systems and Methods for Medicament Delivery," filed Nov. 21, 2006, which is incorporated herein by reference in its entirety. Accordingly, only an overview of the medicament delivery mechanism 4500 and related operation of the medical injector 4000 is included below.

The medicament delivery mechanism 4500 includes a needle 4512, a carrier 4520, a movable member 4530, a medicament container 4560, a gas container 4570, and a release member 4540. As described above, the needle 4512, carrier 4520, movable member 4530 and medicament container 4560 are disposed within the medicament cavity 4157 of the housing 4110. The gas container 4570 and the release member 4540 are disposed within the gas cavity 4154 of the housing 4110.

The release member 4540 has a proximal end portion 4542 and a distal end portion 4544, and is movably disposed within the distal end portion 4156 of the gas cavity 4154. The proximal end portion 4542 of the release member 4540 includes a sealing member 4545 and a puncturer 4541. The sealing member 4545 is configured to engage the sidewall of the housing 4110 defining the gas cavity 4154 such that the proximal end portion 4155 of the gas cavity 4154 is fluidically isolated from the distal end portion 4156 of the gas cavity 4154. In this manner, when gas is released from the gas container 4570, the gas contained in the proximal end portion 4155 of the gas cavity 4154 is unable to enter the distal end portion 4156 of the gas cavity 4154. The puncturer 4541 of the proximal end portion 4542 of the release member 4540 is configured to contact and puncture a frangible seal 4573 on the gas container 4570 when the release member 4540 moves proximally within the gas cavity 4154, as shown by the arrow BB in FIG. 12.

The distal end portion 4544 of the release member 4540 includes extensions 4552. The extensions 4552 include projections 4547 that include tapered surfaces 4549 and engagement surfaces 4548. Further, the extensions 4552 define an opening 4554 between the extensions 4552. The tapered surfaces 4549 of the projections 4547 are configured to contact protrusions 4313 on a proximal surface 4310 of the base 4300 (see e.g., FIG. 30). The engagement surfaces 4548 of the projections 4547 are configured to extend through the safety lock aperture 4128 of the housing 4110 and contact a distal surface of the housing 4110. In this manner, the engagement surfaces 4548 of the projections 4547 limit proximal movement of the release member 4540 when the engagement surfaces 4548 are in contact with the distal surface of the housing 4110.

Figure 27:
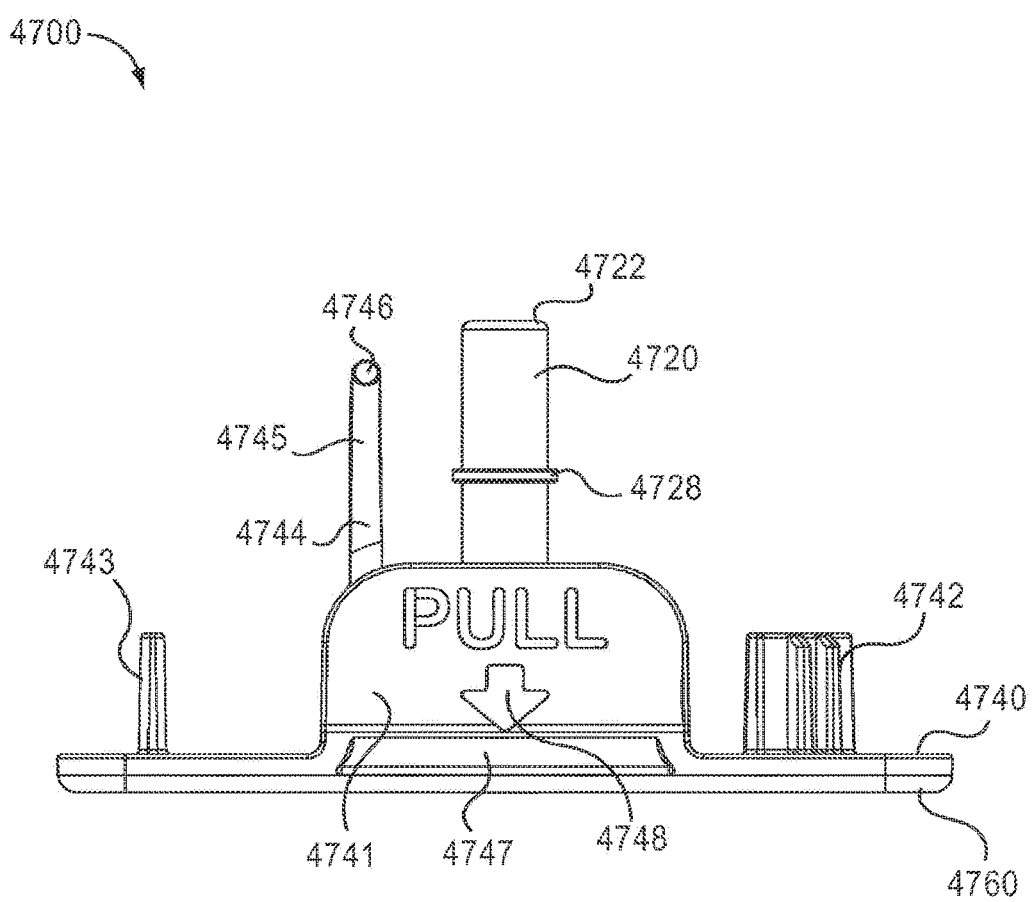

The opening 4554 defined by the extensions 4552 is configured to receive the safety lock protrusion 4742 of the safety lock 4700 (see e.g., FIG. 27). The safety lock protrusion 4742 is configured to prevent the extensions 4552 from moving closer to each other. Said another way, the safety lock protrusion 4742 is configured to ensure that the extensions 4552 remain apart and the engagement surfaces 4548 of the projections 4547 remain in contact with the distal end portion 4120 of the housing 4110. In some embodiments, for example, the release member 4540 and/or the extensions 4552 can be constructed from any suitable material configured to withstand deformation that may occur when exposed to a load over an extended period of time. In some embodiments, for example, the release member 4540 and/or the extensions 4552 can be constructed from brass.

The gas container 4570 includes a distal end portion 4572 and a proximal end portion 4576, and is configured to contain a pressurized gas. The distal end portion 4572 of the gas container 4570 contains a frangible seal 4573 configured to break when the puncturer 4541 of the proximal end portion 4542 of the release member 4540 contacts the frangible seal 4573. The gas container retention member 4580 of the proximal cap 4112 of the housing 4110 is configured to receive and/or retain the proximal end portion 4576 of the gas container 4570. Said another way, the position of the gas container 4570 within the gas cavity 4154 is maintained by the gas container retention member 4580.

The medicament container 4560 of the medicament delivery mechanism 4500 has a distal end portion 4562 and a proximal end portion 4566, and is configured to contain a medicament. The distal end portion 4562 of the medicament container 4560 contains a seal 4523. The seal 4523 is configured to burst when punctured by the proximal end 4516 of the needle 4512, as described below. The proximal end portion 4566 of the medicament container 4560 is configured to receive a piston portion 4534 of the movable member 4530.

The movable member 4530 of the medicament delivery mechanism 4500 is movably disposed within the medicament cavity 4157. The movable member 4530 includes a piston portion 4534 having a plunger at the distal end portion of the piston portion 4534. The piston portion 4534 is configured to move within the medicament container 4560. In this manner, the piston portion 4534 of the movable member 4530 can apply pressure to a medicament contained in the medicament container 4560. The piston portion 4534 can be constructed of a resilient, durable, and/or sealing material, such as a rubber.

The carrier 4520 of the medicament delivery mechanism 4500 includes a distal end portion 4522 and a proximal end portion 4526. The medicament container 4560 is coupled to the carrier 4520 via a "snap-fit" connection (not shown) such that the medicament container 4560 can move relative to the carrier 4520 between a first configuration and a second configuration during an injection event. In the first configuration, the carrier 4520 is configured to move within the medicament cavity 4157 such that movement of the carrier 4520 within the medicament cavity 4157 causes contemporaneous movement of the medicament container 4560 within the medicament cavity 4157. The proximal end portion 4516 of the needle 4512 is spaced apart from the seal 4523 of the medicament container 4560 when the carrier 4520 is in the first configuration. In the second configuration, the medicament container 4560 releases from the "snap-fit" causing the medicament container 4560 to move distally with respect to the carrier 4520, causing the proximal end portion 4516 of the needle 4512 to pierce the seal 4523. In this manner, the needle 4512 can be selectively placed in fluid communication with the medicament container 4560 to define a medicament delivery path (not shown).

Figure 20:
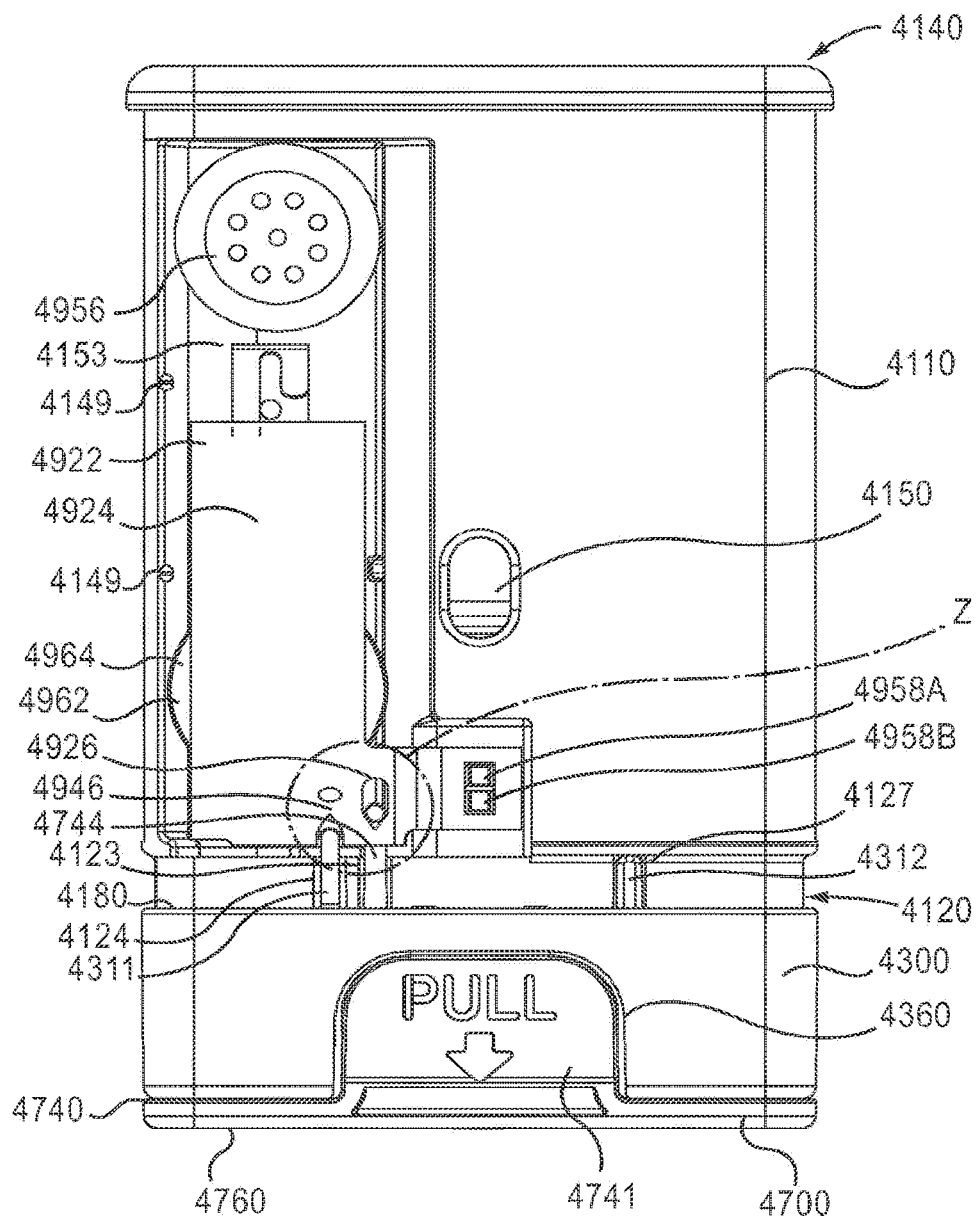
FIG. 20 is a front view of the medical injector illustrated in FIG. 3 in a first configuration showing the electronic circuit system.

FIGS. 13-22 show the electronic circuit system 4900. The electronic circuit system 4900 of the medical injector 4000 includes an electronic circuit system housing 4170, a printed circuit board 4922, a battery assembly 4962, an audio output device 4956, two light emitting diodes (LEDs) 4958A, 4958B and a battery clip 4910. As shown in FIG. 20, the electronic circuit system 4900 is configured to fit within the electronic circuit system cavity 4153 of the housing 4110. Accordingly, as described above, the electronic circuit system 4900 is physically and/or fluidically isolated from the medicament cavity 4157, the gas cavity 4154 and/or the medicament delivery device 4500. As described herein, the electronic circuit system 4900 is configured to output an electronic output associated with the use of the medical injector 4000.

The electronic circuit system housing 4170 of the electronic circuit system 4900 includes a distal end portion 4180 and a proximal end portion 4190. The proximal end portion 4190 includes connection protrusions 4171A and a battery clip protrusion 4173. The connection protrusions 4171A extend from the proximal end portion 4190 of the electronic circuit system housing 4170, and are configured to be disposed within the connection apertures 4152 of the housing 4110, as described above. In this manner, the electronic circuit system 4900 can be coupled to the housing 4110 within the electronic circuit system cavity 4153. In other embodiments, the electronic circuit system 4900 can be coupled to the housing 4110 by other suitable means such as an adhesive, a clip and/or the like. As described in more detail herein, the battery clip protrusion 4173 is configured to hold the battery clip 4910 in place.

The proximal end portion 4190 of the electronic circuit system housing 4170 defines multiple sound apertures 4191. The audible output device 4956 is disposed against the proximal end portion 4190 of the electronic circuit system housing 4170 such that the front face of the audible output device 4956 is disposed adjacent the sound apertures 4191. In this manner, the sound apertures 4191 are configured to allow sound from an audio output device 4956 to pass from the audio output device 4956 to a region outside of the housing 4110.

Figure 16:
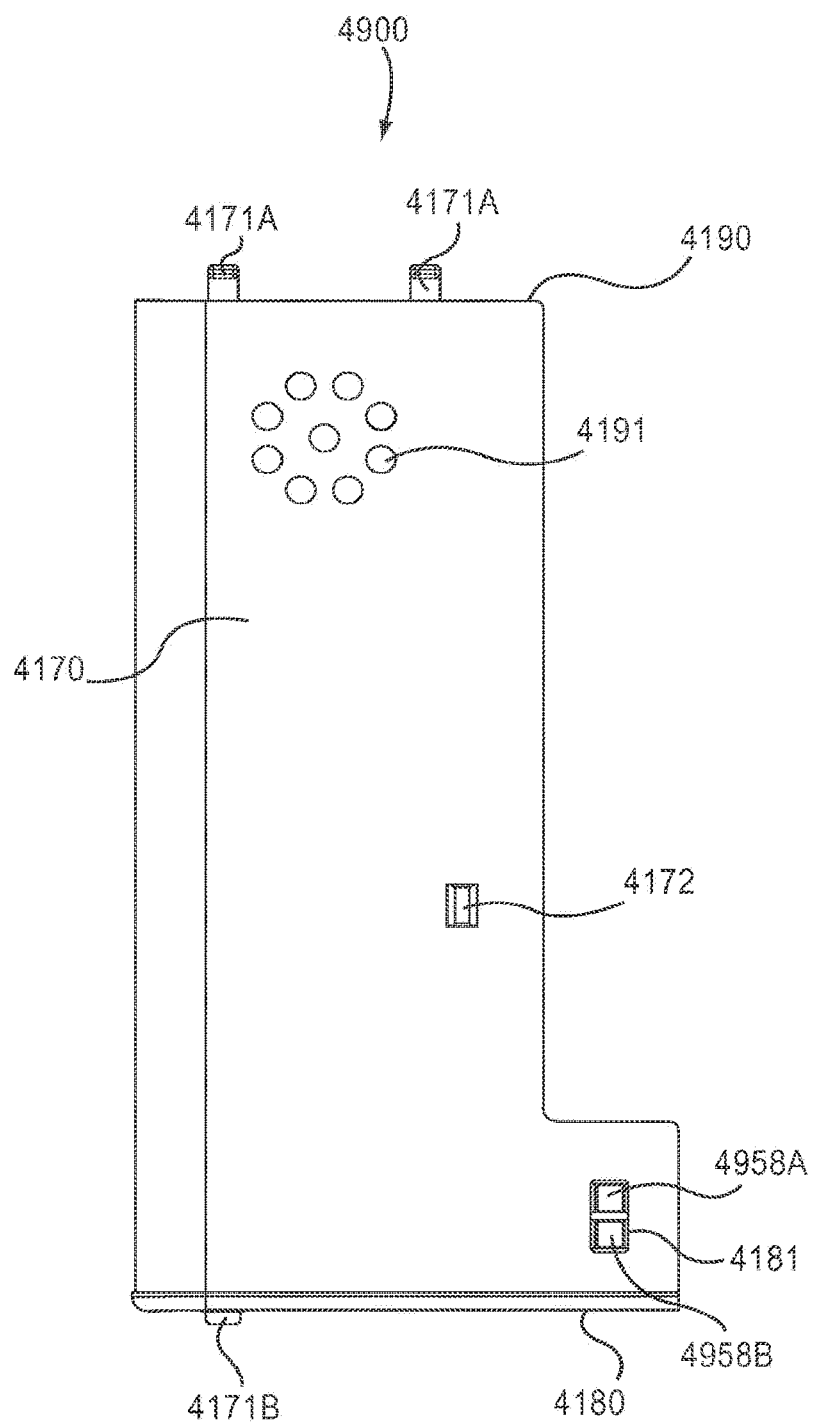
FIGS. 16 and 17 are a front view and a perspective view, respectively, of an electronic circuit system housing of the medical injector illustrated in FIG. 13.
Figure 17:
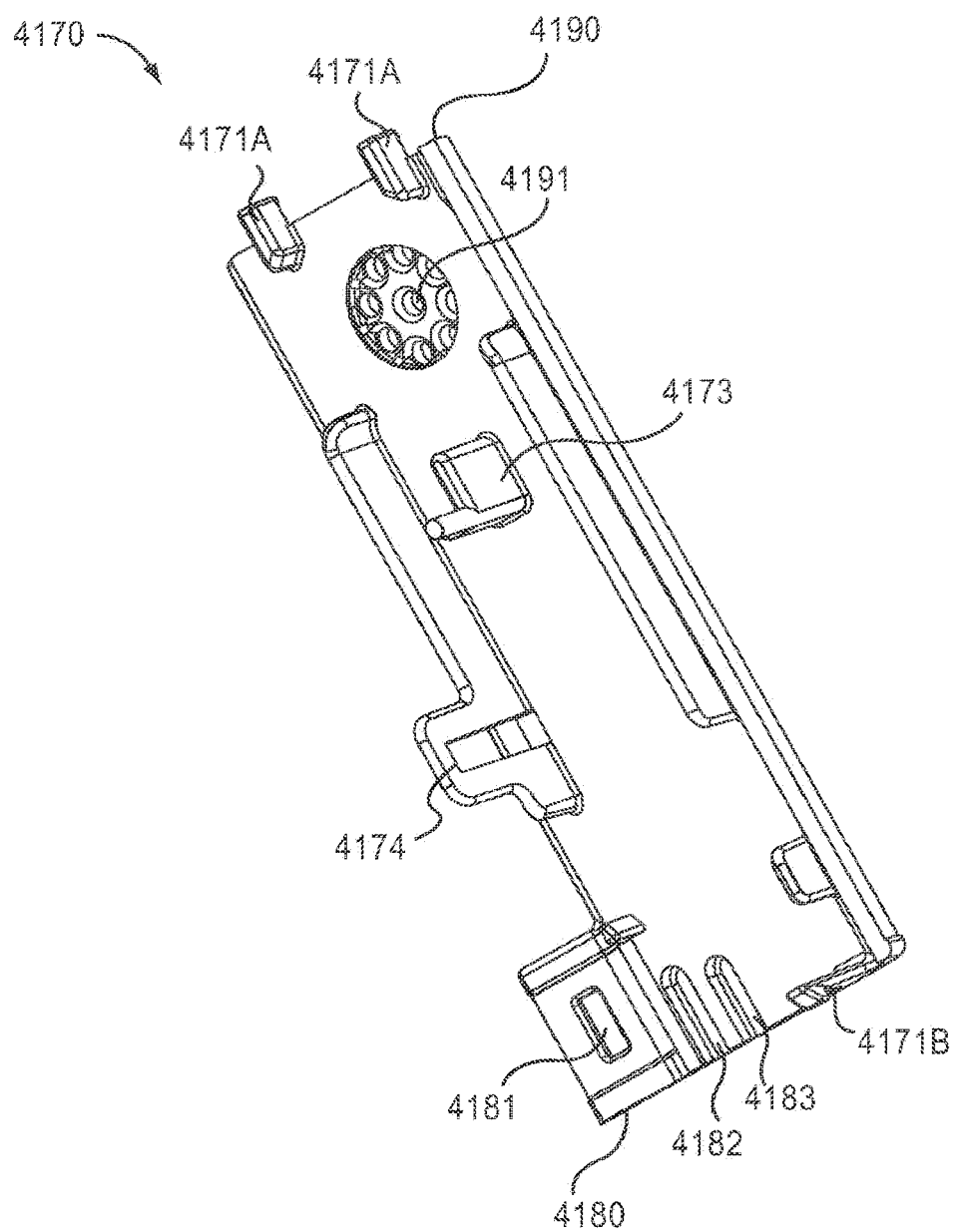
Figure 18:
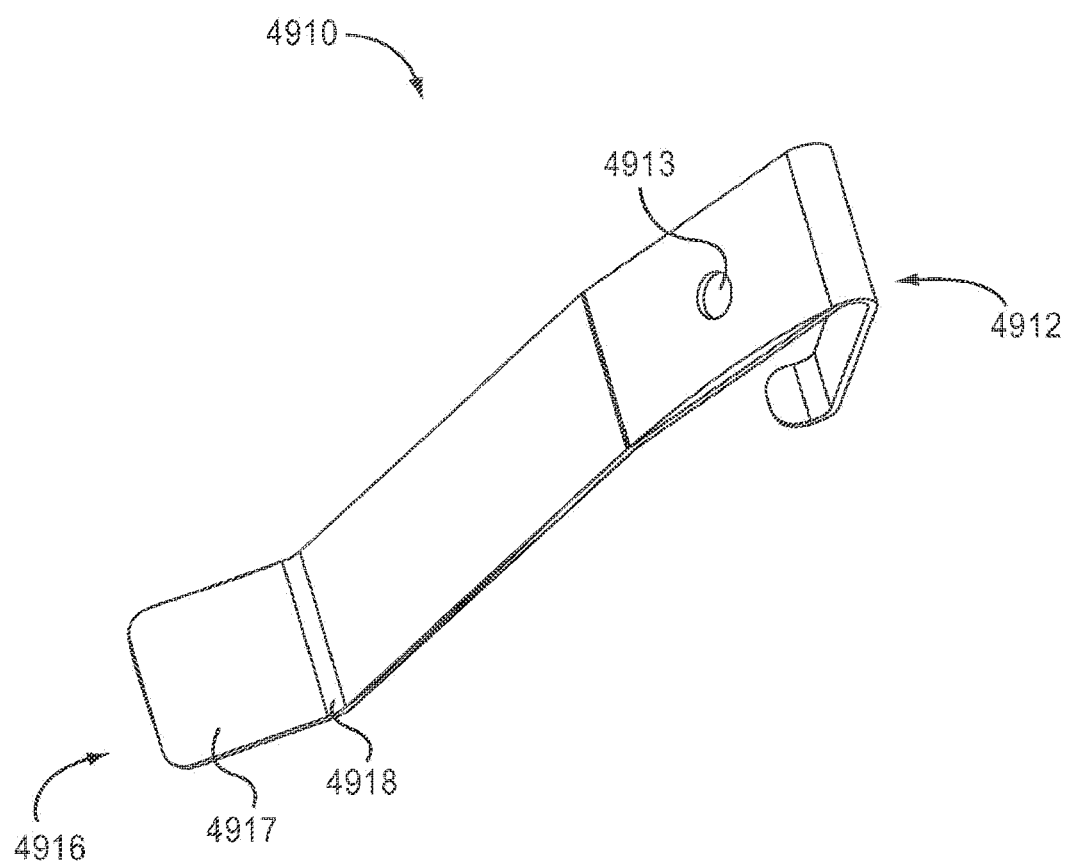
FIG. 18 is a perspective view of a battery clip of the medical injector illustrated in FIG. 13.
Figure 19:
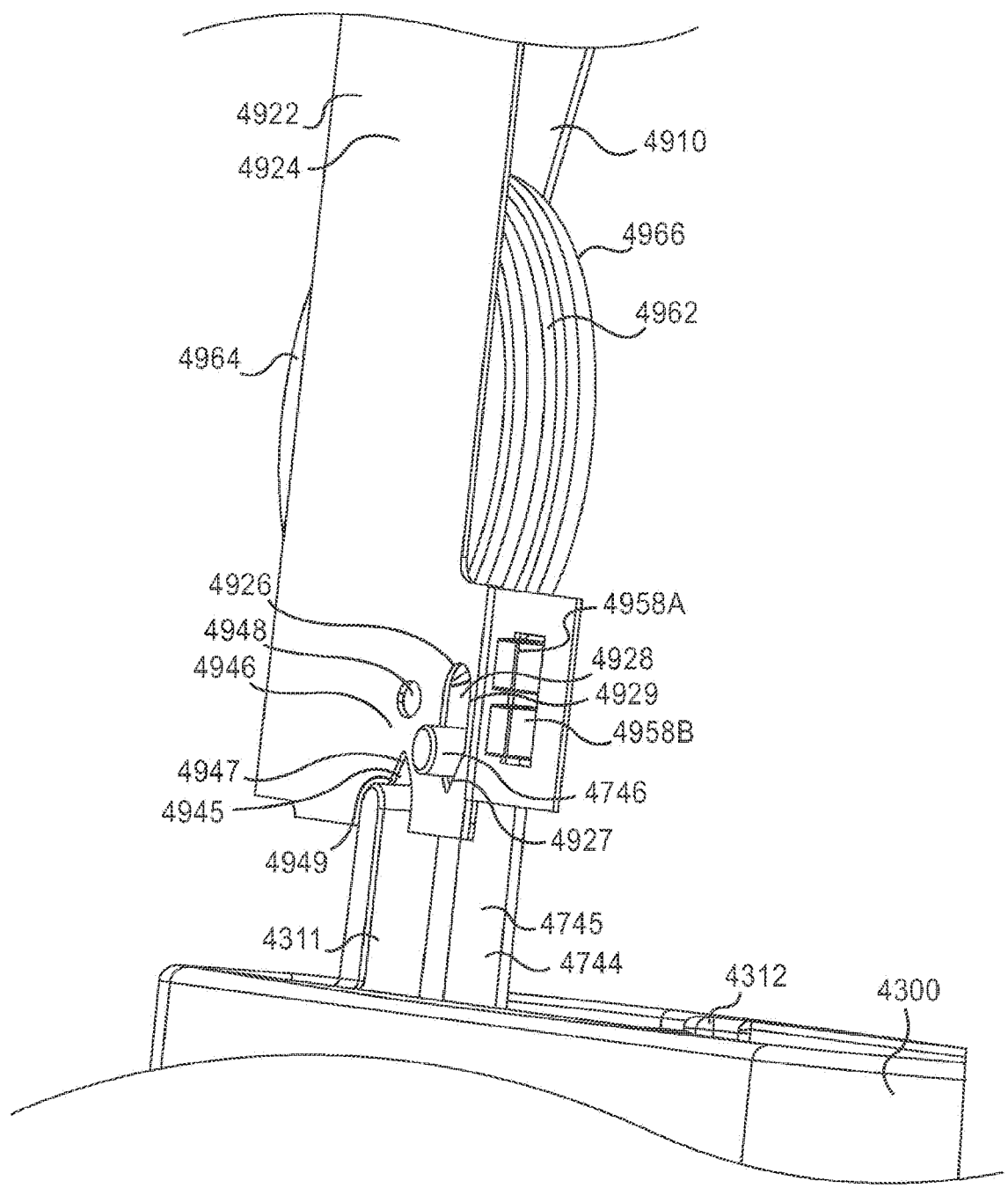
FIG. 19 is a perspective view of a portion of an electronic circuit system of the medical injector illustrated in FIG. 3, in a first configuration.

As shown in FIGS. 16 and 17, the distal end portion 4180 of the electronic circuit system housing 4170 includes a connection protrusion 4171B, a stiffening protrusion 4174, and defines an LED aperture 4181, an aperture 4172, a safety lock actuator groove 4182, and a base actuator groove 4183. The LED aperture 4181 is configured to receive the LEDs 4958A, 4958B such that a user can view the LEDs 4958A, 4958B, which are described in more detail herein.

The connection protrusion 4171B extends from the distal end portion 4180 of the electronic circuit system housing 4170, and is configured to attach the electronic circuit system 4900 to the housing 4110, as described above. The stiffening protrusion 4174 is configured to have at least a portion received within and/or accessible via the aperture 4145 in the housing 4110 (see e.g., FIG. 6). The stiffening protrusion 4174 is configured to limit the bending (e.g., buckling) of the electronic circuit system housing 4170 when the electronic circuit system housing 4170 is coupled to the housing 4110. Moreover, a user can access the stiffening protrusion 4174 via the aperture 4172. In this manner, for example, the user can disengage the stiffening protrusion 4174 from the aperture 4145.

The safety lock actuator groove 4182 of the electronic circuit system housing 4170 is configured to be disposed adjacent the safety lock actuator groove 4123 of the distal end portion 4120 of the housing 4110. In this manner, the safety lock actuator groove 4182 of the electronic circuit system housing 4170 and the safety lock actuator groove 4123 of the distal end portion 4120 of the housing 4110 collectively receive the actuator 4744 of the safety lock 4700, which is described in more detail herein. Similarly, the base actuator groove 4183 of the electronic circuit system housing 4170 is configured to be disposed about the base actuator groove 4124 of the distal end portion 4120 of the housing 4110. The base actuator groove 4183 of the electronic circuit system housing 4170 and the base actuator groove 4124 of the distal end portion 4120 of the housing 4110 collectively receive the actuator 4311 of the base 4300, which is described in more detail herein.

The printed circuit board 4922 of the electronic circuit system 4900 includes a substrate 4924, a first actuation portion 4926 and a second actuation portion 4946. The substrate 4924 of the printed circuit board 4922 includes the electrical components necessary for the electronic circuit system 4900 to operate as desired. For example, the electrical components can be resistors, capacitors, inductors, switches, microcontrollers, microprocessors and/or any of the electronic components described herein.

Figure 21:
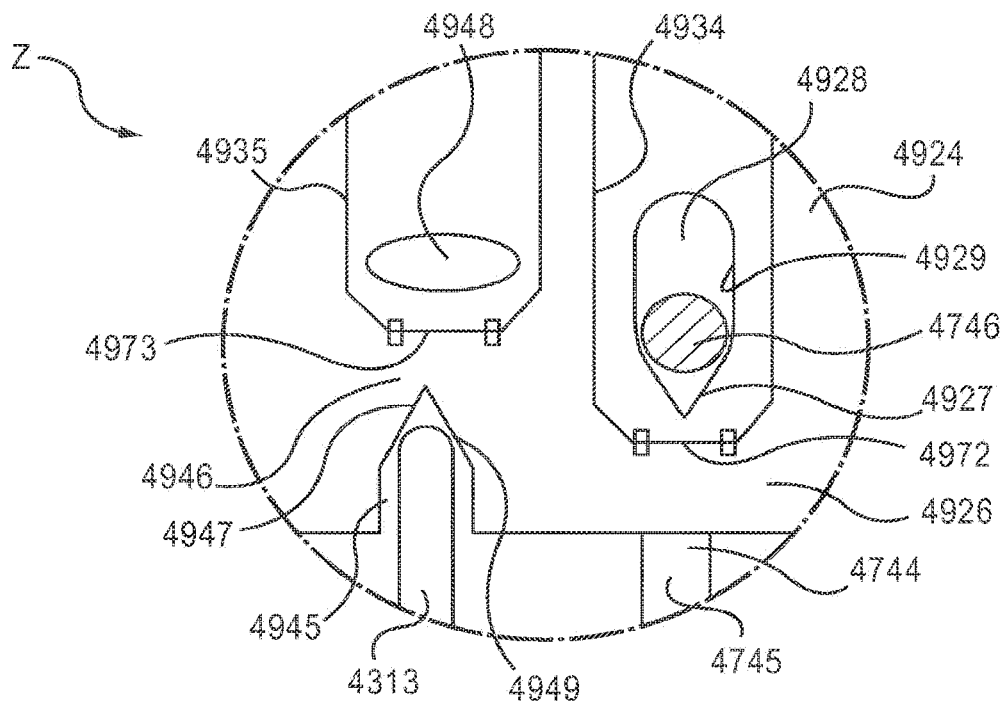
FIGS. 21, 22, and 23 are front views of a portion of the electronic circuit system of the medical injector labeled as Region Z in FIG. 20 in a first configuration, a second configuration, and a third configuration, respectively.
Figure 22:
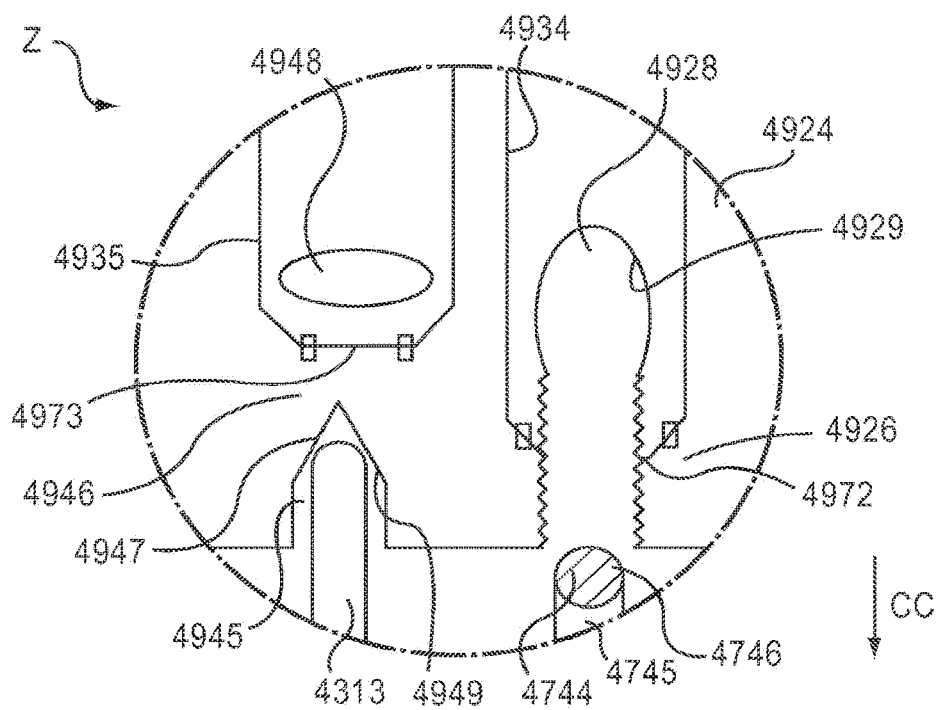
Figure 23:
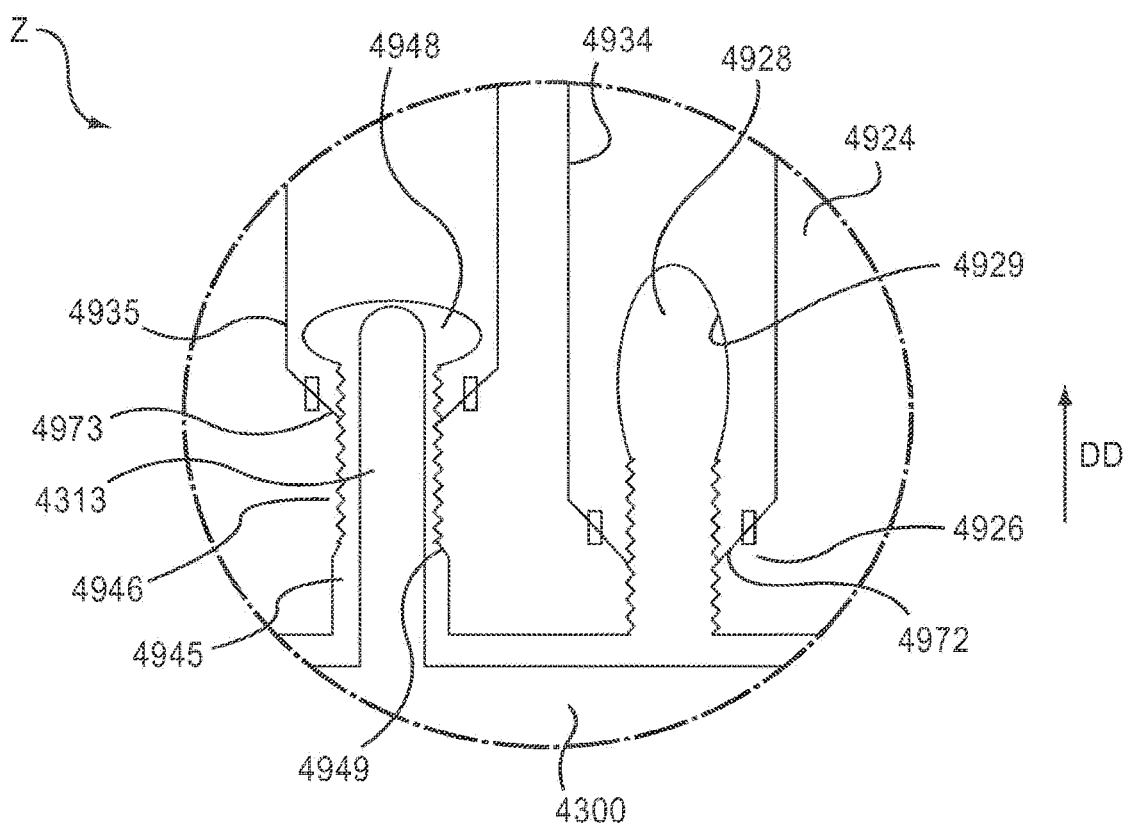

As shown in FIGS. 21-23, the first actuation portion 4926 includes a first electrical conductor 4934 and defines an opening 4928 having a boundary 4929. The opening 4928 of the first actuation portion 4926 is configured to receive a protrusion 4746 of the actuator 4744 of the safety lock 4700. The boundary 4929 of the first opening 4928 has a discontinuous shape, such as, for example, a teardrop shape, that includes a stress concentration riser 4927. The discontinuity and/or the stress concentration riser 4927 of the boundary 4929 can be of any suitable shape to cause the substrate 4924 to deform in a predetermined direction when the protrusion 4746 of the actuator 4744 of the safety lock 4700 is moved relative to the opening 4928, as shown by the arrow CC in FIG. 22.

The opening 4928 is defined adjacent the first electrical conductor 4934 that electronically couples the components included in the electronic circuit system 4900. The first electrical conductor 4934 includes a first switch 4972, which can be, for example a frangible portion of the first electrical conductor 4934. In use, when the safety lock 4700 is moved from a first position (see e.g., FIG. 21) to a second position (see e.g., FIG. 22), the actuator 4744 moves in a direction substantially parallel to a plane defined by a surface of the first actuation portion 4926 of the substrate 4924. The movement of the actuator 4744 causes the protrusion 4746 to move within the first opening 4928, as indicated by the arrow CC in FIG. 22. The movement of the protrusion 4746 tears the first actuation portion 4926 of the substrate 4924, thereby separating the portion of the first electrical conductor 4934 including the first switch 4972. Said another way, when the safety lock 4700 is moved from its first position to its second position (see e.g., FIG. 33), the actuator 4744 moves irreversibly the first switch 4972 from a first state (e.g., a state of electrical continuity) to a second state (e.g., a state of electrical discontinuity). Said yet another way, when the safety lock 4700 is moved from its first position to its second position, the actuator 4744 disrupts the first electrical conductor 4934.

The second actuation portion 4946 includes a second electrical conductor 4935 and defines an opening 4945, having a boundary 4949 and a tear propagation limit aperture 4948. As shown in FIGS. 20-23, the opening 4945 of the second actuation portion 4946 is configured to receive a portion of an actuator 4311 of the base 4300. The boundary 4949 of the opening 4945 has a discontinuous shape that includes a stress concentration riser 4947. The discontinuity and/or the stress concentration riser 4947 of the boundary 4949 can be of any suitable shape to cause the substrate 4924 to deform in a predetermined direction when the actuator 4311 of the base 4300 is moved in a proximal direction relative to the opening 4945, as shown by the arrow DD in FIG. 23.

The second electrical conductor 4935 includes a second switch 4973 disposed between the opening 4945 and the tear propagation limit aperture 4948, which can be, for example, a frangible portion of the second electrical conductor 4935. In use, when the base 4300 is moved from its first position to its second position (see e.g., FIG. 34), the actuator 4311 moves in a proximal direction, substantially parallel to a plane defined by a surface of the second actuation portion 4946 of the substrate 4924. The proximal movement of the actuator 4311 tears the second actuation portion 4946 of the substrate 4924, thereby separating the portion of the second electrical conductor 4935 including the second switch 4973. Said another way, when the base 4300 is moved from its first position to its second position, the actuator 4311 moves irreversibly the second switch 4973 from a first state (e.g., a state of electrical continuity) to a second state (e.g., a state of electrical discontinuity). The tear propagation limit aperture 4948 is configured to limit the propagation of the tear in the substrate 4924 in the proximal direction. Said another way, the tear propagation limit aperture 4948 is configured to ensure that the tear in the substrate 4924 does not extend beyond the tear propagation limit aperture 4948. The tear propagation limit aperture 4948 can be any shape configured to stop the propagation of a tear and/or disruption of the substrate 4924. For example, the tear propagation limit aperture 4948 can be oval shaped. In other embodiments, the proximal boundary of the tear propagation limit aperture 4948 can be reinforced to ensure that the tear in the substrate 4924 does not extend beyond the tear propagation limit aperture 4948.

The battery assembly 4962 of the electronic circuit system 4900 comprises two batteries stacked on top of one another. The battery assembly 4962 has a first surface 4964 and a second surface 4966. The first surface 4964 of the battery assembly 4962 can contact an electrical contact (not shown) disposed on the substrate 4924. The second surface 4966 of the battery assembly 4962 is configured to contact a contact portion 4918 of a distal end portion 4916 of a battery clip 4910. When both the electrical contact of the substrate 4924 and the contact portion 4918 of the distal end portion 4916 of the battery clip 4910 contact the battery assembly 4962, the batteries of the battery assembly 4962 are placed in electrical communication with the electronic circuit system 4900. Said another way, when the electrical contact of the substrate 4924 and the contact portion 4918 of the distal end portion 4916 of the battery clip 4910 contact the battery assembly 4962, the battery assembly 4962 is configured to supply power to the electronic circuit system 4900.

The battery clip 4910 (shown in FIG. 18) includes a proximal end portion 4912 and a distal end portion 4916. The proximal end portion 4912 defines a retention aperture 4913. The retention aperture 4913 is configured to receive the battery clip protrusion 4173 of the electronic circuit system housing 4170. In this manner, the battery clip protrusion 4173 maintains the position of the battery clip 4910 with respect to the electronic circuit system housing 4170 and/or the battery assembly 4962.

The distal end portion 4916 of the battery clip 4910 includes a contact portion 4918 and an angled portion 4917. As described above, the contact portion 4918 is configured to contact the second surface 4916 of the battery assembly 4962 to place the battery assembly 4962 in electrical communication with the electronic circuit system 4900. The angled portion 4917 of the distal end portion 4916 of the battery clip 4910 is configured to allow a proximal end portion 4236 of a battery isolation protrusion 4235 (see e.g., FIG. 25) to be disposed between the second surface 4966 of the battery assembly 4962 and the contact portion 4918 of the distal end portion 4916 of the battery clip 4910. When the battery isolation protrusion 4235 is disposed between the second surface 4966 of the battery assembly 4962 and the contact portion 4918 of the distal end portion 4916 of the battery clip 4910, the electrical path between the battery assembly 4962 and the remainder of the electrical circuit system 4900 is severed, thereby removing power from the electronic circuit system 4900. The contact portion 4918 of the distal end portion 4916 of the battery clip 4910 is biased such that when the battery isolation protrusion 4235 is removed, the contact portion 4918 will move into contact the second surface 4916 of the battery assembly 4962, thereby restoring electrical communication between the battery assembly 4962 and the electronic circuit system 4900. In some embodiments, the battery isolation protrusion 4235 can be repeatedly removed from between the second surface 4966 of the battery assembly 4962 and the contact portion 4918 of the distal end portion 4916 of the battery clip 4910 and reinserted. Said another way, the battery isolation protrusion 4235 and the battery clip 4910 collectively form a reversible on/off switch.

The audio output device 4956 of the electronic circuit system 4900 is configured to output audible sound to a user in response to a use of the medical injector 4000. In some embodiments, the audible output device 4956 can be a speaker. In some embodiments, the audible sound can be, for example, associated with a recorded message and/or a recorded speech. In other embodiments, the audible instructions can be an audible beep, a series of tones and/or or the like.

In other embodiments, the medical injector 4000 can have a network interface device (not shown) configured to operatively connect the electronic circuit system 4900 to a remote device (not shown, but which can be similar to the computing device 7801 shown herein) and/or a communications network (not shown, but which can be a short-range network or the network 7805 shown herein). In some embodiments, the electronic circuit system can be configured to establish a short-range radio link with a remote computing device (not shown, e.g., a user's smart phone, a wearable device, or any other computing device that is associated with the user). For example, the electronic circuit system 4900 can be paired to a remote computing device via the Bluetooth® wireless protocol. Similarly stated, the electronic circuit system 4900 can include a processor and/or radio configured to be paired to a remote computing device (not shown) via a wireless protocol that facilitates the transmission of signals within a range of approximately 100 meters or less (i.e., a Class 3 radio) and/or having a frequency within the range of 2400 MHz and 2480 MHz. In this manner, the electronic circuit system 4900 can send information to and/or receive information from the remote device. The remote device can be similar to the device 7801, for example, a remote communications network, a computer, a compliance monitoring device, a cell phone, a personal digital assistant (PDA), a wearable device, a tracking device, or the like. Such an arrangement can be used, for example, to download (from the network) replacement processor-readable code from a central network to the electronic circuit system 4900. In some embodiments, for example, the electronic circuit system 4900 can download (or receive) information associated with a medical injector 4000, such as an expiration date, a recall notice, updated use instructions or the like. Similarly, in some embodiments, the electronic circuit system 4900 can upload (or transmit) compliance information associated with the use of the medical injector 4000 via the network interface device.

The electronic circuit system 4900 (and any of the electronic circuit systems described herein) can include any of the structure and can be configured to perform any of the functions of any of the electronic circuit systems described herein, such as, for example, the electronic circuit system 5900. For example, in some embodiments, the electronic circuit system 4900 can include a Bluetooth® low energy (BLE) processor (not shown), such as DA14581 processor, produced by Dialog Semiconductor. In other embodiments, the electronic circuit system 4900 can include a Bluetooth® low energy (BLE) processor, such any of the processors or chipsets produced by Cambridge Silicon Radio Limited (CSR Ltd), including those in the CSR101x Product family. In yet other embodiments, the electronic circuit system 4900 can include any of the Bluetoothx low energy (BLE) system on chip (SoC) produced by Nordic Semiconductor, including the nRF52840, the nRF52832, the nRF52810 chips. In some embodiments, the electronic circuit system 4900 (and any of the electronic circuit systems described herein) can include a use (or event detection) module, similar to the use module 7982 described herein.

Figure 24:
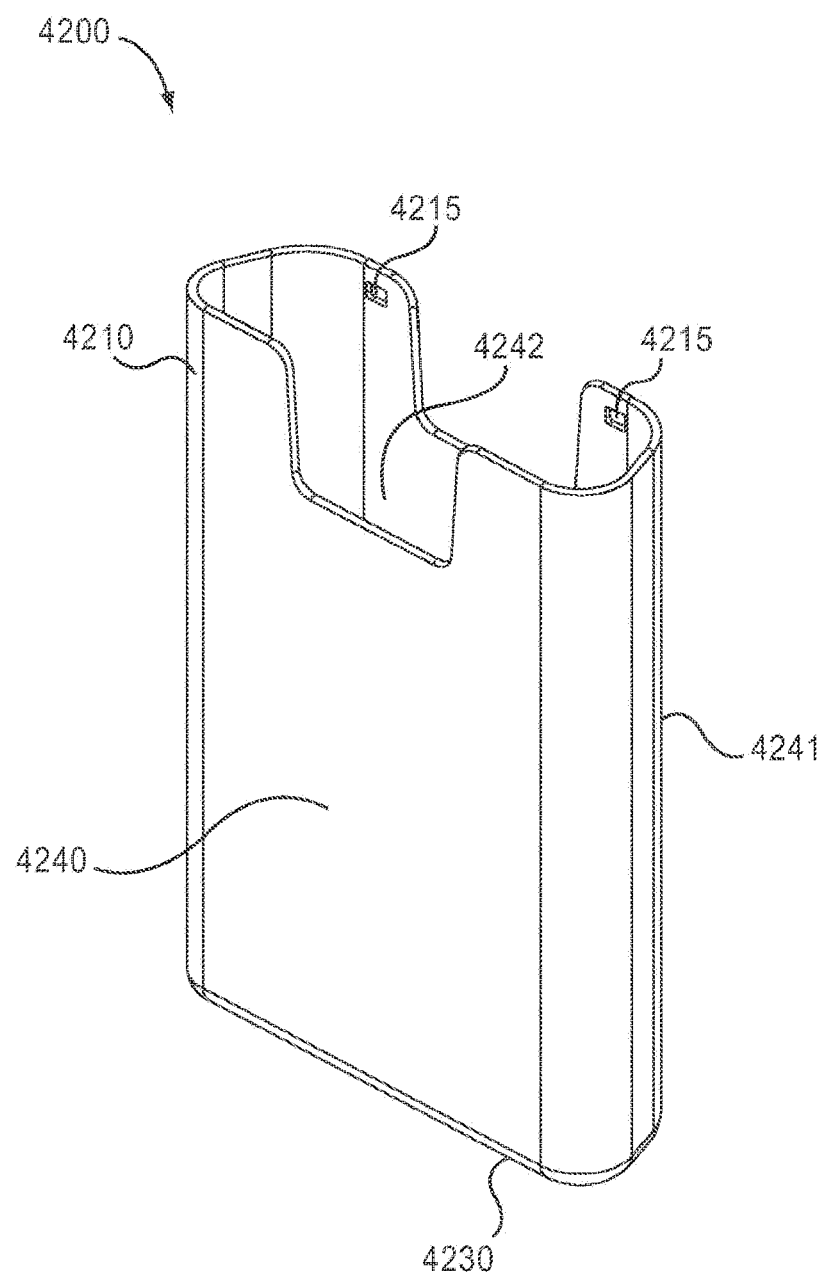
FIGS. 24 and 25 are perspective views of a cover of the medical injector illustrated in FIG. 3.
Figure 25:
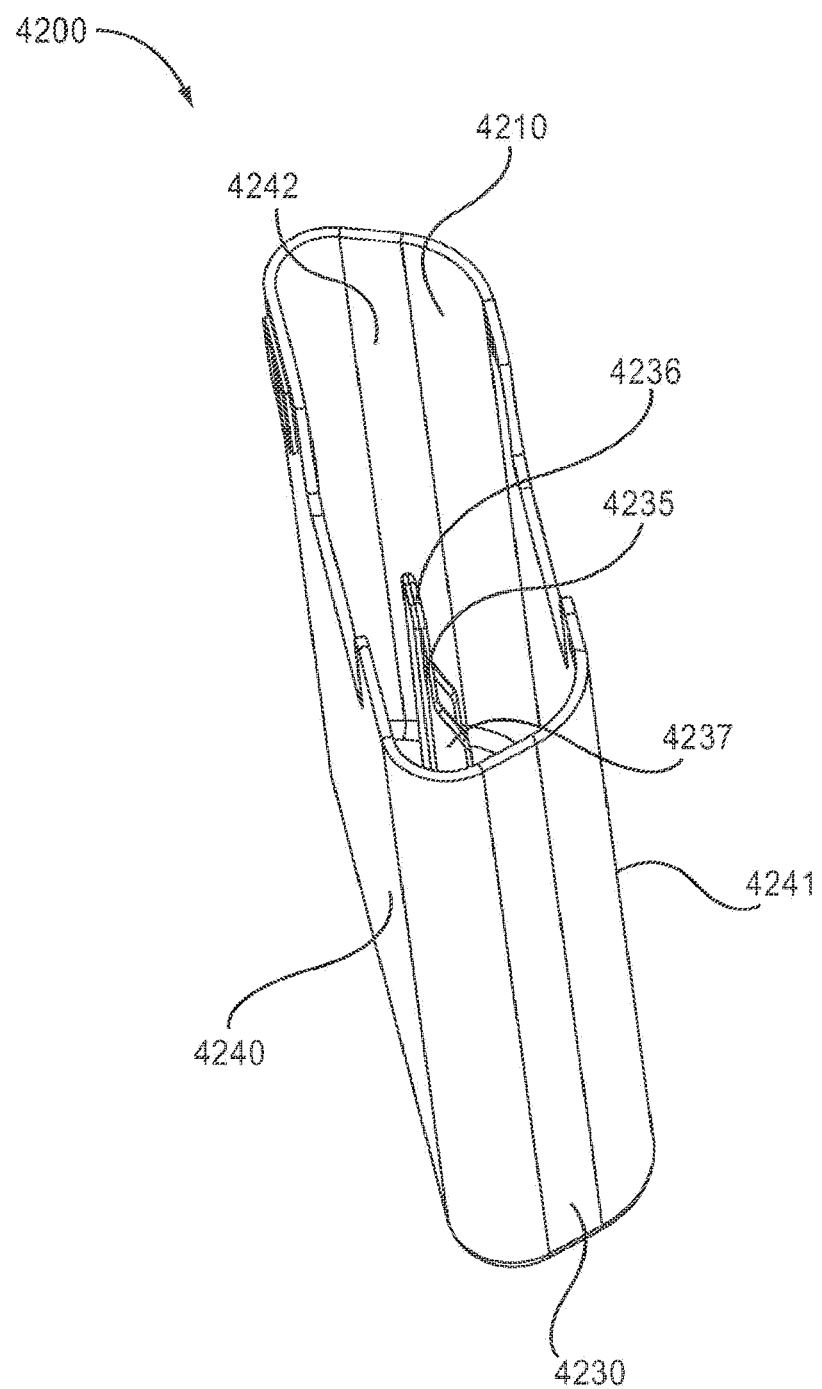
Figure 26:
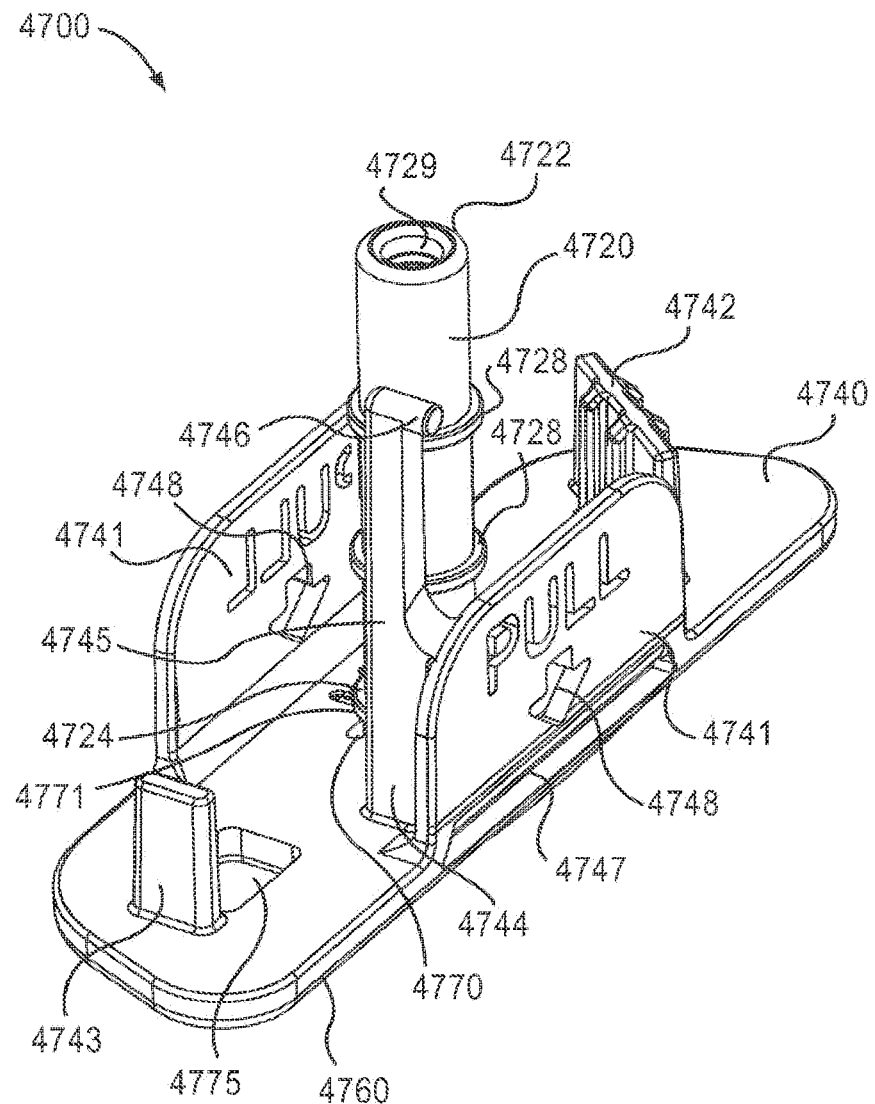
FIGS. 26-28 are a perspective view, a front view, and a bottom view, respectively, of a safety lock of the medical injector illustrated in FIG. 3.

FIGS. 24 and 25 show the cover 4200 of the medical injector 4000. The cover 4200 includes a proximal end portion 4210 and a distal end portion 4230, and defines a cavity 4242. The cavity 4242 of the cover 4200 is configured to receive at least a portion of the housing 4110. The proximal end portion 4210 defines apertures 4215 configured to receive the cover retention protrusions 4142 of the housing 4110 (shown in FIGS. 4 and 6). In this manner, the apertures 4215 and the cover retention protrusions 4142 of the housing 4110 removably retain the cover 4200 about at least a portion of the housing 4110. Said another way, the apertures 4215 and the cover retention protrusions 4142 of the housing 4110 are configured such that the cover 4200 can be removed from a portion of the housing 4110 and then replaced about the portion of the housing 4110.

The distal end portion 4230 of the cover 4200 includes a battery isolation protrusion 4235. The battery isolation protrusion 4235 includes a proximal end portion 4236 and a tapered portion 4237. The proximal end portion 4236 of the battery isolation protrusion 4235 is configured to be removably disposed between the second surface 4966 of the battery assembly 4962 and the contact portion 4918 of the distal end portion 4916 of the battery clip 4910, as described above.

FIGS. 26-29 show the safety lock 4700 of the medical injector 4000. The safety lock 4700 of the medical injector 4000 includes a proximal surface 4740, a distal surface 4760 opposite the proximal surface 4740 and a needle sheath 4720. The safety lock 4700 defines a needle sheath aperture 4770 and a battery isolation protrusion aperture 4775. The battery isolation protrusion aperture 4775 is configured to receive the battery isolation protrusion 4235 of the cover 4200 such that the battery isolation protrusion 4235 can be disposed within the electronic circuit system cavity 4153 or the electronic circuit system 4900, as described above. Similarly stated, the battery isolation protrusion aperture 4775 of the safety lock 4700 is aligned with the battery isolation protrusion aperture 4121 of the housing 4110, such that the battery isolation protrusion 4235 can be disposed within the electronic circuit system cavity 4153 when the cover 4200 is disposed about a portion of the housing 4110.

The proximal surface 4740 of the safety lock 4700 includes a safety lock protrusion 4742, a stopper 4743, an actuator 4744 and two opposing pull tabs 4741. As described above, when the safety lock 4700 is in a first (locked) position, the safety lock protrusion 4742 is configured to be disposed in the opening 4554 defined by the extensions 4552 of the distal end portion 4544 of the release member 4540. Accordingly, the safety lock protrusion 4742 is configured to prevent the extensions 4552 from moving closer to each other, thereby preventing proximal movement of the release member 4540 of the medicament delivery mechanism 4500 and/or delivery of a medicament. The stopper 4743 of the safety lock 4700 is a protrusion extending from the proximal surface 4740 of the safety lock 4700. The stopper 4743 is configured to contact a portion of the housing 4110 to limit the proximal movement of the safety lock 4700 relative to the housing 4110. In other embodiments, the stopper 4743 can be any structure configured to limit the proximal movement of the safety lock 4700.

The actuator 4744 of the safety lock 4700 has an elongated portion 4745 and a protrusion 4746. The elongated portion 4745 extends in a proximal direction from the proximal surface 4740. In this manner, the elongated portion 4745 can extend through a safety lock actuator opening 4356 of the base 4300 (see e.g., FIG. 30) and within the safety lock actuator groove 4123 of the housing 4110 and the safety lock actuator groove 4182 of the electronic circuit system housing 4170. The protrusion 4746 extends in a direction substantially transverse to the elongated portion 4745 and/or substantially parallel to the proximal surface 4740 of the safety lock 4700. As described above, the opening 4928 of the first actuation portion 4926 is configured to receive the protrusion 4746 of the actuator 4744 of the safety lock 4700.

The pull tabs 4741 of the safety lock 4700 include a grip portion 4747 and indicia 4748. The grip portion 4747 of the pull tabs 4741 provides an area for the user to grip and/or remove the safety lock 4700 from the rest of the medicament delivery system 4700. The indicia 4748 provides instruction on how to remove the safety lock 4700. In some embodiments, for example, the indicia 4748 can indicate the direction the user should pull the safety lock 4700 to remove the safety lock 4700.

Figure 28:
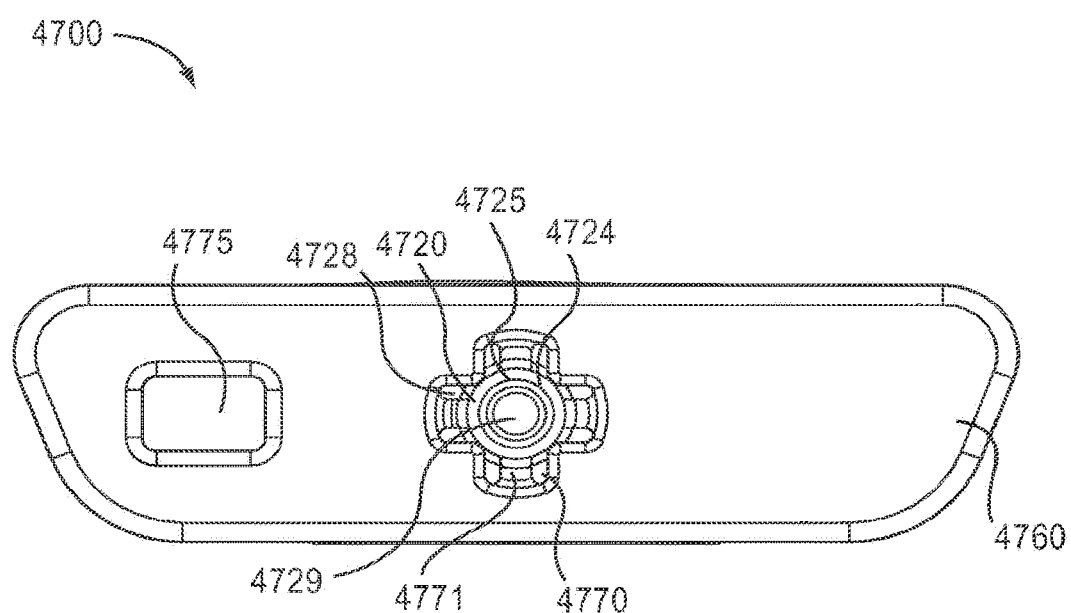
Figure 29:
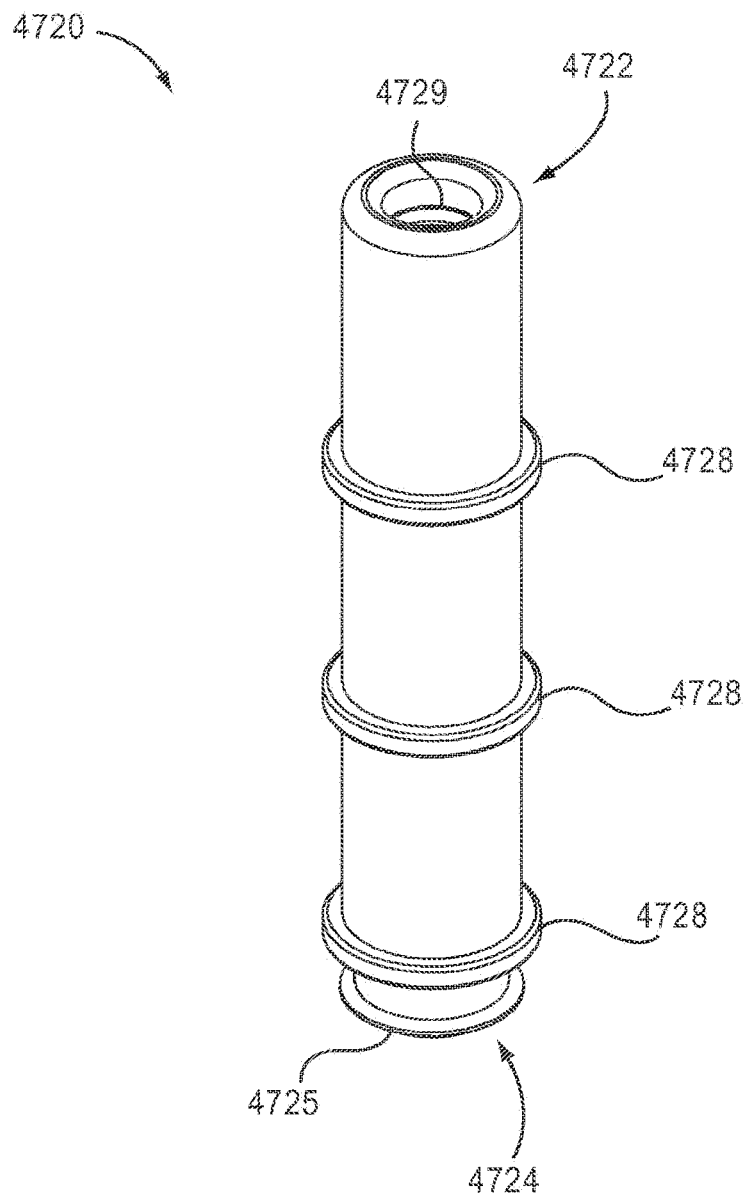
FIG. 29 is a perspective view of a needle sheath of the safety lock of the medical injector illustrated in FIG. 26.

As shown in FIG. 28, the needle sheath 4720 of the safety lock 4700 includes a distal end portion 4724, a proximal end portion 4722 and a plurality of ribs 4728. The needle sheath 4720 can also define a lumen 4729. The lumen 4729 of the safety lock 4700 is configured to receive the needle 4512. In this manner, the needle sheath 4720 can protect the user from the needle 4512 and/or can keep the needle 4512 sterile before the user uses the medical injector 4000. The proximal end portion 4722 of the needle sheath is configured to contact the distal end portion 4522 of the carrier 4520 of the medicament delivery mechanism 4500.

Figure 33:
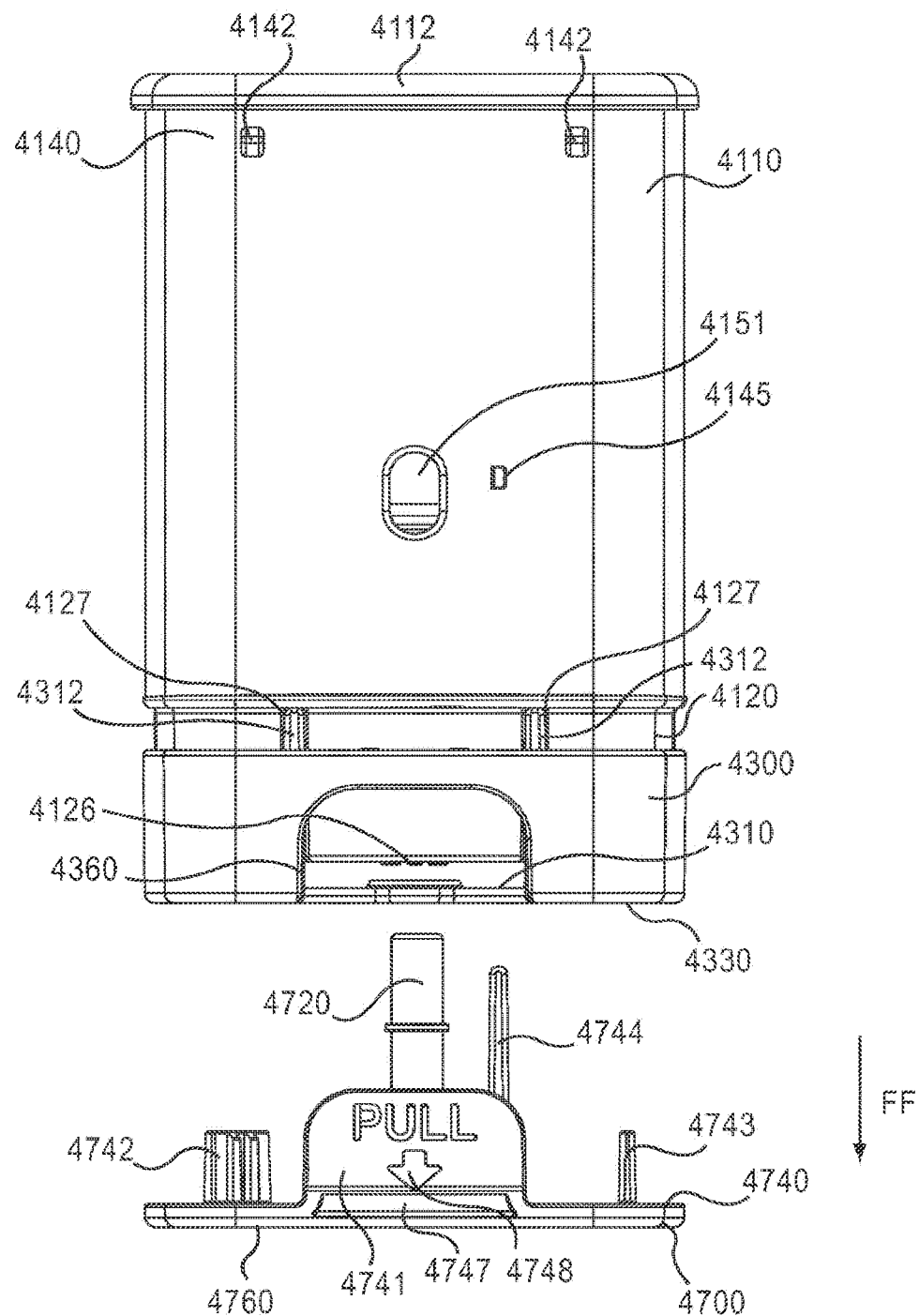
Figure 34:
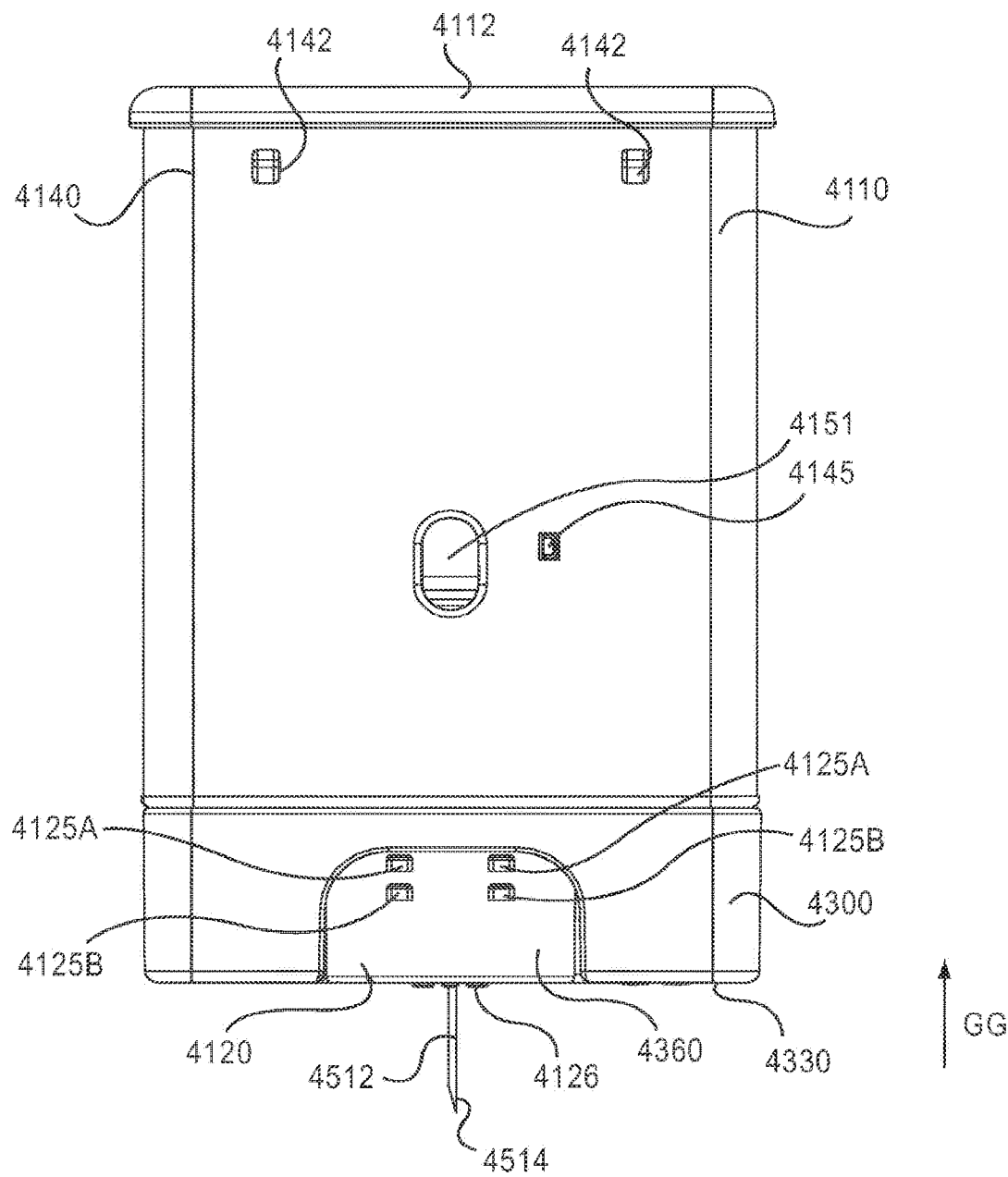

The distal end portion 4724 of the needle sheath 4720 has an angled ridge 4725. The angled ridge 4725 is configured to allow the proximal end portion 4722 of the needle sheath 4720 to irreversibly move through the needle sheath aperture 4770 of the safety lock 4700 in a distal direction. Said another way, the angled ridge 4725 can be configured in such a way as to allow the proximal end portion 4722 of the needle sheath 4720 to move through the needle sheath aperture 4770 in a distal direction, but not in a proximal direction. The needle sheath aperture 4770 has retaining tabs 4771 configured to engage the proximal end of the angled ridge 4725 when the needle sheath 4720 is moved in a proximal direction. In this manner, the retaining tabs 4771 prevent the proximal movement of the needle sheath with respect to the safety lock 4700. Further, the retaining tabs 4771 are configured to engage the proximal end of the angled ridge 4725 when the safety lock 4700 is moved in a distal direction. Said another way, as shown in FIG. 33, the needle sheath 4720 is removed from the needle 4512 when the safety lock 4700 is moved in a distal direction with respect to the housing 4110.

Figure 30:
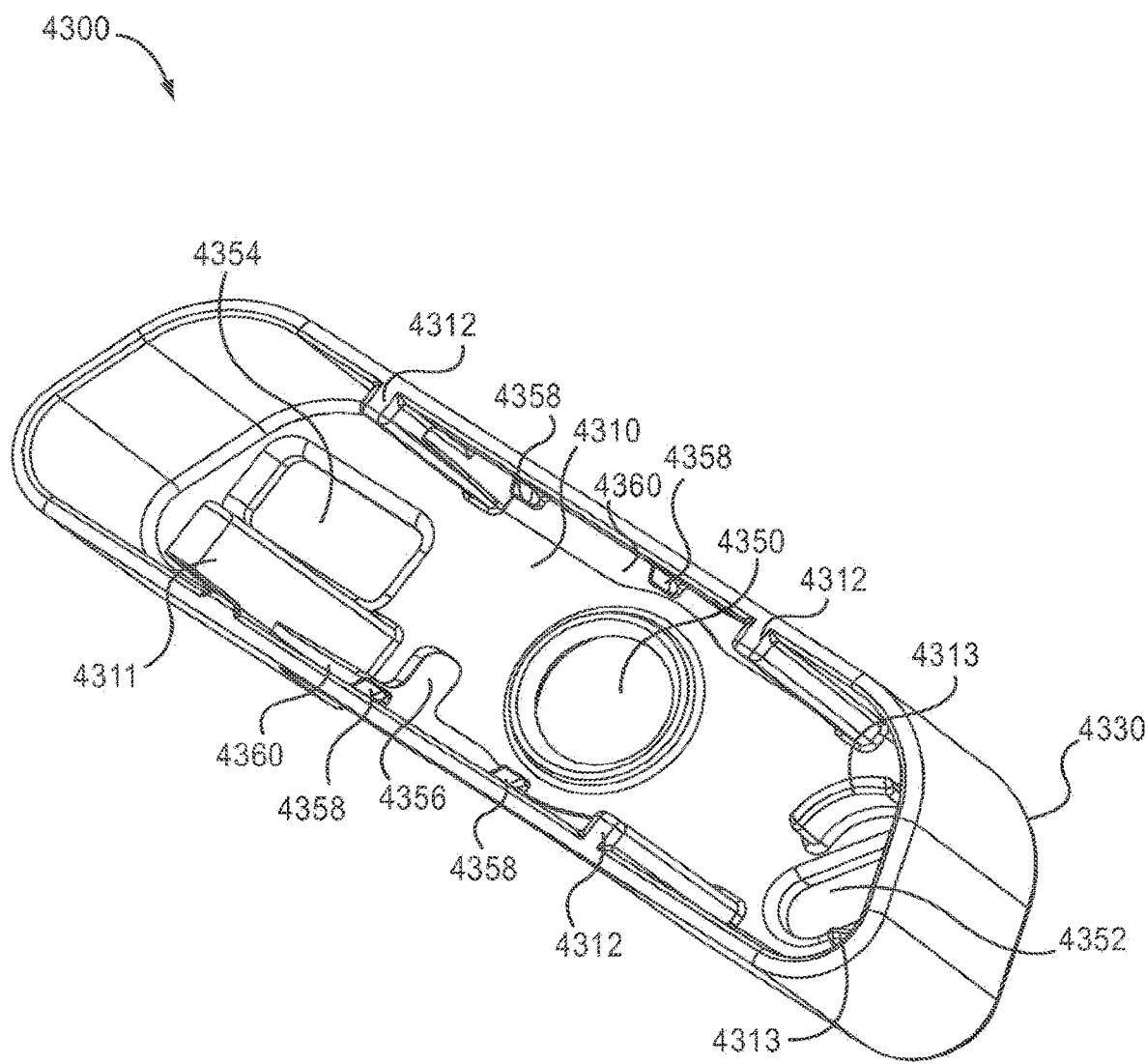
FIGS. 30 and 31 are a perspective view and a front view, respectively, of a base of the medical injector illustrated in FIG. 3.
Figure 31:
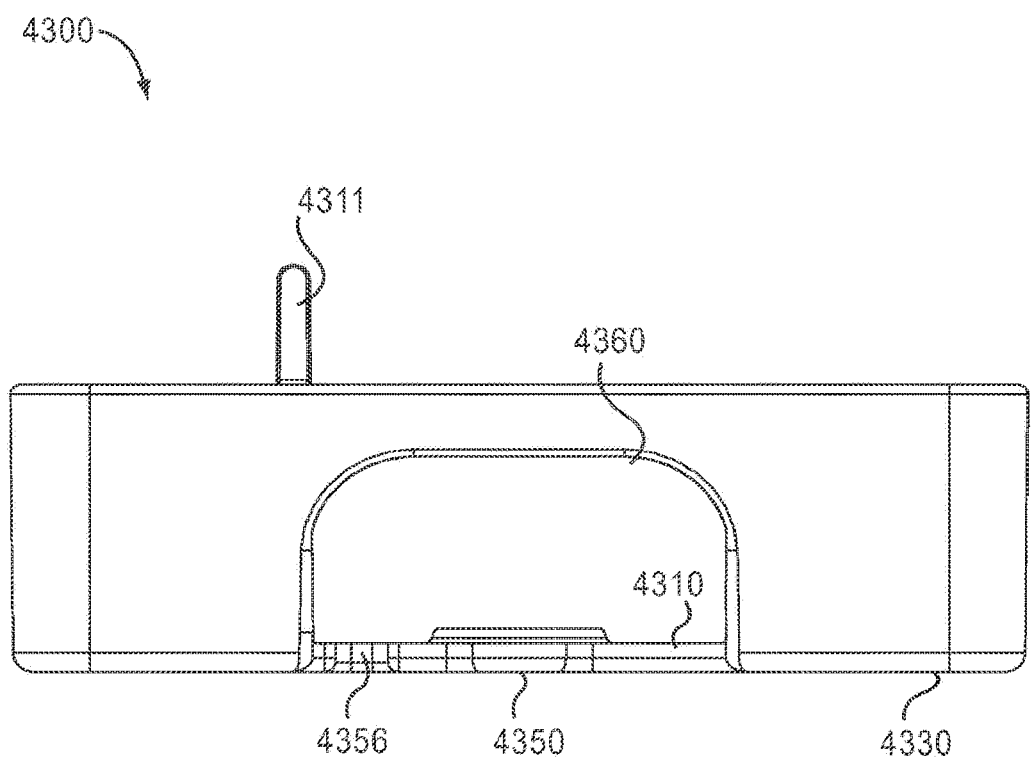

FIGS. 30-31 show the base 4300 of the medical injector 4000. The base 4300 includes a proximal surface 4310, a distal surface 4330 and base connection knobs 4358. The base 4300 defines a needle aperture 4350, a safety lock protrusion aperture 4352, a battery isolation protrusion aperture 4354, a safety lock actuator opening 4356, and pull tab openings 4360. The needle aperture 4350 is configured to receive the needle 4512 when the medical injector 4000 is actuated. The safety lock protrusion aperture 4352 of the base 4300 receives the safety lock protrusion 4742 of the safety lock 4700. The battery isolation protrusion aperture 4354 of the base 4300 receives the battery isolation protrusion 4235 of the cover 4200 and the stopper 4743 of the safety lock 4700. The safety lock actuator opening 4356 receives the safety lock actuator 4744 of the safety lock 4700. The pull tab openings 4360 are configured to receive the pull tabs 4741 of the safety lock 4700.

The proximal surface 4310 of the base 4300 includes an actuator 4311, guide members 4312, and protrusions 4313. The actuator 4311 is an elongate member configured to engage the substrate 4924 of the electronic circuit system 4900. As described above, the opening 4945 of the second actuation portion 4946 is configured to receive the actuator 4311 of the base 4300. The guide members 4312 of the base 4300 are configured to engage and/or slide within the base rail grooves 4127 of the housing 4110, as described above. The protrusions 4313 of the base 4300 are configured to engage the tapered surfaces 4549 of the extensions 4552 of the release member 4540. As described in further detail herein, when the safety lock 4700 is removed and the base 4300 is moved in a proximal direction with respect to the housing 4110, the protrusion 4313 of the base 4300 are configured to move the extensions 4552 of the release member 4540 closer to each other, actuating the medicament delivery mechanism 4500. As described above, the base connection knobs 4358 are configured to engage the base retention recesses 4125A, 4125B in a way that allows proximal movement of the base 4300 but limits distal movement of the base 4300.

Figure 32:
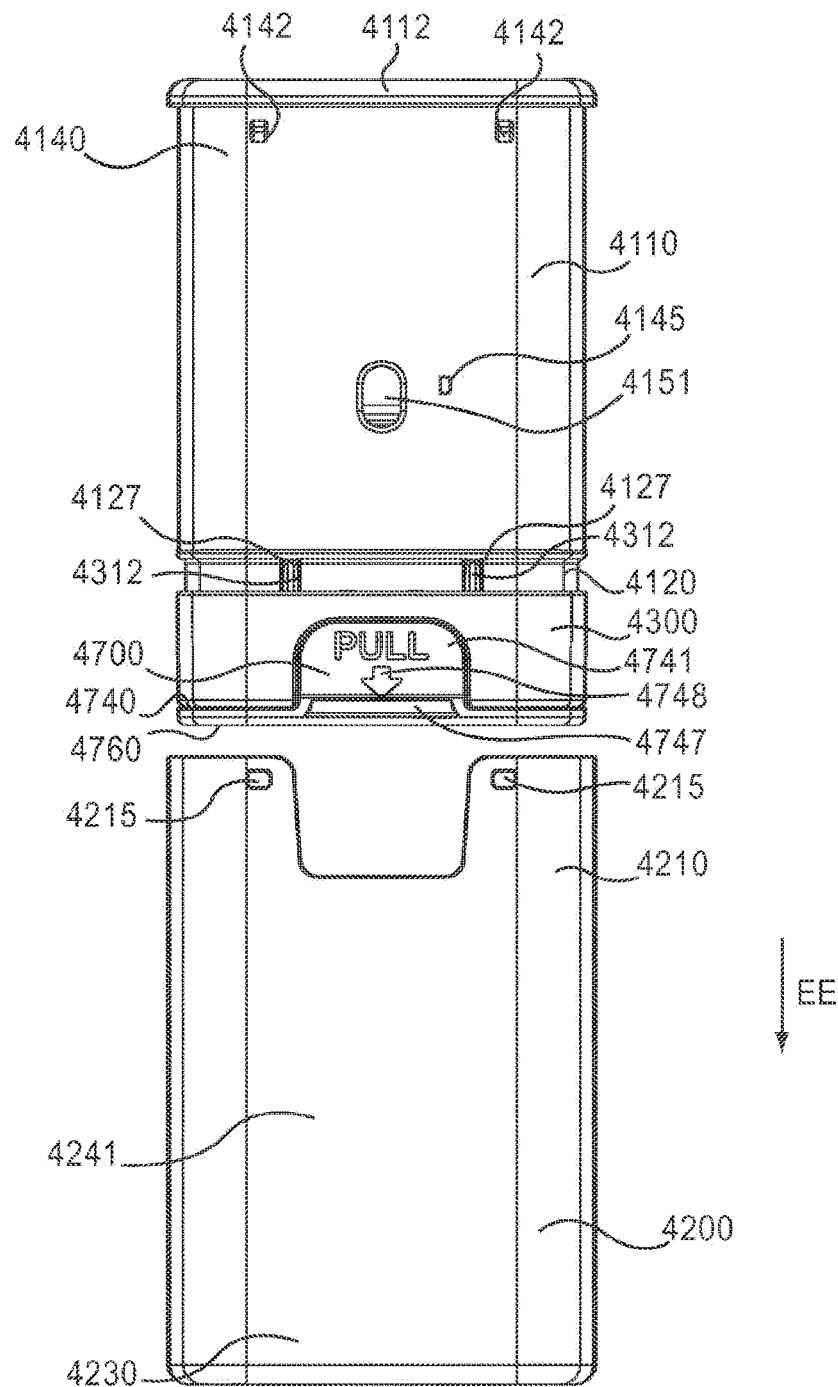
FIGS. 32-34 are a back view of the medical injector illustrated in FIG. 3 in a second configuration, a third configuration, and a fourth configuration, respectively.

As shown in FIG. 32, the medical injector 4000 is first enabled by moving the medicament delivery device from a first configuration to a second configuration by moving the cover 4200 from a first position to a second position. The cover 4200 is moved from the first position to the second position by moving it with respect to the housing 4110 in the direction shown by the arrow EE in FIG. 32. When the cover 4200 is moved with respect to the housing 4110 in the direction EE, the battery isolation protrusion 4235 is removed from the area between the battery clip 4910 and the second surface 4966 of the battery assembly 4962. In this manner, the battery assembly 4962 can be operatively coupled to the electronic circuit system 4900 when the cover 4200 is removed, thereby providing power to the electronic circuit system 4900. In other embodiments, the battery assembly 4962 can be electrically and/or operatively coupled to the electronic circuit system 4900 when the cover 4200 is in its first position. For example, in some embodiments, removal of the cover 4200 actuates a switch to produce an electronic output, similar to that described below with reference to the medical injector 5000.

When power is provided, as described above, the electronic circuit system 4900 can output one or more predetermined electronic outputs. For example, in some embodiments, the electronic circuit system 4900 can output an electronic signal associated with recorded speech to the audible output device 4956. Such an electronic signal can be, for example, associated with a .WAV file that contains a recorded instruction instructing the user in the operation of the medical injector 4000. Such an instruction can state, for example, "remove the safety tab near the base of the auto-injector." The electronic circuit system 4900 can simultaneously output an electronic signal to one and/or both of the LEDs 4958A, 4958B thereby causing one and/or both of the LEDs 4958A, 4958B to flash a particular color. In this manner, the electronic circuit system 4900 can provide both audible and visual instructions to assist the user in the initial operation of the medical injector 4000.

In other embodiments, the electronic circuit system 4900 can output an electronic output associated with a description and/or status of the medical injector 4000 and/or the medicament contained therein. For example, in some embodiments, the electronic circuit system 4900 can output an audible message indicating the type of medicament contained in the medical injector 4000, the expiration date of the medicament, the dosage of the medicament or the like.

In yet other embodiments, the electronic circuit system 4900 can output a wireless electronic output that is received by a computing device (e.g., a user's mobile phone, such as the computing device 7801 described herein). Such wireless outputs can be any wireless outputs of the types shown and described herein.

In yet other embodiments, the removal of the cover 4200 can result in a signal being transmitted to the processor (not shown, but similar to the processor 7980 or the processor 5980 described herein) of the electronic circuit system 4900. Such signals can be received, manipulated and/or used by any of the modules described herein (e.g., an event detection module, a power management module, or the like) to perform any of the methods described herein.

As described above, the medical injector 4000 can be repeatedly moved between the first configuration and the second configuration when the cover 4200 is moved repeatedly between the first position and the second position respectively. Said another way, the cover 4200 can be removed and replaced about the housing 4110 any number of times. When the cover 4200 is moved from the second position to the first position, the battery isolation protrusion 4235 is inserted between the battery clip 4910 and the second surface 4966 of the battery assembly 4962, deactivating the electronic circuit system 4900. When the cover is moved from the first position to the second position a second time, the electronic circuit system 4900 is once again activated. In this manner, the cover 4200 can be removed and the electronic circuit system 4900 can output an electronic output without compromising the sterility of the needle 4512.

In some embodiments, the electronic circuit system 4900 (or any of the electronic circuit system described herein) can include a voltage monitor that monitors the voltage (and/or the capacity) of the battery assembly 4962. In this manner, as the power is depleted, which can occur, for example, due to numerous removals of the cover 4200, the electronic circuit system 4900 can produce an output and/or change its operating configuration. For example, in some embodiments, when the capacity of the battery assembly 4962 drops below a threshold level, the electronic circuit system 4900 can produce an audible warning to the user. In some embodiments, when the capacity of the battery assembly 4962 drops below a threshold level, the electronic circuit system 4900 can produce a wireless output that is received by the user's computing device (not shown, but similar to the computing device 7801), a caregiver's computing device (not shown, but similar to the computing device 7802), or the like. In this manner, a person associated with the user can be apprised of the low power state of the device. In some embodiments, when the capacity of the battery assembly 4962 drops below a threshold level, the electronic circuit system 4900 can change a wireless communication mode to limit or eliminate communications with a computing device (e.g., the device 7801). In this manner, the power can be saved for critical operations, such as providing audible instructions during actual use.

After the cover 4200 is removed from the housing 4110, the medical injector 4000 can be moved from the second configuration to a third configuration by moving the safety lock 4700 from a first position to a second position. The safety lock 4700 is moved from a first position to a second position by moving the safety lock 4700 with respect to the housing 4110 in the direction shown by the arrow FF in FIG. 33. When the safety lock 4700 is moved from the first position to the second position, the safety lock protrusion 4742 is removed from between the extensions 4552 of the release member 4540, thereby enabling the medicament delivery member 4500. Moreover, as shown in FIGS. 21 and 22, when the safety lock 4700 is moved from the housing 4110, the actuator 4744 of the safety lock 4700 moves in the direction CC as shown in FIG. 22, irreversibly moving the first switch 4972 from a first state (e.g., a state of electrical continuity) to a second state (e.g., a state of electrical discontinuity). When the actuator 4744 of the safety lock 4700 moves irreversibly the first switch 4972 of the electronic circuit system 4900 to the second state, the electronic circuit system 4900 can output one or more predetermined electronic outputs. For example, in some embodiments, a processor (not shown) can output an electronic signal associated with recorded speech to the audible output device 4956. Such an electronic signal can be, for example, associated with a recorded message notifying the user of the status of the medical injector 4000. Such a status message can state, for example, "The medical injector is now enabled." The electronic circuit system 4900 can also simultaneously output an electronic signal to one and/or both of the LEDs 4958A, 4958B, thereby causing one and/or both of the LEDs 4958A, 4958B to stop flashing, change color or the like. In some embodiments, the electronic circuit system 4900 can produce a wireless output, of any of the types shown and described herein.

In some embodiments, the first actuation portion 4926 and the actuator 4744 can be configured such that the actuator 4744 must move a predetermined distance before the actuator 4744 engages the boundary 4929 of the opening 4928. For example, in some embodiments, the actuator 4744 must move approximately 0.200 inches before the actuator 4744 engages the boundary 4929 of the opening 4928. In this manner, the safety lock 4700 can be moved slightly without irreversibly moving the first switch 4972 of the electronic circuit system 4900 to the second state. Accordingly, this arrangement will permit the user to inadvertently and/or accidentally move the safety lock 4700 without actuating the electronic circuit system 4900.

In some embodiments, the electronic circuit system 4900 can be configured to output the status message for a predetermined time period, such as, for example, five seconds. After the predetermined time period has elapsed, the electronic circuit system 4900 can output an audible message further instructing the user in the operation of the medical injector 4000. Such an instruction can state, for example, "Place the base of the auto-injector against the patient's thigh. To complete the injection, press the base firmly against the patient's thigh." In some embodiments, the electronic circuit system 4900 can simultaneously output an electronic signal to one and/or both of the LEDs 4958A, 4958B, thereby causing one and/or both of the LEDs 4958A, 4958B to flash a particular color. In this manner, the electronic circuit system 4900 can provide both audible and/or visual instructions to assist the user in the placement and actuation of the medical injector 4000. In some embodiments, the electronic circuit system 4900 can be configured to repeat the instructions after a predetermined time period has elapsed.

As described above, in other embodiments, the medical injector 4000 can have a network interface device or radio (not shown, but similar to that shown for the electronic circuit system 7900) configured to operatively connect the electronic circuit system 4900 to a remote device (not shown, but similar to the device 7801) and/or a communications network (not shown, but similar to the network 7805). In this manner, the electronic circuit system 4900 can send a wireless signal notifying a remote device that the safety lock 4700 of the medical injector 4000 has been removed and that the medical injector 4000 has been armed.

In yet other embodiments, the removal of the safety lock 4700 can result in a signal being transmitted to the processor (not shown, but similar to the processor 7980 or the processor 5980 described herein) of the electronic circuit system 4900. Such signals can be received, manipulated and/or used by any of the modules described herein (e.g., an event detection module, a motion module, or the like) to perform any of the methods described herein.

After the safety lock 4700 is moved from the first position to the second position, the medical injector 4000 can be moved from the third configuration to a fourth configuration by moving the base 4300 from a first position to a second position. The base 4300 is moved from its first position to its second position by placing the medical injector 4000 against the body of the patient and moving the base 4300 with respect to the housing 4110 in the direction shown by the arrow GG in FIG. 34. Moving the base 4300 from the first position to the second position causes the protrusions 4313 on the proximal surface 4310 of the base 4300 to engage the tapered surfaces 4549 of the extensions 4552 of the release member 4540, causing the release member 4540 to actuate the medicament delivery mechanism 4500 and deliver a medicament to a body of a patient.

When the base 4300 is moved from the first position to the second position, the medicament delivery mechanism 4500 is actuated such that the puncturer 4541 of the release member 4540 is brought in contact with and/or punctures the frangible seal 4573 of the gas container 4570. In some embodiments, the movement of the release member 4540 can be caused by a spring (not shown in FIG. 12). After the frangible seal 4573 has been punctured, an actuating portion of a compressed gas can escape from the gas container 4570 and flow via the gas passageway 4144 into the medicament cavity 4157. The gas applies gas pressure to the movable member 4530 causing the movable member 4530 and the carrier 4520 to move in a distal direction within the medicament cavity 4157. When the carrier 4520 moves distally within the medicament cavity 4157, the carrier 4520 and the medicament container 4560 are in a first configuration. Accordingly, as described above, the medicament container 4560 is connected to the carrier 4520 by a "snap fit" connection. In this manner, the medicament container 4560 and the needle 4512 contemporaneously move with movable member 4530 and/or the carrier 4520 in a distal direction. As described above, the proximal end portion 4516 of the needle 4512 is connected to the distal end portion 4522 of the carrier 4520 and is spaced from the seal 4523 of the medicament container 4560 when the carrier 4520 is in its first configuration. Said another way, the medicament container 4560 and the needle 4512 do not define a medicament delivery path when the carrier 4520 is in the first configuration. The movement of the needle 4512 in a distal direction causes the proximal end portion 4516 of the needle 4512 to exit the housing 4110 and enter the body of a patient prior to administering a medicament.

After the carrier 4520 and/or the needle 4512 have moved within the medicament cavity 4157 a predetermined distance, the carrier 4520 and the medicament container 4560 are moved from the first configuration to a second configuration. In the second configuration of the carrier 4520, the medicament container 4560 is released from the "snap-fit" allowing the medicament container 4560 and the movable member 4530 to continue to move in a distal direction relative to the carrier 4520. Said another way, the medicament container 4560 is configured to slidably move within the carrier 4520 when the carrier is moved from the first configuration to the second configuration. As the medicament container 4560 continues to move within the carrier 4520, the proximal end portion 4516 of the needle 4512 contacts and punctures the seal 4523 of the medicament container 4560. This allows the medicament contained in the medicament container 4560 to flow into the lumen (not shown) defined by the needle 4512, thereby defining a medicament delivery path.

As the medicament container 4560 contacts the distal end of the carrier 4520, the medicament container 4560 stops moving within the carrier 4520 while the movable member 4530 continues to move in a distal direction. This causes the piston portion 4534 of the movable member 4530 to sealingly slide and/or move within the medicament container 4560 containing a liquid medicament. As the piston portion 4534 of the movable member 4530 sealingly slides and/or moves within the medicament container 4560, the piston portion 4534 generates a pressure upon the medicament contained within the medicament container 4560, thereby allowing at least a portion of the medicament to flow out of the medicament container 4560 and into the lumen defined by the needle 4512. The medicament is delivered to a body of a user via the medicament delivery path defined by the medicament container 4560 and the needle 4512.

As described above, the actuator 4538 of the base 4300 actuates the electronic circuit 4900 to trigger a predetermined output or sequence of outputs when the base 4520 is moved from its first position to its second position (see, e.g., FIGS. 19-23). When the actuator 4538 is moved in a proximal direction relative to the opening 4945, as shown by the arrow DD in FIG. 23, the electronic circuit system 4900 is actuated to output one or more predetermined electronic outputs. For example, in some embodiments, the electronic circuit system 4900 can output an electronic signal associated with recorded speech to the audible output device 4956. Such an electronic signal can be, for example, associated with an audible countdown timer, instructing the user on the duration of the injection procedure. Said another way, if it takes, for example, ten seconds to complete an injection, an audible countdown timer can count from ten to zero ensuring that the user maintains the medical injector 4000 in place for the full ten seconds. In other embodiments, the electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor." The electronic circuit system 4900 can also simultaneously output an electronic signal to one and/or both LEDs 4958A, 4958B, thereby causing one and/or both LEDs 4958A, 4958B to stop flashing, change color or the like, to provide a visual indication that the injection is complete. In other embodiments, the electronic circuit system 4900 can send a wireless signal notifying a remote device that the injection is complete. In this manner, a patient's compliance can be monitored.

In some embodiments, the second actuation portion 4946 and the actuator 4538 can be configured such that the base 4500 and/or the actuator 4538 must move a predetermined distance before the actuator 4538 engages the boundary 4949 of the opening 4945. For example, in some embodiments, the actuator 4538 must move approximately 0.200 inches before the actuator 4538 engages the boundary 4949 of the opening 4945. In this manner, the base 4700 can be moved slightly without irreversibly moving the second switch 4973 of the electronic circuit system 4900 to the second state. Accordingly, this arrangement will permit the user to inadvertently and/or accidentally move the base 4500 without actuating the electronic circuit system 4900.

As described above, in other embodiments, the medical injector 4000 can have a network interface device or radio (not shown, but similar to that shown for the electronic circuit system 7900) configured to operatively connect the electronic circuit system 4900 to a remote device (not shown, but similar to the device 7801) and/or a communications network (not shown, but similar to the network 7805). In this manner, the electronic circuit system 4900 can send a wireless signal notifying a remote device that the base 4300 of the medical injector 4000 has been moved and that the medical injector 4000 has been actuated. In some embodiments, the electronic circuit system 4900 can include a sensor (e.g., of the types described with reference to the sensor 7970) that produces provides "event detection" capability for the medical injector 4000. For example, in some embodiments, the electronic circuit system 4900 can include an accelerometer that detects a characteristic movement or vibration signature of the medical injector 4000 when the device is actuated.

Although the electronic circuit system 4900 is shown and described as being configured to receive the battery isolation protrusion 4235 of the cover 4200 to electrically isolate the battery assembly 4956, in other embodiments, a power source can remain coupled to other portions of an electronic circuit system (such as a processor) when device is in a "storage state." Specifically, in some embodiments, a medicament delivery device (or drug product) can include an electronic circuit system that remains powered even when within a sleeve or cover (such as the cover 4200). In this manner, certain portions of the electronic circuit system can continue to function to facilitate the methods associated with the alerts, the connected health delivery systems (e.g., the systems 5800, 6800), or the like. Such functions can include, for example, continued operation of an internal processor clock, continued operation of wireless communication functions (e.g., to be paired with, communicate with, or search for a remote computing device, such as the user's mobile phone).

Although the electronic circuit system 4900 is shown and described as including single-use or "tear through" switches 4972, 4973 that provide feedback to the electronic circuit system 4900 (and processor) regarding the status of the device 4000, in other embodiments, any suitable switches can be included in any of the electronic circuit system 4900 (or any other electronic circuit systems) described herein. For example, in some embodiments, an electronic circuit system can include re-usable toggle switches, optical switches, or the like.

For example, FIGS. 35-41 show a medicament delivery device (also referred to as a medical injector an auto-injector) 5000 having an electronic circuit system 5900 that has wireless connectivity. The medicament delivery device 5000 can be included in any of the connected health medicament delivery systems shown and described herein, such as the connected health medicament delivery systems 5800, 6800, and 7800 described herein. The medicament delivery device 5000 can include any of the features of any of the devices shown and described herein, including the features shown and described above with reference to the device 4000. For example, the medicament delivery device 5000 can include a gas container, similar to the gas container 4570 shown and described above, that produces a force to deliver a medicament (e.g., by first inserting a needle, and then delivering the medicament therethrough). As another example, the medicament delivery device 5000 can include a carrier, similar to the carrier 4520, that holds and/or moves a medicament container during use.

Figure 35:
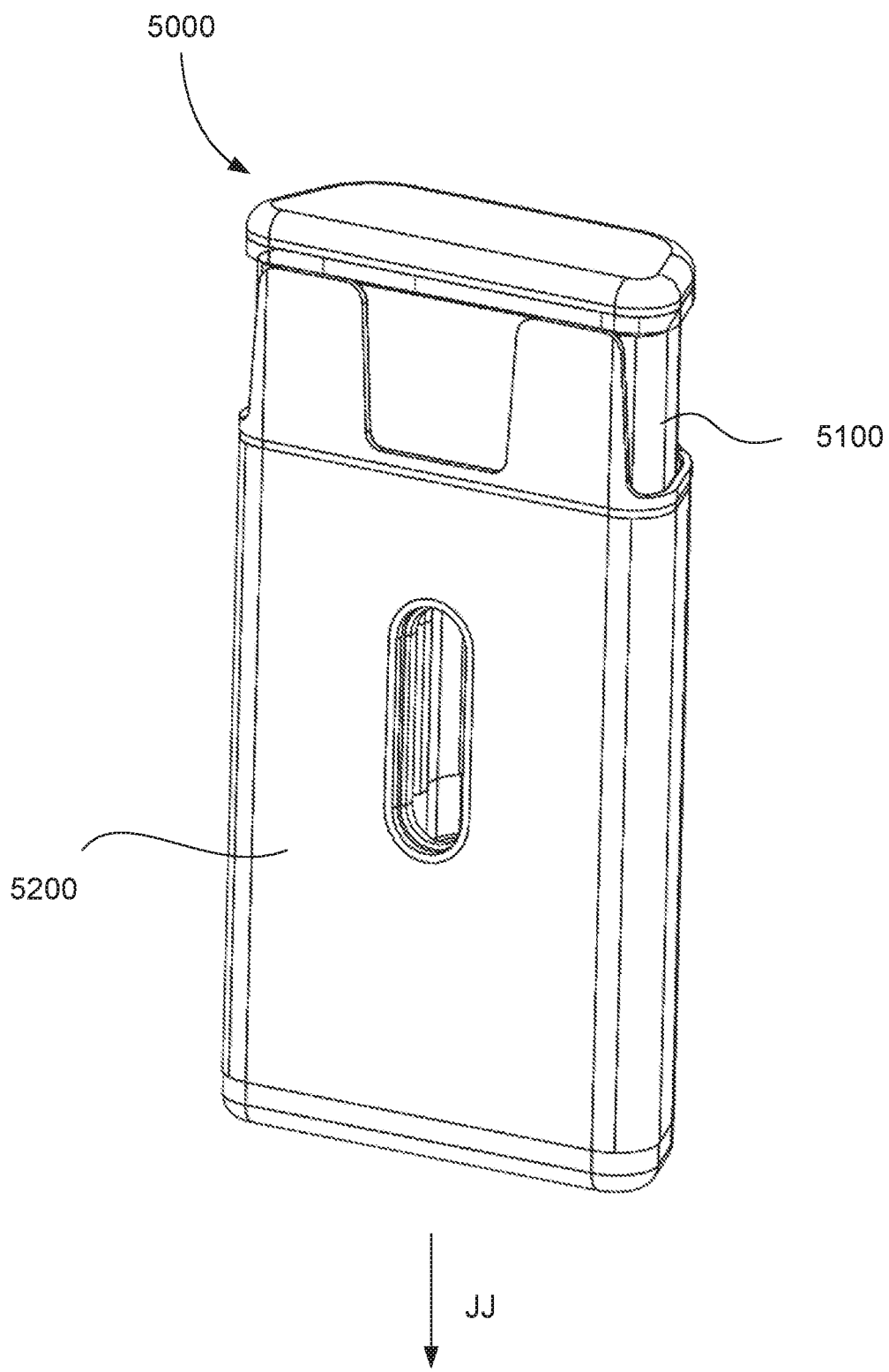
FIGS. 35 and 36 are perspective views of a medical injector according to an embodiment.

As shown in FIG. 35, the medicament delivery device 5000 includes, among other components, a housing 5100, a cover 5200, a base 5300 (or actuator), a safety lock 5700, and an electronic circuit system 5900. The housing 5100 contains the components of the medicament delivery device 5000, and can be similar in structure and function to the housing 4110 described above. Similar to the cover 4200 described above, the cover 5200 can be removably coupled to and disposed about at least a portion of the housing 5100. In contrast to the cover 4200, however, the cover 5200 defines a status aperture (or window) that aligns with the status aperture of the housing 5100 when the cover 5200 is in place about the housing 5100. In some embodiments, the cover 5200 can define one or more apertures or can include one or more protrusions that matingly engage corresponding portions of the housing 5100 to removably retain the cover 5200 about at least a portion of the housing 5100. In this manner, the cover 5200 is configured to be repeatedly removed from and replaced about a portion of the housing 5100, but in a manner that requires a minimum threshold force to remove the cover 5200 such that the cover cannot easily "fall from" or be inadvertently removed from about the housing 5100. In some embodiments, the distal end portion of the cover 5200 includes a switch protrusion configured to engage and/or actuate the switch 5974 to actuate the electronic circuit system 5900 when the cover 5200 is removed from about the housing 5100.

The medicament delivery device 5000 can be similar to the medicament delivery devices shown and described in International Patent Publication No. WO2017/004345, entitled "Auto-Injectors for Administration of a Medicament within a Prefilled Syringe," which is incorporated herein by reference in its entirety. For example, the medicament delivery device 5000 can include one or more prefilled syringes containing any amount and type of medicament described herein. Further, the medicament delivery device 5000 can include a gas container and an expandable assembly that releases gas pressure, as shown and described in WO2017/004345.

The electronic circuit system 5900 can include any suitable components to perform any of the functions described herein, including functions associated with the electronic circuit system 4900 described herein. Specifically, the electronic circuit system 5900 of the medical injector 5000 includes an electronic circuit system housing 5170, a printed circuit board 5922, a battery assembly 5960, an audio output device 5956, two light emitting diodes (LEDs) 5958, a series of sensors and switches, and a processor that includes wireless communication functionality. The electronic circuit system 5900 is configured to fit within an electronic circuit system cavity of the housing 5100. Accordingly, the electronic circuit system 5900 is physically and/or fluidically isolated from the medicament cavity or any medicament delivery path of the device 5000. As described herein, the electronic circuit system 5900 is configured to output one or more electronic outputs, including wireless signals, associated with the use of the medical injector 5000. The electronic circuit system 5900 can therefore communicate with (either directly or indirectly via a network) other devices within any of the connected health medicament delivery systems shown and described herein, such as the connected health medicament delivery systems 5800, 6800, and 7800 described herein.

The electronic circuit system housing 5170 includes connection protrusions, ribs, and tabs (defining connection apertures) that are configured to be disposed within or otherwise matingly engage the connection portions of the housing 5100. In this manner, the electronic circuit system 5900 can be coupled to the housing 5110 within an electronic circuit system cavity. In other embodiments, the electronic circuit system 5900 can be coupled to the housing 5100 by other suitable means such as an adhesive, a clip and/or the like. Although shown as being coupled to the housing 5100, in other embodiments, an electronic circuit system can be coupled to the cover 5200, and can thus be removably coupled to the housing 5100 and/or the medicament delivery device 5000.

The printed circuit board 5922 of the electronic circuit system 5900 is coupled to the electronic circuit system housing 5170 and includes the necessary structure (e.g., substrates, vias, connectors, etc.) to interconnect the components of the electronic circuit system 5900. For example, the circuit board 5922 includes a first connector/adapter 5923 that, along with the battery wires 5924, electrically couples the battery assembly 5960 to the printed circuit board 5922 and the processor (and the remainder of the electronic circuit system 5900) to power the system. The circuit board also includes a second connector/adapter 5925 that, along with the speaker wires 5926, electrically couples the speaker 5956 to printed circuit board 5922. The use of mating connectors can provide assembly benefits. The printed circuit board 5922 is populated with the components described herein, such as resistors, capacitors, inductors, switches, microcontrollers, and/or microprocessors. The printed circuit board 5922 (and the components thereon) can be similar to those shown and described in U.S. Pat. No. 10,332,623, entitled "Medicament Delivery Devices with Wireless Connectivity and Event Detection," filed Jan. 16, 2018, which is incorporated herein by reference in its entirety.

The electronic circuit system 5900 includes a Bluetoothx low energy (BLE) processor (not shown) that can be similar to the processor 5980 shown and described in U.S. Pat. No. 10,332,623, entitled "Medicament Delivery Devices with Wireless Connectivity and Event Detection," filed Jan. 16, 2018, which is incorporated herein by reference in its entirety. The processor, and any of the processors described herein, can be any suitable processor for performing the methods described herein. In some embodiments, processor can be configured to run and/or execute application modules, processes and/or functions associated with such a medicament delivery system 5800. For example, the processor can be configured to run and/or execute any or all of the computer-implemented modules described herein. Such modules include, for example, the communication module 1981, described above, a power management module (e.g., the power management module 7987), a use (or event detection) module (e.g., the event detection module 7982), an expiration/reordering module (e.g., the notification module 7988, a motion module, (e.g., the motion module 7983), a predictive module (e.g., the predictive module 7986), and/or the leash module (e.g., the leash module 1983), and perform the methods associated therewith.

The processor can be configured to retrieve data from and/or write data to memory (not shown). The memory can be similar to the memory 7999 described herein or the memory 5989 shown and described in U.S. Pat. No. 10,332,623, entitled "Medicament Delivery Devices with Wireless Connectivity and Event Detection," filed Jan. 16, 2018, which is incorporated herein by reference in its entirety. As described herein, in some embodiments, the processor 5980 can cooperatively function with a radio and/or execute instructions from code to provide signals to communicatively couple the electronic circuit system 5900 to the computing device 5801 (e.g., via wireless communication) and/or any other computing entity via a network (similar to the network 7805 shown herein). In some embodiments, the processor can cooperatively function with an audio driver to produce signals that are converted by the audible output device 5656 into instructions. In some embodiments, the processor in the electronic circuit system 5900 is a Bluetooth® low energy (BLE) processor, such as The Texas Instruments® CC2540 series of processors, the Broadcom® BCM43341 processor, and/or any other processor suitable or configured specifically to execute the Bluetooth® v4.0 low energy stack. In other embodiments, the processor is a Bluetooth® low energy (BLE) processor, such as DA14581 processor, produced by Dialog Semiconductor. In yet other embodiments, the electronic circuit system 5900 can include a Bluetooth® low energy (BLE) processor, such any of the processors or chipsets produced by Cambridge Silicon Radio Limited (CSR Ltd), including those in the CSR101x Product family. In yet other embodiments, the processor can include any of the Bluetooth® low energy (BLE) system on chip (SoC) produced by Nordic Semiconductor, including the nRF52840, the nRF52832, the nRF52810 chips.

The electronic circuit system includes a radio and/or a network interface device (not shown) configured to operatively connect the electronic circuit system 5900 to a remote device (not shown, but which can be similar to the computing device 7801 or the remote device 5801 shown herein) and/or a communications network (not shown, but which can be a short-range network or the network 7805 shown herein). In some embodiments, the electronic circuit system 5900 can be configured to establish a short-range radio link with a remote computing device (e.g., a user's smart phone, a user's fitness tracking device, or any other remote device, such as the device 5801 or the device 7801 shown herein). For example, the electronic circuit system 5900 can be paired to a remote computing device via the Bluetooth® wireless protocol. Similarly stated, the electronic circuit system 5900 can include a processor and/or radio configured to be paired to a remote computing device (not shown) via a wireless protocol that facilitates the transmission of signals within a range of approximately 100 meters or less (i.e., a Class 3 radio) and/or having a frequency within the range of 2400 MHz and 2480 MHz. In this manner, the electronic circuit system 5900 can send information to and/or receive information from the remote device. The remote device can be similar to the device 7801, for example, a remote communications network, a computer, a compliance monitoring device, a cell phone, a personal digital assistant (PDA) or the like. Such an arrangement can be used, for example, to download replacement processor-readable code from a central network to the electronic circuit system 5900. In some embodiments, for example, the electronic circuit system 5900 can download information associated with a medical injector 5000, such as an expiration date, a recall notice, updated use instructions, or the like. Similarly, in some embodiments, the electronic circuit system 5900 can upload compliance information associated with the use of the medical injector 5000 via the network interface device.

Figure 41:
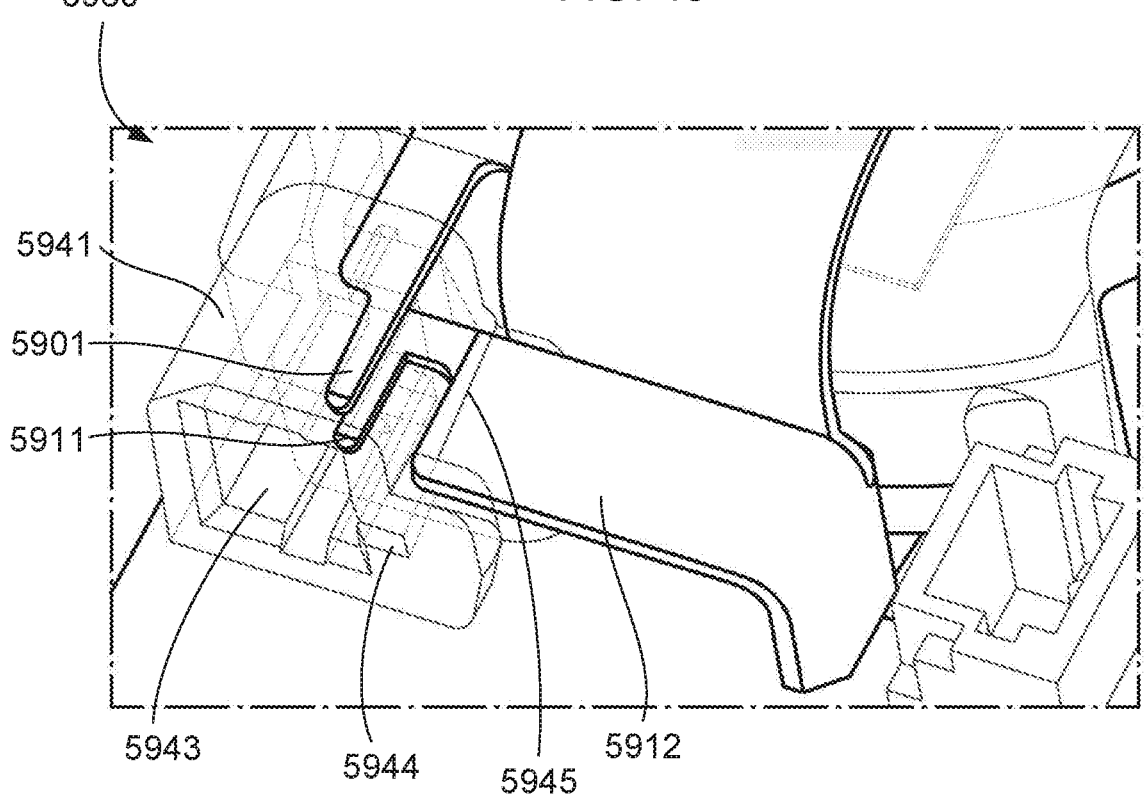
FIG. 41 is an enlarged view of a portion of the electronic circuit system shown in FIGS. 37 and 38.

The battery assembly 5960 of the electronic circuit system 5900 includes a housing 5940, a first battery 5961, and a second battery 5965. The battery assembly 5960 also includes a first clip 5910 and a second clip 5905 that are collectively configured to maintain the battery assembly in connection with (and electrically coupled to) the printed circuit board 5922 and the remainder of the electronic circuit system 5900. The housing 5940 contains the first battery 5961 and the second battery 5965 and securely couples the batteries to the electronics housing 5170 and/or the printed circuit board 5922. The housing 5940 includes one or more mounting protrusions 5942 (or surfaces) and a connector 5941. The mounting protrusions 5942 or surfaces facilitate mounting the housing 5940 to the electronics housing 5170 and/or the printed circuit board 5922. As shown in FIG. 41, the connector 5941 defines an internal volume 5943, a keyway 5944, and a terminal slot 5945. The keyway 5944 matingly receives a portion of a connector 5927 at the end of the battery wires 5924. In some embodiments, the connector 5927 can be locked within the keyway 5944 and/or the internal volume 5943, for example, to prevent the battery wires 5924 from inadvertently disconnecting from the connector 5941.

The volume 5943 is a space within which the first terminal 5911 of the first clip 5910 (i.e., the positive terminal) and the second terminal 5901 of the second clip 5905 (i.e., the negative terminal) are contained. Specifically, a portion of the first clip 5910 is disposed through the terminal slot 5945 so that the first terminal 5911 can extend into the volume 5943. The first terminal 5911 and the second terminal 5901 are within the connector 5941 in a manner that allows some movement of the terminals. Specifically, in some embodiments, the first terminal 5911 is not overmolded or otherwise maintained at a fixed position within the volume 5943, but rather and float. For example, the first terminal 5911 can flex slightly via the cantilevered portion 5912 to move within the connector volume 5943. This arrangement allows for ease of manufacturing and a reliable connection that accommodates part-to-part variability. For example, in some embodiments, this arrangement can result in the first terminal 5911 and/or the second terminal 5901 to be self-aligning with the mating connector 5927. In some embodiments, the second terminal 5901 is also not overmolded or otherwise maintained at a fixed position within the volume 5943. In other embodiments, however, the second terminal 5901 is maintained at a fixed position within the volume 5943 (e.g., by overmolding, potting, or the like). The terminal slot 5945 can be any size and/or shape to accommodate the first terminal 5911. In some embodiments, however, the connector 5941 need not define a terminal slot 5945 and the first terminal 5911 can be disposed within the connector volume 5943 by any other suitable pathway.

Figure 39:
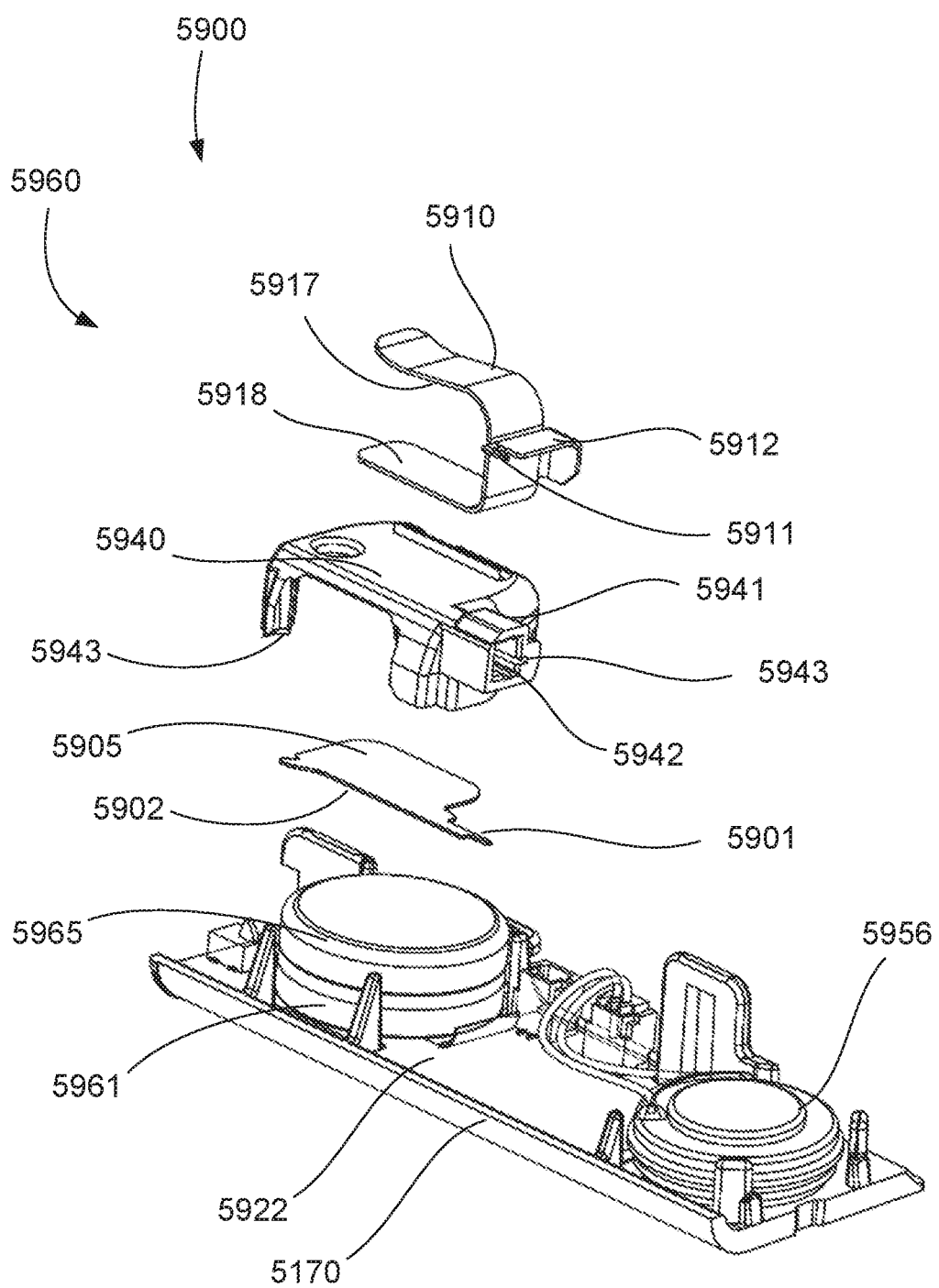
FIGS. 39 and 40 are exploded views of the electronic circuit system shown in FIGS. 37 and 38.
Figure 40:
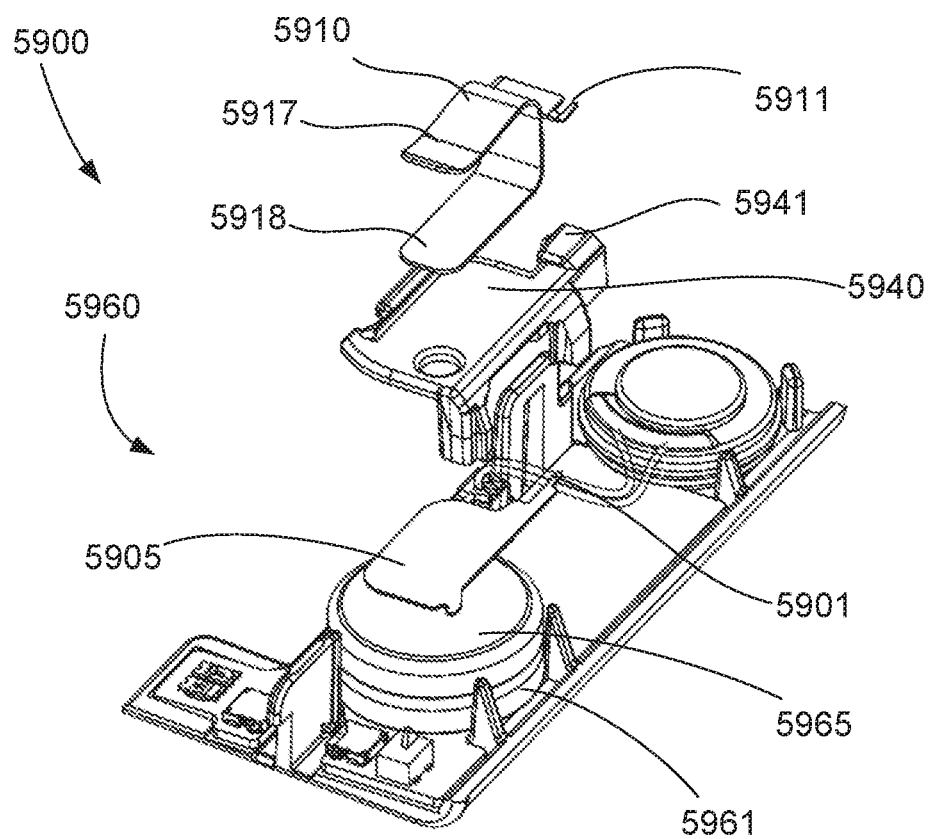

As shown in FIGS. 39 and 40, the first clip 5910 wraps about a portion of the battery housing 5940, and includes a first contact portion 5917 and a second contact portion 5918. The first contact portion 5917 engages the outer portion (also referred to as an outer surface or a top surface) of the battery housing 5940. The second contact portion 5918 is maintained in contact with a bottom surface (i.e., the positive terminal) of the first battery 5961. The first clip 5910 can be constructed in a manner to produce an interference or "resilient" fit about the battery housing 5940. Specifically, the first clip 5910 is "u-shaped" with the first contact portion 5917 opposing the second contact portion 5918. Prior to installation about the battery housing 5940, the first clip 5910 is configured such that the distance between the first contact portion 5917 and the second contact portion 5918 is less than the distance between the outer portion of the battery housing 5940 and the bottom surface of the first battery 5961. In this manner, when the first clip 5910 is assembled about the battery housing 5940 and the batteries, the first clip 5910 is deformed to produce an interference fit to securely couple the first clip 5910 in place. This arrangement also securely retains the batteries within the battery housing 5940. Thus, the battery assembly 5960 can be assembled prior to being coupled to the to the electronics housing 5170 and/or the printed circuit board 5922. The battery housing 5940 is constructed from an electrically isolated material, which prevents the first contact portion 5917 of the first clip from being electrically coupled to the top surface (i.e., the negative terminal) of the second battery 5965, thereby preventing a short-circuit connection. The first clip 5910 includes a cantilevered portion 5912, the end portion of which includes a first terminal 5911. As shown in FIG. 41, the cantilevered portion 5912 extends through the terminal slot 5945. As described herein, the first terminal 5911 is electrically coupled to the first connector 5923 of the printed circuit board via the battery wires 5924 and the connector 5927.

The second clip 5905 is within the battery housing 5940 and includes a contact portion 5902 that is maintained in contact with a top surface (i.e., the negative terminal) of the second battery 5965. The second clip 5905 includes a second terminal 5901 that is also electrically coupled to the first connector 5923 of the printed circuit board via the battery wires 5924 and the connector 5927.

Figure 38:
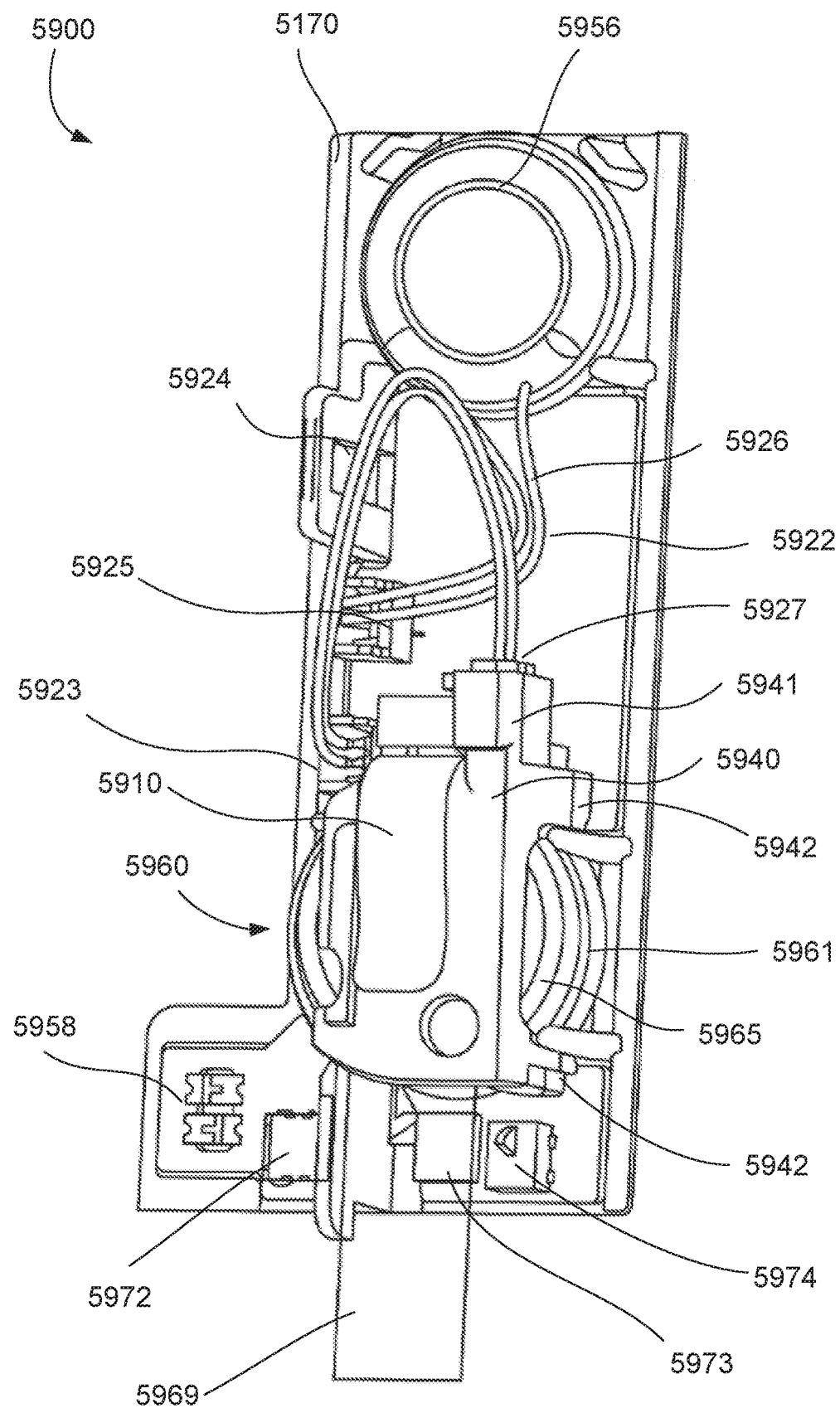

Although the first battery 5961 and the second battery 5965 are maintained in connection with the printed circuit board 5922 when the device 5000 is in use (to allow for operation of the wireless communications features), before being placed in use, a battery isolation tab 5969 is placed between the second battery 5965 and the second clip 5905 (see FIG. 38). The battery isolation tab 5969 electrically isolates the batteries from the remainder of the electronic circuit system 5900 to prevent current draw, thereby extending the life of the electronic circuit system 5900. This arrangement allows the electronic circuit system 5900 to be manufactured and stored for periods of time before beginning the current draw.

The battery assembly 5960 can include any suitable number and type of batteries. The batteries can be, for example CR1632 batteries. Although the battery assembly 5960 is shown as including two batteries, in some embodiments, the battery assembly 5960 can include a single battery. In other embodiments, the battery assembly 5960 can include three, four, or more batteries.

The electronic circuit system 5900 includes a series of sensors that provide feedback to (and/or produce a signal received by) the processor 5980, thus allowing the processor to produce electronic outputs based on the state of the medicament delivery device 5000. In particular, the electronic circuit system 5900 includes a first (or safety) switch 5972, a second (or actuation) switch 5973, and a third (or cover) switch 5974. In addition to the switches, the electronic circuit system 5900 also includes an accelerometer (not shown, but which can be similar to the accelerometer 5971 described in U.S. Pat. No. 10,332,623, entitled "Medicament Delivery Devices with Wireless Connectivity and Event Detection," filed Jan. 16, 2018, which is incorporated herein by reference in its entirety). The accelerometer can be any suitable accelerometer, and can provide input to the processor 5980 regarding the movement and/or vibration of the medicament delivery device 5000. Based on the movement/vibration input the processor 5980 can execute any of the modules and/or execute any of the methods described herein, such as for example, the "carry day" methods described herein. In this manner, the electronic circuit system 5900 can produce a signal (audible, wireless, visual, or the like) that confirms the movement or carrying of the device 5000.

As described above, in contrast to the electronic circuit system 4900, the electronic circuit system 5900 is not isolated from the battery assembly 5960 when the cover 5200 is disposed about the housing 5100. Rather, power is continuously supplied to the processor 5980. When the cover 5200 is removed, a switch protrusion actuates the cover switch 5974 to actuate the electronic circuit system 5900. Upon actuation of the cover switch 5974, the processor and/or any of the modules described herein can produce any of the electronic outputs described herein (e.g., audible, visual, wireless, or the like), can change the communication mode of the radio, and/or otherwise interact with a connected health medicament delivery system (e.g., the system 5800 or any of the other connected health system described herein). For example, in some embodiments, upon removal of the cover 5200, the electronic circuit system 5900 can exit a "low power" mode and increase the speed of communication with any surrounding computing devices (e.g., a mobile phone). In other embodiments, upon removal of the cover 5200, the electronic circuit system 5900 can activate and/or increase the sample rate for any of the sensors (e.g., the accelerometer) to improve the likelihood of receiving data associated with an injection event. Similarly stated, in some embodiments, the removal of the cover 5200 (i.e., the signal produced by the cover switch 5974) causes other portions and/or modules of the electronic circuit system 5900 to exit a dormant or "sleep" mode.

Figure 36:
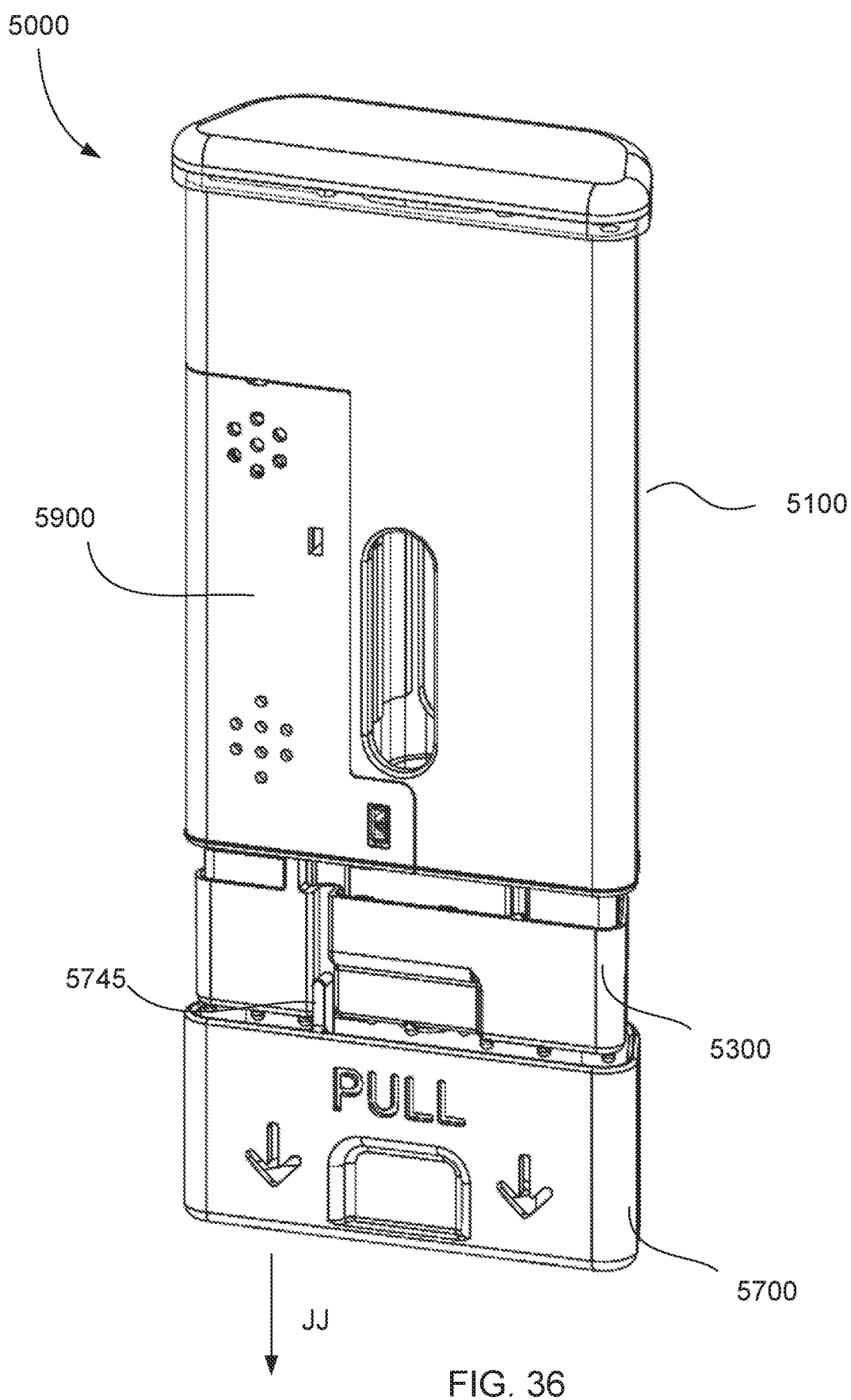
Figure 37:
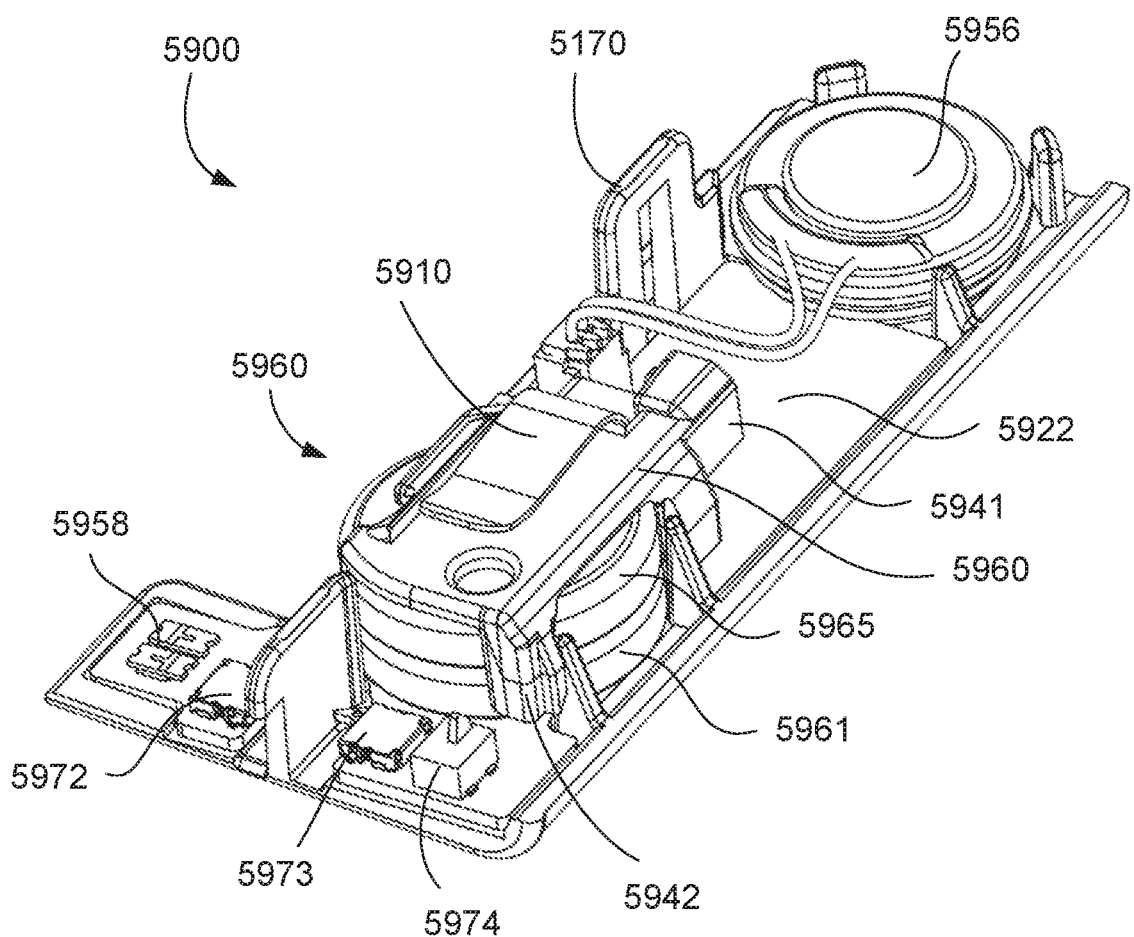
FIGS. 37 and 38 are perspective views of an electronic circuit system of the medical injector shown in FIG. 35.

The first (or safety) switch 5972 is actuated when the safety lock 5700 is moved from a first position to a second position (see e.g., the arrow JJ in FIG. 36). Specifically, when the safety lock 5700 is removed, a protrusion 5745 of the safety lock 4700 engages and/or actuates the first switch 5972. Upon actuation of the safety switch 5972, the processor 5980 and/or any of the modules described herein can produce any of the electronic outputs described herein (e.g., audible, visual, wireless, or the like), can change the communication mode of the radio, and/or otherwise interact with a connected health medicament delivery system. For example, in some embodiments, upon removal of the safety lock 5700, the electronic circuit system 5900 can increase the broadcasting interval to improve the likelihood of pairing with any surrounding computing devices (e.g., a mobile phone).

The second (or actuation) switch 5973 is actuated when the base 5300 is moved from its first position to its second position. Specifically, the proximal movement of the actuator 5300 causes a protrusion (not shown) of the base to engage and/or actuate the second switch 5973. Upon actuation of the actuation switch 5973, the processor 5980 and/or any of the modules described herein can produce any of the electronic outputs described herein (e.g., audible, visual, wireless, or the like), can change the communication mode of the radio, and/or otherwise interact with a connected health medicament delivery system (e.g., the system 5800). For example, in some embodiments, upon movement of the base (or actuator) 5300, the electronic circuit system 5900 can increase the speed of communication with any surrounding computing devices (e.g., a mobile phone), can send a signal confirming actuation of the device 5000, or the like.

In other embodiments, upon movement of the base 5300, the electronic circuit system 5900 can activate a use module (also referred to as an event detection module, see e.g., the event detection or "use" module 7982). As described herein, the use module 7982 is configured to multiple signals (from at least two different sensors of the electronic circuit system 5900) to verify than an actual injection even occurred and produce a notification associated with the actual injection.

The audio output device 5956 of the electronic circuit system 5900 is configured to output audible sound to a user in response to a use of the medical injector 5000. In some embodiments, the audible output device 5956 can be a speaker. In some embodiments, the audible sound can be, for example, associated with a recorded message and/or a recorded speech. In other embodiments, the audible instructions can be an audible beep, a series of tones and/or or the like.

The light emitting diodes (LEDs) 5958 can be similar to the LEDs shown and described herein, and can produce visual outputs in response to a use of the medicament delivery device 5000.

In addition to the switches, the electronic circuit system 5900 also includes a temperature sensor and an accelerometer. The temperature sensor can be any suitable temperature sensing device, and can provide input to the processor regarding the current temperature of the medicament delivery device 5000, the temperature history of the device or the like. The accelerometer can be any suitable accelerometer, and can provide input to the processor regarding the movement and/or vibration of the medicament delivery device 5000. For example, in some embodiments, the accelerometer can be a three-axis accelerometer that provides movement and/or vibration information along each of the three axes of the device 5000. In this manner, the accelerometer data can be used to detect changes in orientation, etc. Based on the movement/vibration input the processor can execute any of the modules and/or execute any of the methods described herein, such as for example, the motion (or leash) module to implement "soft leashing" or "carry detection" methods as described herein or the "event detection" methods described herein. In this manner, the electronic circuit system 5900 can produce a signal (audible, wireless, visual, or the like) that confirms the actual actuation of the device.

Although the series of sensors described herein includes switches, a temperature sensor, and an accelerometer, in other embodiments, the electronic circuit system 5900 (and any of the electronic circuit systems described herein) can include any suitable sensor. Specifically, any of the sensors described herein can be any suitable electronic device that receives a physical input (e.g., a change in position, temperature, or pressure) and produces an electronic output in response. For example, although one of the sensors described above is an actuation switch 5973, in other embodiments, the movement of the base 5300 can be measured by any other suitable sensor, such as, for example, a linear position sensor (e.g., an LVDT or the like).

Moreover, in some embodiments power management techniques, such as time multiplexing can be executed by the processor (or any of the processors described herein). Such power management methods can be performed, for example, by a power management module (see, e.g., the power management module 7987). For example, the processor 5980 can be operable to manage power draw such that high-draw and/or processor intensive operations, such as voice processing and operating the radio are not executed simultaneously. For example, in some embodiments, a method can include delaying and/or extending a communication interval during a time period when operations involving a recorded speech output via the speaker 5956 and/or a light output device 5958 are performed. In other embodiments, a method can include changing a communication mode during a time period when operations involving a recorded speech output via the speaker 5956 and/or a light output device (not shown) are performed. For example, in some embodiments, a method can include transitioning the device to a sniff or park mode upon activation of the device to conserve power draw from the instruction features of the device.

In yet other embodiments, the processor 5980 and/or the power management module can disable wireless communications when the power level of the battery assembly 5960 drops below a threshold value, as described herein.

Figure 42:
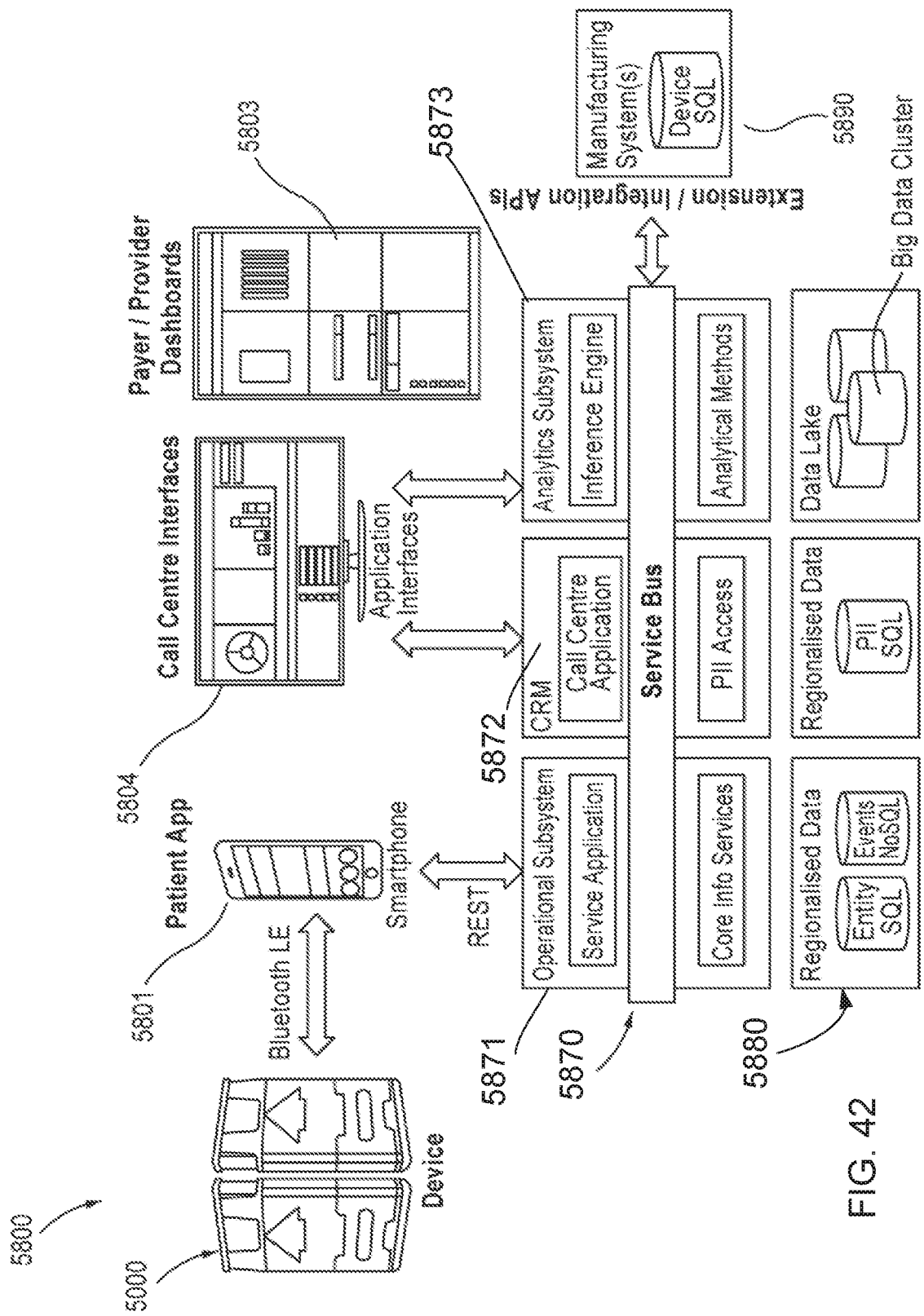
FIG. 42 is a schematic illustration of a connected health medicament delivery system, according to an embodiment.

In some embodiments, the medicament delivery device 5000 and any of the devices or drug products described herein can be included as a part of a connected health medicament delivery system. For example, FIG. 42 is a schematic illustration of a connected health medicament delivery system (also referred to as a connected health system) 5800, according to an embodiment. The connected health medicament delivery system 5800 includes at least one medicament delivery device 5000 (or any other medicament delivery device of the types described herein), an external (or remote) computing device 5801, a remote (or call center) interface 5804, a remote (or payer/provider) interface 5803, a service platform 5870, and a database platform 5880. The components, modules, and/or functions described in connection with the connected health system 5800 can be included within any of the connected health systems described herein. For example, any of the connected health systems described herein (such as the connected health systems 6800, and 7800) can include the payer/provider interface 5803, the database platform 5880 and/or the service platform 5870. Moreover, although the connected health system 5800 is shown and described as including at least one medicament delivery device 5000, in other embodiments, the connected health system 5800 (and any of the connected health systems described herein) can include any of the medicament delivery devices (or drug products) shown and described herein. Similarly, the connected health system 5800 (and any of the connected health systems described herein) can include any of the remote computing devices described herein, such as, for example, the remote computing devices 7801, 7802 described below.

The connected health system 5800 and any components therein (including any of the functional modules) can perform any of the methods described herein, including methods related to "leashing" the device 5000 to the user, tracking whether the user is consistently carrying the device 5000, power management methods, and/or event detection methods. For example, although certain methods are described as being performed by a processor of the external computing device 5801 (or the remote device 7801), in some embodiments, such methods can be performed by a processor of the medicament delivery device 5000 (or the device 7000), a processor within the service platform 5870 (or the service platform 7870; i.e., "in the cloud"), or in any combination of the processors in the remote computing device, the medicament delivery device, and the service platform.

As described herein, the external (or remote) computing device 5801 (e.g., either the user's mobile computing device or the patient's mobile computing device) can be configured to transmit and/or receive a signal (indicated by the arrow "Bluetooth LE" in FIG. 42) to and/or from the medicament delivery device 5000. The signal can be transmitted and/or received by any of the methods described herein. For example, in some embodiments, the signal is received after the computing device 5801 is used to scan a label, tag or other machine-readable code on (or associated with) the medicament delivery device 5000. For example, as described below, in some embodiments, the computing device 5801 can be used to photograph a container or packaging within which the medicament delivery device 5000 is stored. In this manner, a signal is received (via the photograph) that provides information related to the specific medicament delivery device (e.g., the serial number, the manufacturing lot number, etc.). In some embodiments, the signal (and/or information) can be received from the photograph by an optical character recognition (OCR) algorithm. In other embodiments, the signal can be received automatically (e.g., without the need to scan a code). For example, in some embodiments, the electronic circuit system 5900 of the medicament delivery device 5000 can transmit a signal to the computing device 5801 in response to the manipulation of the medicament delivery device 5000 (removal of the cover 5200, removal of the safety lock 5700, movement of the base 5300). Specifically, the radio and/or wireless communication module of the electronic circuit system 5900 produces a wireless signal in response to actuation of the switches therein (e.g., switches 5972, 5973, and 5974). Upon receiving the signal, the computing device 5801 can then transmit visual and/or audible instructions for using the medicament delivery device 5000. The computing device 5801 can produce the audible and visual instructions according to any of the methods described herein. Specifically, the computing device 5801 (and any of the remote computing devices described herein) can include any of the modules described herein, including, for example, the network module 7814, the notification module 7817, and/or the event detection module 7812 described below. In this manner, the computing device 5801 can produce notifications using sounds and/or any of the graphical user interface elements, as described herein. Moreover, as described below with reference to the user interface 7820, the computing device 5801 can also receive input (e.g., via a touchscreen, a microphone or the like). This input can be used to send additional instructions and/or signals (to the service platform 5870, the medicament delivery device 5000, or other devices within the system). This arrangement allows the computing and/or communication resources of the communication device to be used to enhance the instructions, locating capabilities and/or the like of the systems described herein.

The external (or remote) computing device 5801 can also be operable to display e.g., via a visual output device, or emit, e.g., via an audible output device, information and/or instructions regarding the patient's medical history and/or the administration of medicament using the medicament delivery device 5000. For example, in some embodiments, the computing device 5801 (and any of the remote computing devices described herein) can include an on-boarding module (e.g., the on-boarding module 7819) through which the patient can "opt in" to allow sharing of medical history, patient-specific data, and the like.

The external (or remote) computing device 5801 can also automatically contact emergency personnel and/or prompt the patient and/or the user to contact emergency personnel. For example, in some embodiments, the external (or remote) computing device 5801 can execute an application (of the types described herein) that can unlock and/or otherwise configure the cell phone to be used by the patient and/or the user to facilitate the methods of the connected health medicament delivery system 5800. In some embodiments, the external (or remote) computing device 5801 can automatically display a prompt and/or instruction (see, e.g., the graphical user interface elements described herein) upon detecting a specified condition (e.g., a delivery event, as detected by an event detection module). Thus, in those embodiments in which the external (or remote) computing device 5801 is a cell phone, the cell phone can be configured to be useable and/or provide information to the user in the event of a medical emergency without requiring a password or unlock sequence. For example, in some embodiments, the touch screen of the cell phone can display a button in response to the detection of a specified condition that prompts a user (e.g., a third party) to enter the application. In other embodiments, the cell phone can display a message prompting the user to "swipe," scan or read a particular code thereby unlocking the cell phone for subsequent use as described herein. For example, in some embodiments, the user can be prompted to swipe, scan or read an identification card, another device, a medicament container or the like. For example, in some embodiments, the user can be prompted to take a photograph of an identification card, and information can be from the photograph by an optical character recognition (OCR) algorithm.

In some embodiments, the computing device 5801 can be equipped with a global positioning sensor and can be configured to automatically transmit location information to emergency personnel when use of the device 5000 is detected (e.g., by the use module, as described herein). For example, the computing device 5801 can run one or more application modules (e.g., executed by a processor of the device 5801) that can, upon detection of a medicament delivery event, access the location information of the computing device 5801 and send this information directly to the software platform of the emergency service provider. Such additional information can be displayed along with the traditional network information associated with the computing device 5801 that is provided during a traditional emergency call (e.g., an approximate location). By automatically providing more exact location information—and specifically location information that is commensurate in time with the detected delivery event—the connected health system 5800 can improve response times and outcomes.

In some embodiments, the computing device 5801 can be used to transmit a signal to the medicament delivery device 5000. For example, in some embodiments, the computing device 5801 can transmit a short-range wireless signal to establish and/or maintain a communication link with the medicament delivery device 5000. For example, the computing device 5801 and the electronic circuit system 5900 can be paired via the Bluetooth® wireless protocol. Similarly stated, the computing device 5801 and the electronic circuit system 5900 can be paired via a wireless protocol that facilitates the transmission of signals within a range of approximately 100 meters or less (i.e., a Class 3 radio) and/or having a frequency within the range of 2400 MHz and 2480 MHz.

Although the external communication (or computing) device 5801 is described primarily as being a mobile phone, in other embodiments, the external computing device 5801 can be any suitable device configured to communicate with the electronic circuit system 5900 and/or the medicament delivery device. For example, in some embodiments, the external computing device 5801 (or any of the computing/communication devices that receive signals from the medicament delivery device 5000) can be any suitable monitoring device or locator, such as the monitoring device 150 shown and described in U.S. Patent Publication No. 2014/0243749, entitled "Devices, Systems and Methods for Interacting with Medicament Delivery Systems" filed on Dec. 27, 2013, the disclosure of which is incorporated herein by reference in its entirety. For example, in some embodiments, the external computing device 5801 can be a bracelet, a necklace, a keychain fob, a watch, a ring, an adhesive patch, or other personal electronic device, and/or any other suitable object. The external computing device 5801 can be a piece of jewelry and/or integrated into a piece of jewelry, such as a necklace or bracelet. The external computing device 5801 can be a fitness tracker and can incorporate the motion sensing capabilities of the fitness tracker to ensure compliance and the desired level of "carrying" of the medicament delivery device 5000. In some embodiments, however, the external computing device 5801 can be inconspicuous, so as to not draw attention to the user. For example, in some embodiments, the external computing device 5801 can be similar to and/or incorporated within an article that is inconspicuous. For example, in some embodiments, the external computing device 5801 can be located on an inner layer of clothing, incorporated or manufactured as a part of the clothing, incorporated into a common accessory, fabricated to resemble a standard key fob, or the like. Such devices can, for example, retain the data and/or information transmitted by the medicament delivery device 5000 until such time as the user is within range of a mobile phone or other more sophisticated computing device.

In some embodiments, the external computing device 5801 (or any of the computing/communication devices that receive signals from the medicament delivery device 5000) can be a docking station (e.g., within the user's home). The docket station can also function to be physically coupled to the medicament delivery device 5000, for example, to recharge the device. In some embodiments, the external computing device 5801 (or any of the computing/communication devices that receive signals from the medicament delivery device 5000) can be a network hub for a community of users, a link to the network (or cloud), or any other suitable communication device.

Although the connected health system 5800 is shown as including only one remote computing device 5801, in other embodiments, the connected health system 5800 (and any of the connected health systems described herein) can include any number of remote computing devices 5801. For example, in some embodiments, the connected health system 5800 includes a first remote computing device 5801 that belongs to the patient and that can be wirelessly coupled to the medicament delivery device(s) 5000 via a short-range protocol, as shown in FIG. 42. The connected health system 5800 can include a second remote computing device (not shown) that belongs to an emergency contact associated with the patient (e.g., the patient's parent), and/or a third remote computing device (not shown) that belongs to a caregiver associated with the patient (e.g., a school nurse, a doctor, or the like). Such additional devices can either establish and/or maintain a communication link with the medicament delivery device 5000 (similar to the first device 5801 described above) or receive information associated with the medicament delivery device 5000 via the service platform 5870, which can be communicatively coupled to any of the remote computing devices or interfaces by a network (e.g., the network 1805 described herein).

In addition to the remote computing device 5801, the connected health system 5800 also includes the remote (or call center) interface 5804. The call center interface 5804 can be any suitable computer-implemented interface and/or computing entity, such as a server or personal computer, that transmits and/or receives information to and/or from the service platform 5870. The call center interface 5804 can include any suitable hardware and/or software modules. The call center interface 5804 can be communicatively coupled to the service platform 5870 and/or a customer relationship management (CRM) module 5872 within the service platform 5870 by a network (e.g., the network 1805 described herein).

The connected health system 5800 also includes the remote (or payer/provider) interface 5803. The payer/provider interface 5803 can be any suitable computer-implemented interface and/or computing entity, such as a server or personal computer, that transmits and/or receives information to and/or from the service platform 5870. The payer/provider interface 5803 can include any suitable hardware and/or software modules. For example, in some embodiments, the payer/provider interface 5803 can include one or more analytics modules configured to receive and/or process data stored by the payer (e.g., an insurance company) that is specific to the patient. The payer/provider interface 5803 can be communicatively coupled to the service platform 5870 and/or an analytics system 5873 within the service platform 5870 by a network (e.g., the network 7805 described herein).

The service platform 5870 can be any suitable computer-implemented interface and/or computing entity, such as a server or personal computer, that is configured to communicate with the remote computing device(s) 5801, the call center interface 5804, the payer/provider interface 5803, the manufacturing system 5890, and/or any other portions of the connected health system 5800. More specifically, the service platform 5870 can receive information from devices within the connected health system 5800, manipulate the information, and produce information to any of the devices within the connected health system 5800. For example, in some embodiments, expiration information associated with the medicament delivery 5000 can be transmitted from the device 5000 to the patient's remote computing device 5801. The remote computing device 5801 can transmit the expiration information (e.g., via a network similar to the network 1805) to the service platform 5870. Based on the expiration information, the service platform 5870 (e.g., the operation subsystem 5871) can transmit notifications back to the patient's remote computing device 5801 to warn the user of an upcoming expiration date. In other embodiments, the service platform 5870 can receive motion profile information associated with each of the medicament delivery device 5000 and the remote computing device 5801 and process the information (e.g., in a compliance module) to determine whether the user has been carrying the medicament delivery device. In this manner, the service platform 5870 can control and/or manage certain notifications and/or features. Similarly stated, in this manner the service platform 5870 can function as the "back end" for the connected health system 5800. As shown, the service platform 5870 can be coupled to and/or access a database system 5880.

Figure 43:
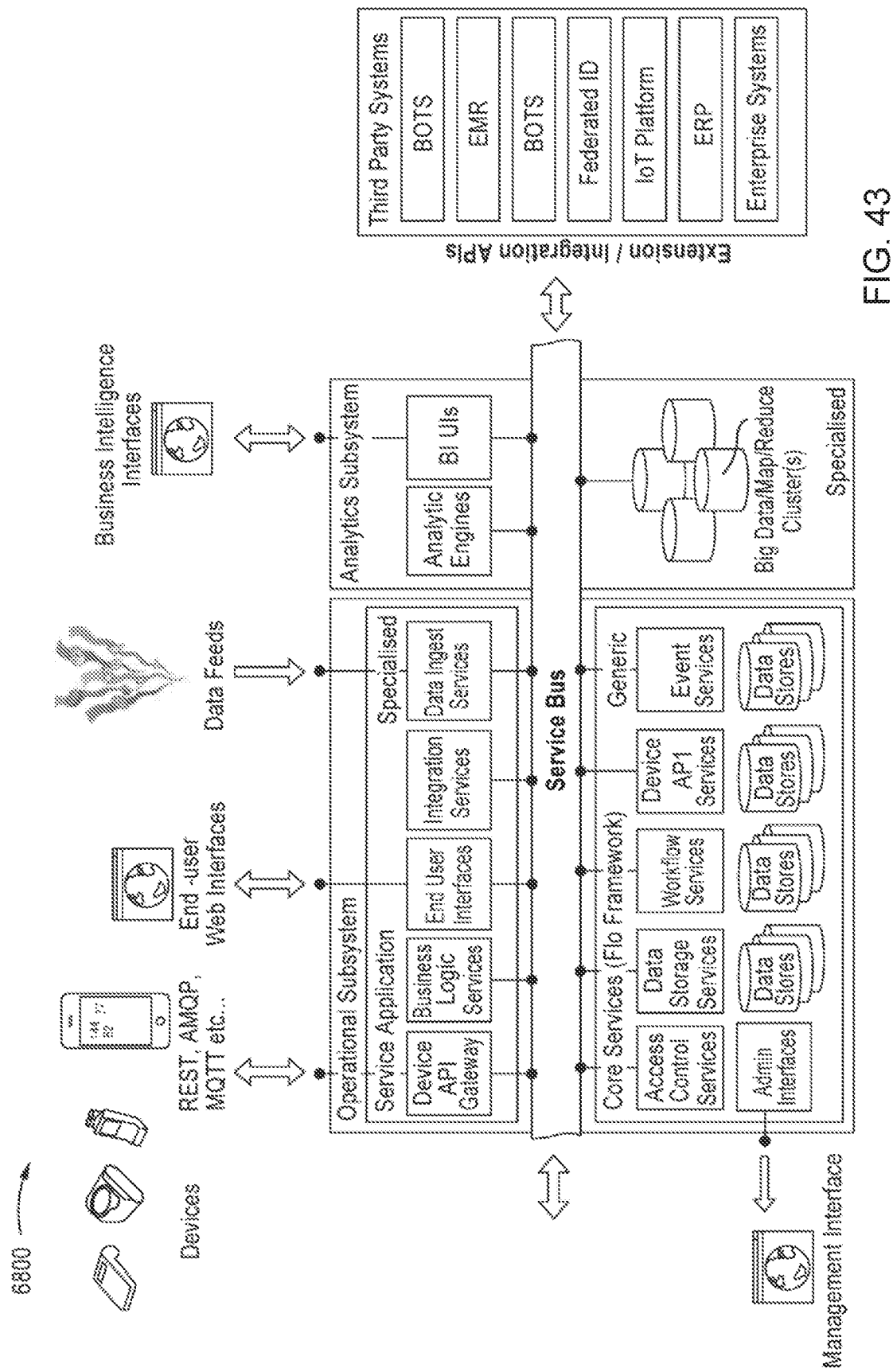
FIG. 43 is a schematic illustration of a connected health medicament delivery system, according to an embodiment.

FIG. 43 is a schematic illustration of a connected health medicament delivery system 6800, according to an embodiment. The connected health medicament delivery system 6800 includes at least one medicament delivery device (e.g., any medicament delivery device of the types described herein), at least one external (or remote) computing device (e.g., similar to the remote computing device 5801), and a series of interfaces. The remote computing devices and interfaces are coupled via a network (e.g., the network 7805) to a service platform and database system. The connected health system 6800 is similar to the connected health system 5800 described above, and is therefore not described in detail.

Figure 44:
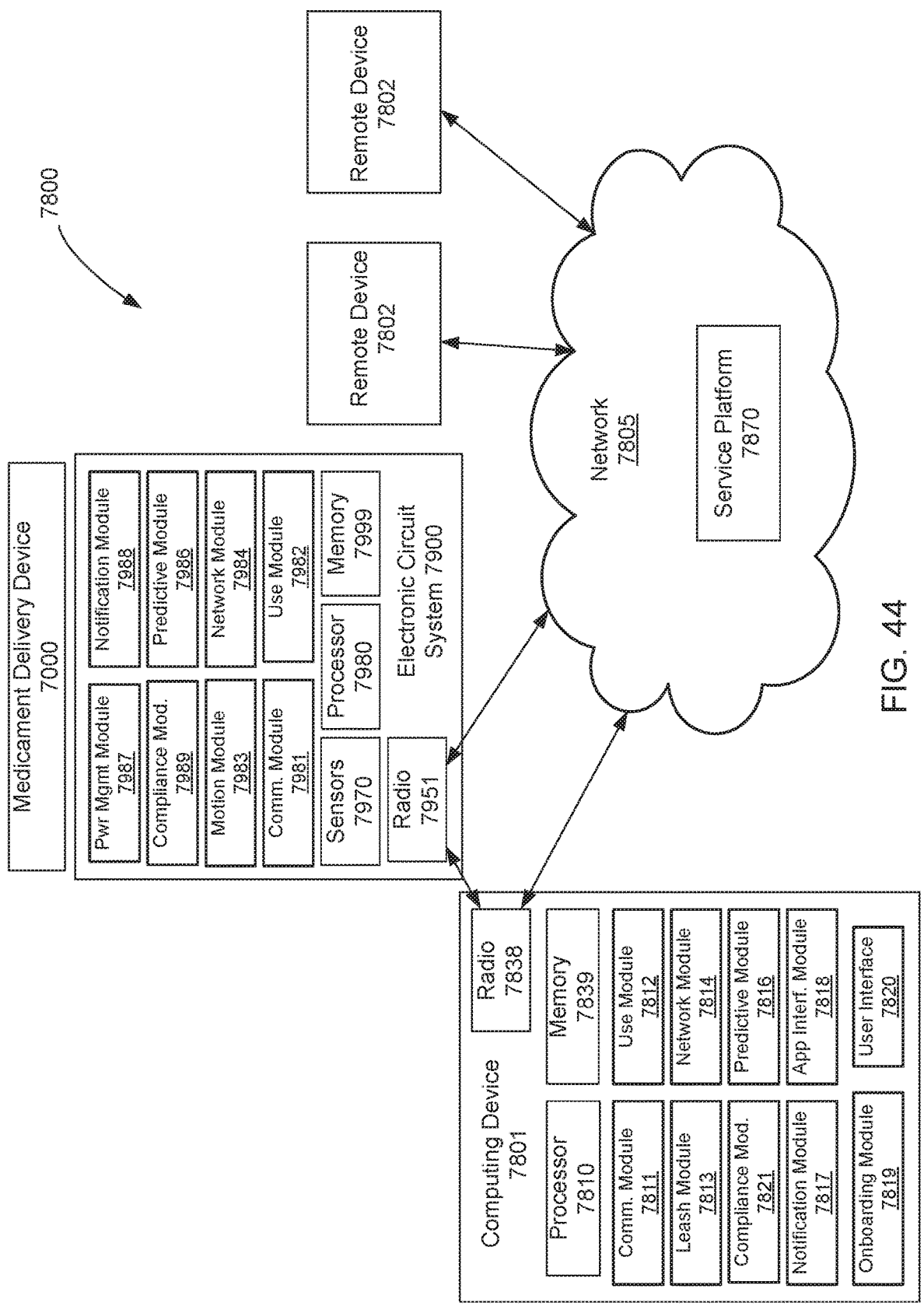
FIG. 44 is a schematic illustration of a connected health medicament delivery system, according to an embodiment.

FIG. 44 is a schematic illustration of a medicament delivery system 7800 (also referred to herein simply as "the system 7800" or "the connected health system 7800") according to an embodiment. The system 7800 includes a medicament delivery device 7000, an electronic circuit system 7900, a first remote computing device 7801, one or more second remote computing devices 7802, and a service platform 7870. Although not shown in FIG. 44, the service platform 7870. The components, modules, and/or functions described in connection with the connected health system 7800 can be included within any of the connected health systems described herein. Similarly, the components, modules and/or functions described in the other connected health systems described herein can be included in the connected health system 7800. For example, although not shown, the connected health system 7800 can include the payer/provider interface 5803 and the database platform 5880. Moreover, although the connected health system 7800 is shown and described as including two medicament delivery devices 7000 and 7000', in other embodiments, the connected health system 7800 (and any of the connected health systems described herein) can include any number of any of the medicament delivery devices (or drug products) shown and described herein. Similarly, the connected health system 5800 (and any of the connected health systems described herein) can include any number and any type of the remote computing devices described herein, such as, for example, the remote computing devices 5801, 5802 described below. The connected health system 7800 and any components therein (including any of the functional modules) can perform any of the methods described herein, including methods related to the soft leash (or motion detection) feature, the event (use) detection feature, and/or the computer application interface features described herein.

The service platform 7870 can be any suitable computer-implemented interface and/or computing entity, such as a server or personal computer, that is configured to communicate via the network 7805 with the remote computing device 7801, the remote computing devices 7802, and/or any other portions of the connected health system 7800 (e.g., a call center interface, a payer/provider interface, or the like). More specifically, the service platform 7870 can receive information from devices within the connected health system 7800, manipulate the information, and produce information to any of the devices within the connected health system 7800. For example, in some embodiments, expiration information associated with the medicament delivery 7000 can be transmitted from the device 7000 to the patient's remote computing device 7801. The remote computing device 7801 can transmit the expiration information (e.g., via the network 7805) to the service platform 7870. Based on the expiration information, the service platform 7870 can transmit notifications back to the patient's remote computing device 7801 and/or the remote computing devices 7802 (e.g., the parent's devices, an emergency contact's device, etc.) to warn the user of an upcoming expiration date. In this manner, the service platform 7870 can control and/or manage certain notifications and/or features. Similarly stated, in this manner the service platform 7870 can function as the "back end" for the connected health system 7800.

Although certain methods are described as being performed by a processor 7810 of the external computing device 7801 or the processor 7980 of the medicament delivery device 7900, in some embodiments, such methods can be performed by a processor of the service platform 7870 (i.e., "in the cloud"), or in any combination of the processors in the remote computing device, the medicament delivery device, and the service platform. Similarly stated, any of the modules described as be included within the electronic circuit system 7900 and/or the computing device 7801 can be included within the service platform 7870. For example, in some embodiments, the service platform 7870 can receive motion profile information associated with each of the medicament delivery device 7000 and the remote computing device 7801 and process the information (e.g., in a compliance module) to determine whether the user has been carrying the medicament delivery device 7000.

The network 7805 can be a piconet, the Internet, an intranet, a local area network (LAN), a wide area network (WAN), a virtual network, a telecommunications network, any other suitable communication system and/or combination of such networks. The network 7805 can be implemented as a wired and/or wireless network. Although FIG. 44 shows the medicament delivery device 7000 and the medicament delivery device 7000' being coupled to the network 7805 via the computing device 7801, in other embodiments, the medicament delivery device 7000 and the medicament delivery device 7000' can be coupled to (or connected with) the network via any suitable mechanism and/or by any protocol. For example, in some embodiments, the medicament delivery device 7000 and the medicament delivery device 7000' can be in direct communication with the network 7805, the remote devices 7802 and/or the service platform 7870 via the LTE Direct protocol or any other suitable protocol (e.g., the 5G mobile wireless standard based on the IEEE 802.11ac standard for broadband technology).

The medicament delivery device 7000 can be any of the medicament delivery devices described herein. In some embodiments, the connected health system 7800 can include multiple of the same medicament delivery device or multiple different medicament delivery devices (e.g., an epinephrine auto-injector, a rescue inhaler for asthma, a naloxone delivery device, or the like). The medicament delivery device 7000 can be an auto-injector similar to the auto-injector 4000 described below with reference to FIGS. 3-34 or the medicament delivery device 5000 described below with reference to FIGS. 35-41. In other embodiments, the medicament delivery device 7000 can be a pen injector (e.g., see FIGS. 1A-1C), a syringe, a nasal delivery device (such a nasal spray device), an inhaler (e.g., see FIG. 2), a device for delivering drugs to the buccal cavity, a body-worn drug delivery device, etc. In yet other embodiments, the device 7000 can be a simulated medicament delivery device (i.e., a device that is devoid of a medicament and/or that can simulate the use of a corresponding actual medicament delivery device).

The medicament delivery device includes or is attached to an electronic circuit system 7900. For example, in some embodiments, the electronic circuit system 7900 can be coupled to and/or within a housing, cover, case, and/or any other portion of the medicament delivery device. In other embodiments, the electronic circuit system 7900 can be integrated within the medicament delivery device 7000. For example, the electronic circuit system 7900 can be integrated within the auto-injector 4000 or the auto-injector 5000 (e.g., by being coupled to the housing 4170 and/or included within the housing 5100). The electronic circuit system 7900 includes a processor 7980, a memory 7999, one or more sensors (collectively identified as a sensor 7970), and a radio 7951. The electronic circuit system 7900 also includes a communication module 7981, a use (or history) module 7982, a leash (or motion tracking) module 7983, a network module 7984, a compliance module 7989, a predictive module 7986, a power management module 7987, and a notification module 7988. Although shown as including each of these application modules, in other embodiments, an electronic circuit system need not include all (or any) of these modules, and can include any other modules described herein. For example, in some embodiments, an electronic circuit system includes only a motion tracking module 7983, and is configured to perform the soft leash methods associated therewith, and need not include the use module 7982 or the communication module 7981. Alternatively, in other embodiments, an electronic circuit system includes only the use module 7982 and the communication module 7983. In such embodiments, the use module 7982 can detect a medicament delivery event and the communication module 7983 can produce a wireless signal associated with the actuation of the medicament delivery device 7000.

The processor 7980, and any of the processors described herein can be any suitable processor for performing the methods described herein. In some embodiments, processor 7980 can be configured to run and/or execute application modules, processes and/or functions associated with the medicament delivery system 7800. For example, the processor 7980 can be configured to run and/or execute the communication module 7981, the use (also referred to as an event detection) module 7982, the leash module 7983, and/or any of the other modules described herein, and perform the methods associated therewith. The processor 7980 can be, for example, a Field Programmable Gate Array (FPGA), an Application Specific Integrated Circuit (ASIC), a Digital Signal Processor (DSP), and/or the like. The processor 7980 can be configured to retrieve data from and/or write data to memory, e.g., the memory 7999. As described herein, in some embodiments, the processor 7980 can cooperatively function with the radio 7951 and/or execute instructions from code to provide signals to communicatively couple the electronic circuit system 7900 to the computing device 7801 (e.g., via wireless communication) and/or any other computing entity via a network 7805. In some embodiments, the processor 7980 is a Bluetooth® low energy (BLE) processor, such as The Texas Instruments® CC2540 series of processors, the Broadcom® BCM43341 processor, and/or any other processor suitable or configured specifically to execute the Bluetooth® v4.0 low energy stack. In other embodiments, the processor 7980 is a Bluetooth® low energy (BLE) processor, such as DA14581 processor, produced by Dialog Semiconductor. In other embodiments, the processor 7980 can include any of the processors or chipsets produced by Cambridge Silicon Radio Limited (CSR Ltd), including those in the CSR101x Product family. In yet other embodiments, the processor 7980 can include any of the Bluetooth® low energy (BLE) system on chip (SoC) produced by Nordic Semiconductor, including the nRF52840, the nRF52832, the nRF52810 chips.

In some embodiments, the processor 7980 (via the communication module 7981) can be operable to facilitate any suitable communication mode with the computing device 7801 and/or any other computing entity (e.g., by executing the communication module 7981). Such modes can include, for example, an active mode, hold mode, sniff mode, and/or park mode in accordance with the Bluetooth® wireless protocol. Moreover, the processor 7980 can also be operable to engage in any suitable type of data transfer, such as asynchronous connection-less logical transport (ACL), synchronous connection-oriented link (SCO), and/or any other suitable means.

The memory 7999 can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. In some embodiments, the memory 7999 stores instructions to cause the processor 7980 to execute modules, processes and/or functions associated with such medicament delivery system 7800 and/or the medicament delivery device 7000. For example, the memory 7999 can store instructions to cause the processor 7980 to execute any of the application modules described herein, and perform the methods associated therewith. In some embodiments, the memory 7999 stores information, such as one or more short-term or long-term security keys received from and/or exchanged with the remote computing device 7801 as a part of the pairing and/or bonding process.

The sensor(s) 7970 included within the electronic circuit system 7900 can include any number of switches, audible input sensors (e.g., a microphone), optical sensors, accelerometers, temperature sensors, contact sensors, and/or any other suitable input device. In some embodiments, the sensor(s) 7970 can include any of the sensors described above with reference to the electronic circuit system 4900 and/or the electronic circuit system 5900. For example, in some embodiments, the sensor(s) 7970 can include a sensor operable to monitor and/or measure the configuration and/or status of the medicament delivery device 7000. The sensor 7970 can be operable to detect if the medicament delivery device 7000 is removed from a case (such as the switch 5974 which detects removal of the outer cover 5200), if a safety lock is removed to "arm" the medicament delivery device 7000 (e.g., such as the switch 5972), if the medicament delivery device 7000 is actuated (i.e., to provide "delivery event" detection, such as that provided by the switch 5973), whether a temperature of the medicament has exceeded a threshold value, and so forth. For example, in some embodiments, the sensor 7970 can include a microphone operable to detect (e.g., in conjunction with the processor 7980) a mechanical and/or electronic sound associated with the actuation of the medicament delivery device, such as a characteristic hiss of a compressed gas container being discharged and/or a sound emitted from a speaker of the medicament delivery device 7000 (not shown). As yet another example, the sensor 7970 can include an optical sensor operable to detect the configuration of a status window of the medicament delivery device 7000, or the presence of light versus the absence of light (e.g., to detect whether component is blocking a beam). For example, the sensor 7970 can be operable to detect when a status window of the medicament delivery device 7000 turns color or opaque, which may be associated with use of the medicament delivery device 7000. As yet another example, the sensor 7970 can include an accelerometer (such as the accelerometer described above with reference to the device 5000) operable to detect a characteristic movement or vibration signature of the medicament delivery device 7000 when the device is actuated. As described herein, in some embodiments, the sensor 7970 can detect any of a position, a velocity, an acceleration, or an orientation of the medicament delivery device 7000 over a time period (e.g., 24 hours, 3 days, or the like). Based on the amount of motion, the leash or motion module 7983 (or compliance module 7989) can produce a motion profile that can be compared to a target motion profile unique to the medicament delivery device 7000 to determine whether the device is being carried as intended.

The radio 7951 (also referred to as a receiver, transmitter and/or transceiver) can be operable to send signals to, and/or receive radio signals, such as Bluetooth ZigBee, Wi-Fi, cellular telephone signals, etc. In some embodiments, such as embodiments where the processor 7980 is Bluetooth® processor, the radio 7951 can be integral with the processor 7980. In other embodiments, the radio 7951 can include a processor distinct from the processor 7980. In some embodiments, the radio 7951 can be operable to communicatively couple (also referred to herein as "linking," "pairing," or "bonding") the electronic circuit system 7900 to the computing device 7801 and/or any other computing entity via a network 7805. The radio 7951 can include or be coupled to a ceramic chip antenna, a stamped antenna, a sintered antenna, a PCB conductive trace antenna, and/or any other suitable antenna.

The communication module 7981 can be a hardware and/or software module (stored in memory 7999 and/or executed in the processor 7980). As described in more detail herein, the communication module 7981 is configured to receive an indication (e.g., from the sensor(s) 7970) and/or transition information associated with a change in status of the medicament delivery device 7000 and determine, based on the indication or the transition information, a connection and/or communications characteristic. Such communication characteristics can include, for example, a communication interval and/or connection interval (e.g., a time period between successive signals or portions of a signal, such an "advertising interval," also referred to herein as a "connection interval"), a communication mode (e.g., a park mode, sniff mode or the like), etc. In some embodiments, the communication module 7981 can function cooperatively with the power management module 7987 to reduce the power consumption of the electronic circuit system 7900 by modifying communication characteristics, suppressing certain communication signals produced by the electronic circuit system 7900, and/or disabling wireless communication.

The use (or event detection) module 7982 can be a hardware and/or software module (stored in memory 7999 and/or executed in the processor 7980). As described in more detail herein, in some embodiments, the use module 7982 is configured to receive multiple different actuation signals associated with the delivery of a medicament from the medicament delivery device 7000, and produce a notification confirming an "actual" delivery event. For example, in some embodiments, the use (or event detection) module 7982 can receive a first actuation signal in response to movement of an actuator (e.g., a signal from a switch similar to the switch 5973) and a second actuator signal from an accelerometer that is indicative of a vibration profile consistent with medicament delivery. The use module 7982 can then produce an event detection notification, which can be transmitted via the radio 7951 for receipt by the remote computing device 7801. In other embodiments, the use module can receive an indication (e.g., from the sensor 7970) and/or use information associated with a use or history of the medicament delivery device 7000 other than simply the device actuation, and produce a notification (e.g., a recorded speech instruction, signal for wireless transmission, or the like) based thereupon. In this manner, the use module 7982 can facilitate the electronic circuit system 7900 and/or the medicament delivery device 7000 (or simulated medicament delivery device) being a "smart" device that can produce updated instructions and/or guidance based on the history of usage. For example, in some embodiments, the use module 7982 can receive a cover removal signal in response to removal of the device 7000 from a cover (e.g., a signal from a switch similar to the switch 5974). When the number of instances of cover removal within a time period exceeds a threshold number, the use module can produce a notification (or script), which can be transmitted via the radio 7951 (i.e., a wireless communication signal) or transmitted via an audible output device. Such notification can, for example, remind the user to limit the number of cover removal instances to preserve battery power.

The leash (or motion) module 7983 can be a hardware and/or software module (stored in memory 7999 and/or executed in the processor 7980). As described in more detail herein, in some embodiments, the leash module 7983 is configured to receive information associated with the connection (or pairing) between the electronic circuit system 7900 and the computing device 7801 and produce an alarm based thereupon. In some embodiments, the leash module 7983 can base the alarms on the position and/or location of the electronic circuit system 7900 and/or the computing device 7801 or a combination of both. In other embodiments, the leash module 7983 can receive a motion signal (e.g. from a sensor, such as an accelerometer) and determine a motion profile associated with the medicament delivery device 7000. The motion profile can include, for example, an amount of the change over a period of time for any of a position, a velocity, an acceleration, or an orientation of the medicament delivery device 7000 (i.e., a housing the device, a cover within which the device is stored, or the like). In some embodiments, the motion module 7983 can provide such motion profile information for use by the leash module 7813, the compliance module 7841, or one or more corresponding leash modules or compliance modules of the service platform 7870 for use in determining whether the user has carried the medicament delivery device 7000. Thus, the motion module 7983 can collect data (e.g., from the accelerometer) that is used in such methods as described below.

In some embodiments, the leash module 7983 and/or the predictive module 7986 can learn or predict the user's behavior, and then adapt the leash notifications in response to conditions that deviate from the predicted behavior. Specifically, the predictive module 7986 can be a hardware and/or software module (stored in memory 7999 and/or executed in the processor 7980). In some embodiments, the predictive module 7986 can determine and/or change the target motion profile based on the motion profile received over a time period. For example, if the motion profile for a medicament delivery device 7000 that is designated as being carried by a patient consistently has a magnitude, amount and/or characteristic of motion at a certain level (e.g., a level consistent with being carried from the user's home to school over a certain distance, a certain number of times per day and/or at certain times of the day), then the predictive module 7986 can update a baseline target (or intended) motion profile to reflect an intended motion profile that is specific or unique to the user. In this manner, the predictive module 7986 can learn the user's behavior and modify the notifications produced based on the learned behavior.

The network module 7984 can be a hardware and/or software module (stored in memory 7999 and/or executed in the processor 7980). As described in more detail herein, the network module 7984 is configured to exchange information associated with the medicament delivery device 7000 and the remote computing device 7801 to facilitate the paring and/or bonding process. For example, the network module 7984 of the medicament delivery device 7000 can cause the remote computing device 7801 and the medicament delivery device 7000 to exchange short term and/or long term security keys to complete the pairing and bonding process.

The power management module 7987 can be a hardware and/or software module (stored in memory 7999 and/or executed in the processor 7980). As described in more detail herein, the power management module 7987 is configured to receive one or more signals from any of the sensors described herein and, based on the received signals, modify an electronic function (or output) of the electronic circuit system 7900 to preserve power. For example, in some embodiments, the power management module 7987 can modify an audible output to include a warning to the user when repeated removal of the cover is causing a power drain, and advise the user to limit any unnecessary cover removals. In other embodiments, the power management module 7987 can suppress and/or disable the audible output feature. For example, in some embodiments, a user can provide instructions (e.g., in response to a prompt presented via the mobile computing device 7801) to disable certain outputs, thereby improving power consumption. Specifically, in some embodiments, the user can select an output script from a set of output scripts to be produced by the electronic circuit system 7900 when the device is used. For a chronic care device where the user is familiar with operation of the device, the user may suppress the instruction scripts and only select a countdown timer for use. Similarly stated, in some embodiments, the power module 7987 or an output module (or any other modules described herein) can modify the default output script in response to a wireless signal received by the electronic circuit system. In other embodiments, the power management module 7987 (or an output module) can receive a signal directly from the service platform 7870 (e.g. and not via the mobile computing device 7801) and can adjust the output script in response to the signal. Although described as modifying an audible output, in other embodiments, the power management module 7987 can modify any of the electronic outputs described herein, such as, for example, the wireless communication signals produced by the radio 7951, any of the visual outputs described herein, a haptic output or the like.

The notification module 7988 can be a hardware and/or software module (stored in memory 7999 and/or executed in the processor 7980). As described in more detail herein, the notification module 7988 is configured to produce notifications associated with any of the methods and/or application modules described herein. For example, in some embodiments, the notification module 7988 can produce a notification that is transmitted via the radio 7951 and is for receipt by the notification module 7817 of the remote computing device 7801. In this manner, the notification module 7988 and/or the notification module 7817 can produce outputs (e.g., wireless communication signals, GUI elements, audible outputs, visual outputs, or the like) to notify the user, patient, or account administrator of events. In other embodiments, the notification module 7988 can produce a notification that is transmitted via the radio 7951 directly to the service platform 7870. In this manner, the service platform 7870 can update various dashboards, databases and the like based on information received from the medicament delivery device 7000. Whether received directly or via the remote computing device 7801, the service platform 7870 can update information in any of the database systems or dashboards described herein (e.g., the operation subsystem 5871 the database system 5880, or any suitable systems described herein).

The computing device 7801 (or other "remote" computing devices, such as the device 5801 described below) can be a mobile computing entity, such as a smart mobile phone (e.g., an iPhone®, an Android® device, a Windows® phone, a Blackberry® phone, etc.), a tablet computer (e.g., an Apple iPad®, a Samsung Nexus® device, a Microsoft Surface® device, etc.), or a computer (e.g., a laptop, desktop, smart TV, etc.), and/or any other suitable computing entity. Although described primarily as a smartphone, the computing device 7801 can be a bracelet, a necklace, a keychain fob, a watch, a ring, an adhesive patch, or other personal electronic device, and/or any other suitable object. The external computing device 5801 can be a fitness tracker and can incorporate the motion sensing capabilities of the fitness tracker to ensure compliance and the desired level of "carrying" of the medicament delivery device 7000. The computing device 7801 includes a processor 7810, a memory 7839, a user interface 7820, and a radio 7838.

The computing device 7801 also includes a communication module 7811, a use (or history) module 7812, a leash (or motion tracking) module 7813, a network module 7814, a compliance module 7821, a predictive module 7816, a notification module 7817, an application interface module 7818, and an onboarding module 7819. Although shown as including each of these application modules, in other embodiments, a computing device need not include all (or any) of these modules, and can include any other modules described herein. For example, in some embodiments, the computing device 7801 includes only a motion tracking module 7813, and is configured to perform the soft leash methods associated therewith, and need not include the use module 7812 or the other application modules listed above. Alternatively, in other embodiments, the computing device 7801 includes only the use module 7812 and the notification module 7817. In such embodiments, the use module 7812 can detect a medicament delivery event (e.g., via a wireless signal from the electronic circuit system 7900 of the device 7000) and the notification module 7817 can produce an instruction, a GUI element, or the like associated with the actuation of the medicament delivery device 7000.

The processor 7810 can be, for example, a FPGA, an ASIC, a DSP, and/or the like. The processor 7810 can be configured to retrieve data from and/or write data to memory, e.g., the memory 7839, which can be, for example, RAM, memory buffers, hard drives, databases, EPROMs, EEPROMs, ROM, flash memory, hard disks, floppy disks, cloud storage, and/or so forth. In some embodiments, processor 7810 can be configured to run and/or execute application modules, processes and/or functions associated with the medicament delivery system 7800 (or any of the medicament delivery systems described herein). For example, in some embodiments, the processor 7810 can be configured to run and/or execute the communication module 7811, the use (or history) module 7812, the leash (or motion tracking) module 7813, the network module 7814, the compliance module 7821, the predictive module 7816, the notification module 7817, the application interface module 7818, and the onboarding module 7819, and/or any of the other modules described herein, and perform the methods associated therewith.

The user interface 7820 can be, for example, a monitor or screen that displays visual elements to a user. The user interface 7820 can be a touch screen (of a smart mobile phone) upon which a series of graphical user interface (GUI) elements (e.g., windows, icons, input prompts, graphical buttons, data displays, notification, or the like) can be displayed. In some embodiments, the graphical user interface elements (see e.g., the GUI elements described with reference to FIGS. 57-89, 92, 93, and 96-110 of U.S. Pat. No. 10,332,623, entitled "Medicament Delivery Devices with Wireless Connectivity and Event Detection," filed Jan. 16, 2018, which is incorporated herein by reference in its entirety) are produced by the notification module 7817, the onboarding module 7819, the network module 7814 or any of the other application modules. The user interface 7820 can also include an audible output device through which a series of audible outputs can be produced. Moreover, the user interface 7820 can also receive input from the user, such as, for example, input via a touch screen, input via a microphone, or the like.

The radio 7838 can be any suitable communication device and can be a part of the overall processor architecture, (e.g., a part of the Bluetooth® processor). In other embodiments, the radio 7838 can be distinct from the processor 7810. In some embodiments, a short-range radio link can be established between the computing device 7801 and the electronic circuit system 7900. For example, the computing device 7801 and the electronic circuit system 7900 can be paired via the Bluetooth® wireless protocol. Similarly stated, the computing device 7801 and the electronic circuit system 7900 can be paired via a wireless protocol that facilitates the transmission of signals within a range of approximately 700 meters or less (i.e., a Class 3 radio) and/or having a frequency within the range of 2400 MHz and 2480 MHz. In such an embodiment, as described in further detail herein, the computing device 7801 can be operable to send and/or receive data from the electronic circuit system 7900 related to the medicament delivery device 7000, such as data associated with use, preparation for use, status, and so forth. Furthermore, the electronic circuit system 7900 and/or the computing device 7801 can be operable to determine when a short-range communication link is broken (e.g., when the electronic circuit system 7900 is out of range of the computing device 7801).

In some embodiments, such as an embodiment where the computing device 7801 is a Bluetooth® enabled mobile phone, the radio 7838 can be suitable to establish a short-range radio link with the electronic circuit system 7900 and establish a long-range with another computing device (e.g., the remote device 7802) via the network. For example, the radio 7838 can be a dual-function radio and/or the computing device 7801 can include multiple radios to relay information associated with the electronic circuit system 7900 (which may be equipped with only a short-range radio) to the remote device 7802 using, for example, a cellular data network and/or a Wi-Fi link to the Internet. In other embodiments, the electronic circuit system 7900 may be equipped with a radio operable to communicate with the remote device 7802 via the network 7805.

The computing device 7801 can be operable to store (e.g., in the memory 7839) information associated with the electronic circuit system 7900, such as connection time, a medicament device 7000 use record, details of a medicament delivery event (e.g., date, time, duration, and any other characteristics of the use) and so forth. In some embodiments, the computing device 7801 can be operable to determine its location (e.g., via a global positioning system (GPS) sensor (not shown)). In such an embodiment, the computing device 7801 can be operable to associate location data with information associated with the electronic circuit system 7900, such as use data.

The communication module 7811 can be a hardware and/or software module (stored in memory 7839 and/or executed in the processor 7810). In some embodiments, the communication module 7811 is configured to receive an indication and/or transition information associated with a change in status of the medicament delivery device 7000 (e.g., via a wireless signal from the electronic circuit system 7900) and determine, based on the indication or the transition information, a connection and/or communications characteristic. Functions of the communication module 7811 are described in U.S. Pat. No. 10,332,623, entitled "Medicament Delivery Devices with Wireless Connectivity and Event Detection," filed Jan. 16, 2018, which is incorporated herein by reference in its entirety.

The use (or event detection) module 7812 can be a hardware and/or software module (stored in memory 7839 and/or executed in the processor 7810). As described in more detail herein, in some embodiments, the determination of whether an actual delivery event has occurred is performed solely by the use (or event detection) module 7982 of the device 7000. In other embodiments, certain event detection methods can be performed by the use module 7812 of the remote computing device 7801.

Although the motion tracking or leash methods are described as being performed by the leash (or motion) module 7983, which is a part of the electronic circuit system 7900, in other embodiments, all or a portion of the leash (or motion tracking) methods can be performed by the leash module 7813, which is included within the remote computing device 7801, or a leash module within the service platform 7870. Functions of the leash module 7983 are described in U.S. Pat. No. 10,332,623, entitled "Medicament Delivery Devices with Wireless Connectivity and Event Detection," filed Jan. 16, 2018, which is incorporated herein by reference in its entirety.

In some embodiments, the leash module 7813 and/or the predictive module 7816 can learn or predict the user's behavior, and then adapt the leash notifications in response to conditions that deviate from the predicted behavior. Specifically, the predictive module 7816 can be a hardware and/or software module (stored in memory 7839 and/or executed in the processor 7810). In some embodiments, the predictive module 7816 can determine and/or change the target motion profile based on the motion profile received over a time period. For example, if the motion profile for a medicament delivery device 7000 that is designated as being carried by a patient consistently has a magnitude, amount and/or characteristic of motion at a certain level (e.g., a level consistent with being carried from the user's home to school over a certain distance, a certain number of times per day and/or at certain times of the day), then the predictive module 7816 can receive such information (e.g., via wireless signals from the medicament delivery device 7000) and update a baseline target (or intended) motion profile to reflect an intended motion profile that is specific or unique to the user. In this manner, the predictive module 7816 can learn the user's behavior and modify the notifications produced based on the learned behavior.

The network module 7814 can be a hardware and/or software module (stored in memory 7839 and/or executed in the processor 7810). As described in more detail herein, the network module 7814 is configured to exchange information associated with the medicament delivery device 7000 and the remote computing device 7801 to facilitate the paring and/or bonding process.

The application interface module 7818 can be a hardware and/or software module (stored in memory 7839 and/or executed in the processor 7810). As described in more detail herein, the application interface module 7818 is configured to exchange information with other applications external to the connected health system 7800. In this manner, the connected health system 7800 can utilize information from other computer-based applications or systems to enhance the performance of the connected health system 7800. For example, in some embodiments, the remote computing device 7801 can execute a first application (e.g., that includes any of the application modules described herein, such as the leash module 7813, the network module 7814, and/or the onboarding module 7819) and a second application (not shown in FIG. 44) that is different from the first application. The first application and/or the second application can be configured to run on any suitable platform or operating system, such as Apple iOS, Android (used by certain phones produced by Samsung), Symbian OS (used by certain phones produced by Nokia), Blackberry OS, or Windows OS. The first application is a part of the connected health system 7800, and can communicate with the medicament delivery device 7000, present information to, and receive information from the user via the remote computing device 7801 (e.g., via any of the graphical user interface elements described herein). The second application can be any other application that is executed by the processor 7810 and/or stored within the memory 7839 of the remote computing device 7801. For example, in some embodiments, the second application can be a non-browser application (i.e., the main purpose of the second application is something other than to contact sites on the internet on request).

In some embodiments, the second application is an application associated with delivery of information via an emergency call platform. For example, in some embodiments, the second application can be configured to automatically transmit location information to emergency personnel when the device 7801 initiates an emergency call. Thus, the application interface module 7818 can transmit information associated with the use of the device 7000 (e.g., from the use module), thus allowing the second application to initiate an emergency call, transmit location information directly to the emergency data platform, or the like. By automatically providing more exact location information—and specifically location information that is commensurate in time with the detected delivery event—the connected health system 7800 can improve response times and outcomes.

Figure 45:
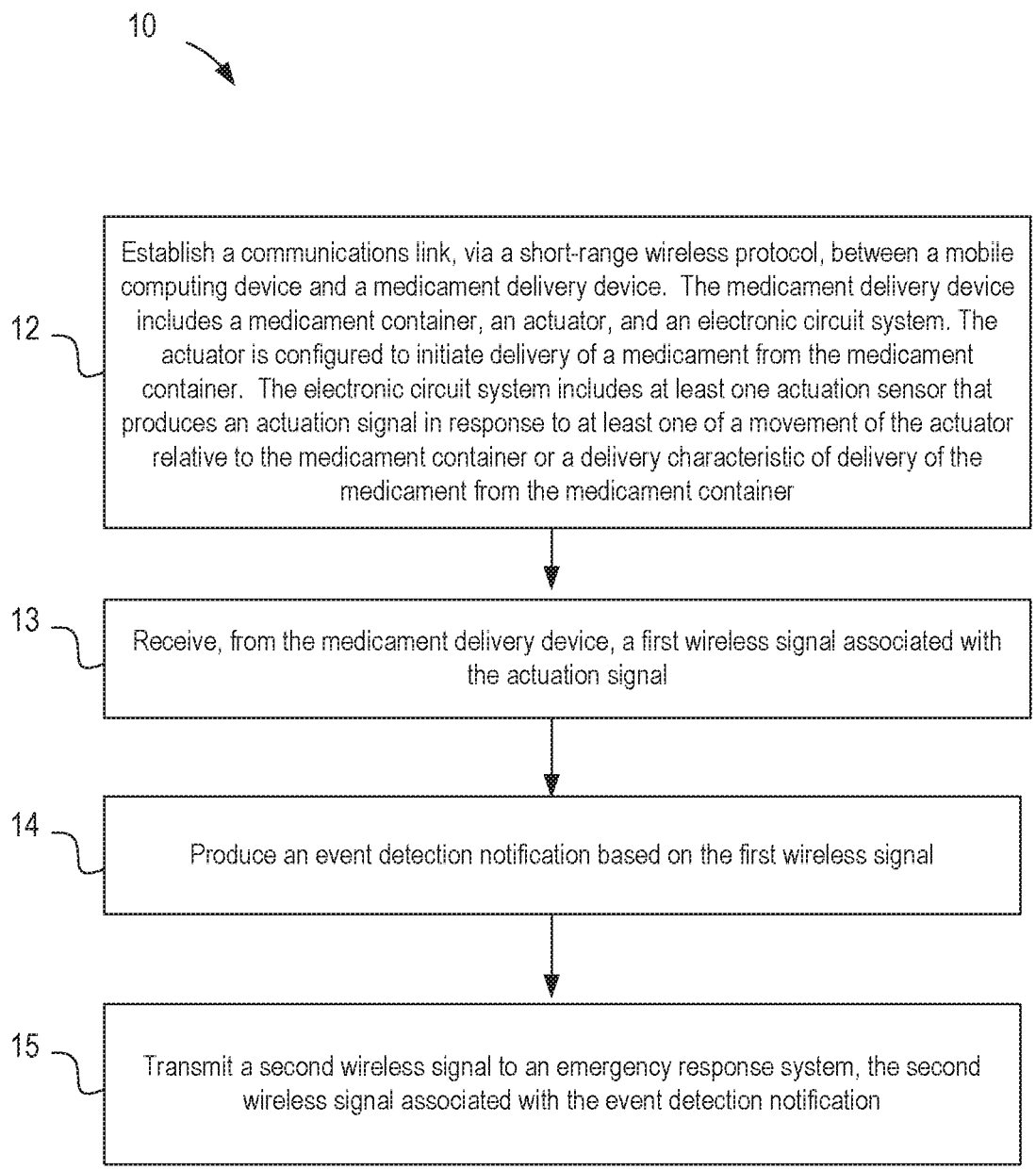
FIG. 45 is a flow chart of a method of transmitting an emergency signal according to an embodiment.

In other embodiments, a signal (including a call, location information, or the like) can be wirelessly transmitted by any application executed by a processor of the mobile computing device—either the application that is a part of the connected health system 7800 or a second, different application. FIG. 45 is a flow chart of a method 10 of transmitting an emergency signal according to an embodiment. The method 10 includes establishing a communications link, via a short-range wireless protocol, between a mobile computing device and a medicament delivery device, at 12. The short-range wireless protocol can be any of the protocols described herein, including the Bluetooth® wireless protocol. The medicament delivery device can be any of the devices described herein, such as an auto-injector (e.g., the auto-injectors 4000 and 5000), a pen injector, a medication pump, a body-worn drug delivery device, a prefilled syringe, a nasal delivery device or an inhaler. The medicament delivery device includes a medicament container, an actuator, and an electronic circuit system. The actuator (e.g., the actuator 4300 or 5300) is configured to initiate delivery of a medicament from the medicament container. The electronic circuit system can be, for example, the electronic circuit system

5900 described herein. The electronic circuit system includes at least one actuation sensor. The actuation sensor can be, for example, the switch 4973 or 5973 and is configured to produce an actuation signal in response to movement of the actuator relative to the medicament container. The actuation sensor can also be, for example, an accelerometer configured to produce a second actuation signal associated with a delivery characteristic of delivery of the medicament from the medicament container.

The method further includes receiving from the medicament delivery device a first wireless signal associated with the first actuation signal, at 13. An event detection notification based on the first wireless signal is then produced, at 14. The event detection notification can be produced by the notification module 7817 and can include any suitable notification, such as the GUI elements, sounds, or the like.

A second wireless signal is transmitted to an emergency response system, at 15. The second wireless signal is associated with the event detection notification. The second wireless signal can be, for example, a call to an emergency responder, a text message, an e-mail or any other suitable format. In some embodiments, the second wireless signal includes a location of at least one of the medicament delivery device or the mobile computing device. Moreover, in some embodiments, the method includes automatically sending the second wireless signal (i.e., sending the second wireless signal without additional human interaction of pressing a button, answering a prompt, etc.).

The remote computing devices 7802 can be devices within the connected health system 7800 that are operated by or in possession of an entity other than the user and/or patient. For example, the remote computing devices 7802 can be operated by or in possession of the patient's parents, emergency contacts, a health care provider, or the like. The remote computing devices 7802 can each be a mobile computing entity, such as a smart mobile phone (e.g., an iPhone®, an Android® device, a Windows® phone, a Blackberry® phone, etc.), a tablet computer (e.g., an Apple iPad®, a Samsung Nexus® device, a Microsoft Surface® device, etc.), or a computer (e.g., a laptop, desktop, smart TV, etc.), and/or any other suitable computing entity. Although not shown in FIG. 44, the computing devices 7802 include a processor, a memory, a user interface, and a radio, similar to the structure describe above for the remote computing device 7801. Moreover, the remote computing devices 7802 can include and/or execute any of the application modules described above with reference to the remote computing device 7801. For example, although the remote computing devices 7802 are not shown as being in direct communication (e.g., via a short-range wireless communication protocol) with the medicament delivery devices 7000, in other embodiments, any of the remote computing devices 7802 can be placed in wireless communication with the medicament delivery devices 7000. The remote computing devices 7802 can produce notification and alerts (via any of the application modules described herein) to alert others (non-patient personnel) about the status of the medicament delivery devices 7000. For example, the remote computing device 7802 can be a "parent device" and can present notification produced by a leash module, a compliance module, or the like. In addition, the remote computing device can receive data from a cloud platform and update a dashboard that can be viewed on the remote computing device in 'real-time' in order to capture delivery events and patient information. This is particularly useful for healthcare professionals looking to monitor their patient's compliance with a medicament regimen.

Methods of Determining Compliance and Carrying of a Device

Figure 46:
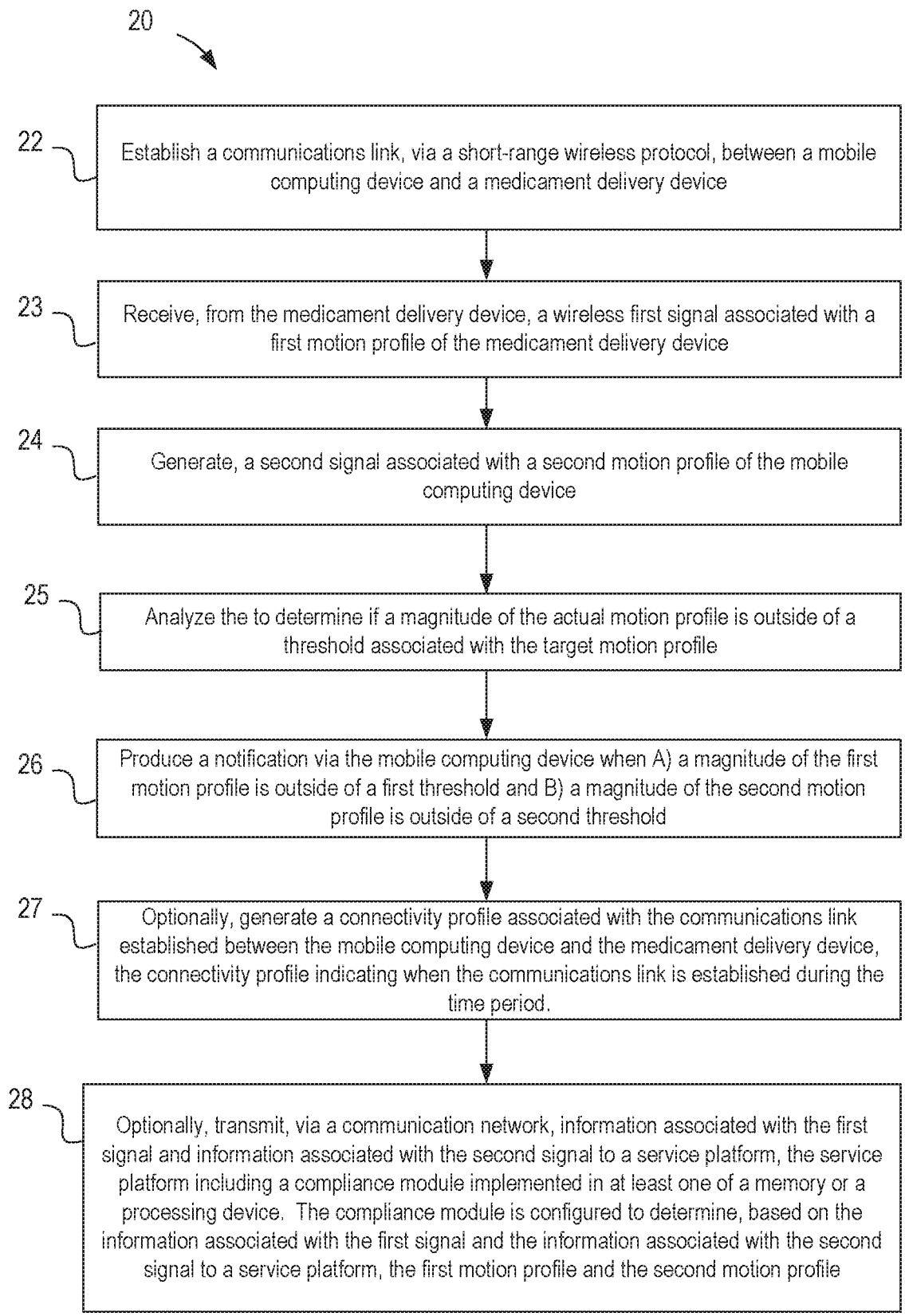
FIG. 46 is a flow chart of a method of determining compliance according to an embodiment.

In some situations, an individual may be advised to carry a medicament delivery device, such as an epinephrine auto-injector, but may rarely use the medicament delivery device. As a result, the user may occasionally forget to carry the medicament delivery device, which can have serious consequences in the event of a medical emergency. Accordingly, in some embodiments, the medicament delivery system can include a compliance tracking or "carry tracking" functionality that determines whether the user carried the medicament delivery device based on information from the medicament delivery device 7000, as well as information from the user's mobile computing device 7801. For example, FIG. 46 is a flow chart of a computer-implemented method 20 of determining whether the device has been carried with the user. The method 20 can be implemented in any of the modules of the medicament delivery device 7000, the mobile computing device 7801 and/or the service platform 7840. Moreover, although described with reference to the delivery system 7800 the compliance methods described herein can be performed by any of the systems described herein.

The method 20 includes establishing a communications link between a computing device and a medicament delivery device, at 22. The communications link can be, for example, a short range wireless link, and the computing device can be a mobile computing device, such as the computing device 7801 described above. In other embodiments, however, the link can be established directly between the medicament delivery device (e.g., the device 7000) and the service platform 7870. Such a link can be established, for example, via a direct-to-network chip capability within the medicament delivery device 7000. By circumventing the need for the computing device 7801 as an intermediate communication node, the device can communicate directly with the service platform 7870.

A first signal associated with a first motion profile of the medicament delivery device is then received from the medicament delivery device, at 23. The first signal can be, for example, a wireless signal associated within a first motion profile of the medicament delivery device. For example, the first signal can be associated with any of a position, a velocity, an acceleration, or an orientation of the medicament delivery device during a time period. In some embodiments, the first signal can be based on (or include) accelerometer information that is stored in the memory of the medicament delivery device. For example, the electronic circuit system 7900 (or the processor 7980) can check the accelerometer every 15 minutes to ascertain if the device has started or stopped moving during that 15-minute period. The memory 7999 of the electronic circuit system 7900 can store a series of such data, which is then transmitted as the first signal. In some embodiments, the memory 7999 can store up to ten movement events. In other embodiments, the memory 7999 can store up to 20, 50, or 100 movement events. In some embodiments, the first motion profile can be associated with a number (or amount) of movement events that occurs with the time period. For example, in some embodiments, the first motion profile can characterize whether the medicament delivery device moved at least a certain number of times (e.g., 5 times) within a tracking time period (e.g., one full day, one work day, or the like).

In some embodiments, the first signal is a raw or filtered signal from the accelerometer (such as the accelerometer described above with reference to the device 5000). In such embodiments, the first motion profile can be characterized or produced by a processor of the mobile computing device or a processor of the service platform 7870. In other embodiments, however, the processor 7980 of the medicament delivery device can manipulate the raw or filtered accelerometer signals to characterize or produce the first motion profile. In such embodiments, the first signal can include the first motion profile. A second signal associated with a second motion profile of a mobile computing device is generated or received, at 24. The mobile computing device can be the mobile computing device 7801 described herein, or any other suitable device that has motion tracking capabilities (e.g., an accelerometer, a global positioning sensor, or the like). In situations where a portion of the compliance method is performed on the system platform 7870, the second signal can be a wireless signal received from the mobile computing device 7801 (and received by the system platform 7870, for example). In other situations where the compliance method is performed at least partially on the mobile computing device 7801, the second signal can be generated internally by the mobile computing device, and the subsequent operations can also be performed on the mobile computing device without the second signal being transmitted. In some embodiments, the second signal can be based on (or include) accelerometer information that is produced by the mobile computing device 7801. In other embodiments, the second signal can be based on (or include) position information based on a GPS of the mobile computing device 7801. For example, the second signal can be associated with any of a position, a velocity, an acceleration, or an orientation of the mobile computing device during a time period.

A notification is then produced when A) a magnitude of the first motion profile is outside of a first threshold and B) a magnitude of the second motion profile is outside of a second threshold, at 25. The notification can be produced by any of the mobile computing device 7801, the medicament delivery device 7000, the computing device 7802, or any other component of the connected health system 7800. By evaluating the motion profile of the medicament delivery device 7000 (which may not include any GPS information) and the motion profile of the mobile computing device 7801, the system can accurately determine whether the device 7000 has been carried during a time period. Importantly, this analysis can be performed without the device being continuously in communication with the mobile computing device 7801 and/or the service platform 7870 and without requiring that the actual position (e.g., location) of the device 7000 be known.

In some embodiments, the determination of a "carry day" (and the production of the notification) can be based, at least in part, on whether and when the medicament delivery device is in communication with the mobile computing device. For example if the second motion profile indicates movement of the mobile computing device during a time period when the communication link between the medicament delivery device and the mobile computing device is not established, then a different notification may be produced than when such movement occurs while the communication link is established and active. For example, in some embodiments, the method 20 can optionally include generating a connectivity profile associated with the communications link established between the mobile computing device and the medicament delivery device, at 26. The connectivity profile indicates when the communications link is established during the time period. The second motion profile includes a distance of the movement event of the mobile computing device when the communications link is established.

In some embodiments, the method 20 can optionally include transmitting, via a communication network, information associated with the first signal and information associated with the second signal to a service platform, at 27. The service platform can be the service platform 7870 described herein or some other "backend" platform. The service platform including a compliance module, implemented in at least one of a memory or a processing device, that is configured to determine, based on the information associated with the first signal and the information associated with the second signal to a service platform, the first motion profile and the second motion profile.

Determining a "carry day" in accordance with the method 10 is variable and is not specific to whether the device has just moved from one location to another. For instance, if a patient does not leave the house all day, they may have still "carried" the device because they have effectively followed the instructions for use of the device by keeping it with them. This non-movement possession can be determined by ongoing or frequent communication between the delivery device 7000 and mobile device 7801 during the day. Moreover, by analyzing whether each of the first motion profile (of the device) and the second motion profile (of the mobile computing device) are above a threshold, the method 10 can accurately determine a "carry day." In some embodiments, the method can include analyzing the first motion profile and the second motion profile against more than one threshold and/or against any suitable decision matrix. For example, Table 1 below provides an example decision matrix that is employed by a compliance module to determine whether the device 7000 has been carried.

TABLE 1

|  | Mobile Device Moved | Mobile Device Did Not Move |
|---|---|---|
| Delivery Device Moved | Carried | Carried |
| Delivery Device Did Not Move | Did Not Carry | Carried |

In some embodiments, the compliance module will determine whether the level of motion (or the motion profile) is above or below a threshold such that it can be determined that the delivery device 7000 and the mobile computing device 7801 moved. Algorithms for determining movement include:

The delivery device 7000 moves at least N1 time(s) in one day at least H hour(s) apart. In some embodiments, N1 is at least 3, at least 4, or at least 5, and H is at least 1 hour, at least 2 hours, or at least 3 hours.

The mobile device 7801 moves a distance of Y yards N2 time(s) and connects with the delivery device 7000 Q at each location. In some embodiments, Y is at least 50 yards, at least 100 yards, at least 200 yards, or at least 500 yards. In some embodiments, N2 is at least 3, at least 4, or at least 5.

The delivery device 7000 does not move all day, the mobile device does not move or stays within a radius of Y yards all day, and the mobile device successfully connects with the delivery device 7000 P time(s). In some embodiments, Y is at least 50 yards, at least 100 yards, at least 200 yards, or at least 500 yards. In some embodiments, P is at least 3, at least 4, or at least 5.

The orientation of the delivery device 7000 changes Z times during the carry period. In some embodiments, Z is at least 3, at least 4, or at least 5.

Although the motion profile of the medicament delivery device 7000 is described as being collected in discrete increments, in other embodiments, the accelerometer data and/or the motion profile data can be collected and/or analyzed continuously.

Methods of Selected and Modifying Electronic Outputs

In some embodiments, the computing device 7801 (or the service platform 7870) can send a signal to the electronic circuit system 7900 to cause the medicament delivery device 7000 to emit an audible output. In some embodiments, sending a signal from the computing device 7801 (or the service platform 7870) can allow the user to select a customized or specific set of electronic outputs to be produced by the medicament delivery device. This can allow a user to tailor the outputs specific to their needs. This can also allow for power conservation—for example, in some embodiments, the service platform 7870 can produce a signal that results in "defeaturing" or suppression of certain electronic outputs. For example, in some embodiments, a user can provide instructions (e.g., in response to a prompt presented via the mobile computing device 7801) to disable certain outputs, thereby improving power consumption.

Figure 47:
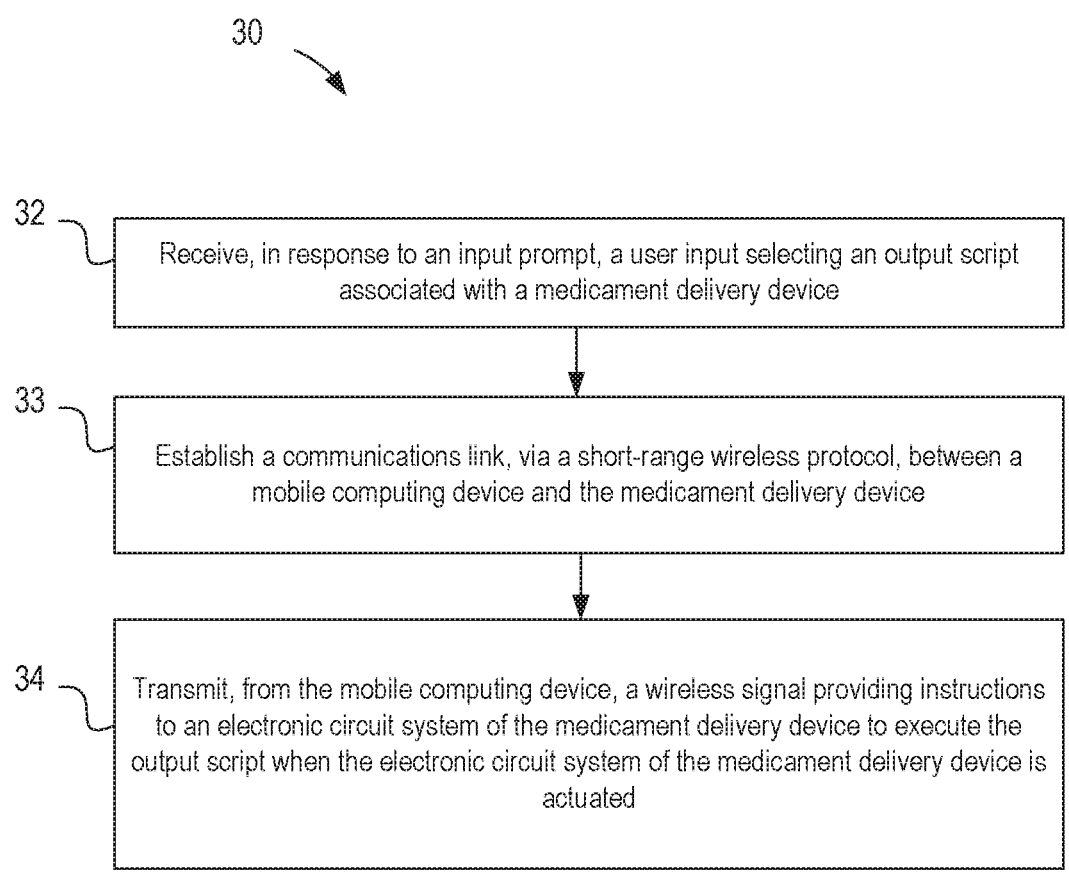
FIG. 47 is a flow chart of a method of selecting an output script according to an embodiment.

Specifically, FIG. 47 is a flow chart of a method 30 of selecting an output script from a set of output scripts to be produced by the electronic circuit system 7900 when the device is used. For a chronic care device where the user is familiar with operation of the device, the user may suppress the instruction scripts and only select a countdown timer for use. Similarly stated, in some embodiments, the power module 7987 or an output module (or any other modules described herein) can modify the default output script in response to a wireless signal received by the electronic circuit system. In other embodiments, the power management module 7987 (or an output module) can receive a signal directly from the service platform 7870 (e.g. and not via the mobile computing device 7801) and can adjust the output script in response to the signal. Although described as modifying an audible output, in other embodiments, the power management module 7987 can modify any of the electronic outputs described herein, such as, for example, the wireless communication signals produced by the radio 7951, any of the visual outputs described herein, a haptic output or the like.

Referring to FIG. 47, the method 30 includes receiving, in response to an input prompt, a user input selecting an output script associated with a medicament delivery device, at 32. A communications link is established between a mobile computing device and the medicament delivery device via a short-range wireless protocol, at 33. The method further includes transmitting, from the mobile computing device, a wireless signal providing instructions to an electronic circuit system of the medicament delivery device to execute the output script when the electronic circuit system of the medicament delivery device is actuated, at 34.

In other embodiments, the electronic configuration of the electronic circuit system 7900 can facilitate methods of updating an instruction script and/or voice prompt stored in the memory 7999 of the electronic circuit system 7900. For example, in some embodiments, the electronic circuit system 7900 can receive signals from the computing device 7801 that include information associated with an instruction script and/or voice prompt of the types described herein. This information can then be written to the memory 7999, thus allowing the voice prompts to be updated using the wireless communications capabilities described herein. These methods avoid the need to have the voice prompts contained in a ROM mask, which can be difficult to update. Moreover, these methods allow for the user to customize their voice prompts (e.g., with a specific user's voice, with customized content or the like).

Although described as facilitating a user-implemented update to a voice prompt, in other embodiments, the electronic circuit system 7900 (and any of the system described herein) can be configured to update the voice prompts based on the user's past history (e.g., via the use module 7982). In this manner, the systems and methods described herein can be used to produce a "smart" or "trainable" device.

Advanced Event Detection and Response

As described herein and in U.S. Pat. No. 10,332,623, entitled "Medicament Delivery Devices with Wireless Connectivity and Event Detection," filed Jan. 16, 2018, which is incorporated herein by reference in its entirety, in some embodiments, any of the use modules or event modules described herein can use multiple different inputs to validate an actual delivery event.

In some embodiments, a use module can receive input from one or more sensors to validate the completion of a medicament delivery event. Such sensors can include any of the sensors described herein. Such sensors can also include a skin sensor (e.g., to verify that the end of the device was placed against the skin. Such sensors can also include an optical sensor to verify the amount and/or conveyance of the medicament from the container. When multiple sensors are used, validation of the injection or drug delivery event can occur due to specific algorithms that confirm multiple outputs corresponding to injection or administration patterns associated with each medicament device. These patterns are unique to each delivery device due to kinematics of injection, various forces from energy storage members, or movement patterns specific to an injection or administration event.

In some embodiments, the medicament delivery device includes a biometric sensor that detects a characteristic of the user along with other sensors that validate a delivery event. In this manner, the medicament delivery device can validate the delivery event and the recipient (or user) of the device. Such biometric characteristics include retinal data, finger print scans, facial recognition, or the like.

In some embodiments, a use module can incorporate data from other applications, such as weather data, etc. to determine whether a dose has been affected or is needed. For example, in addition to determining whether a delivery event has occurred, the medicament delivery device and/or the connected health system can produce a notification regarding potential contraindications associated with external conditions (e.g., weather).

In some embodiments, the connected health systems described herein can determine failure modes of the medicament delivery device and/or the connected health system. In this manner, the connected health system can advance pharmacovigilance efforts. In some embodiments, one or more sensors of the medicament delivery device can be used to determine potential failure modes of the device. Referring to the devices 4000 and 5000, such failure modes can include, for example: an improperly punctured gas cylinder, a punctured gas cylinder, but improper (low or no) resulting pressure, a broken medicament container, a cracked or breached medicament container, a device in which the elastomeric member is compromised or is not included, a device in which gas release valve is improperly overmolded or not included, a device in which the carrier sticks or otherwise moves inconsistently, an injection that is not delivered to tissue (e.g., and injection into air). In other medicament devices the failure modes could include activation spring failure, failure of a gas canister (e.g. inhaler medicament container) to activate, valve malfunction and the like.

In some embodiments, the connected health system 7800 can employ any of the event detection features described herein to update various dashboards, databases and the like. For example, in some embodiments, the medicament delivery device 7000 can produce one or more signals for receipt by the mobile computing device 7801 or the service platform 7870. Based on information received from the medicament delivery device 7000, the service platform 7870 can update information in any of the database systems or dashboards described herein. Similarly stated, the service platform can update the user's electronic health record (EHR) with specific information about the drug delivery event. Such updates can be beneficial in a variety of settings, including emergency care settings, chronic care settings (to ensure that all parties, including doctors, payors, other care givers, etc. are aware of the delivery event), vaccination settings, in the event of pandemics, or the like.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although the cover 4200 and the cover 5200 are shown and described as being substantially solid and covering the status apertures through which a user can view the medicament (e.g., the status apertures 4150, 4151), in other embodiments, any of the covers described herein can include one or more status windows or apertures that can allow a patient to monitor the status and/or contents of a medicament container (e.g., the medicament container 4560). For example, by visually inspecting the status apertures of the cover, a patient can determine, without removing the cover, whether the medicament container contains a medicament, whether the medicament is cloudy or discolored, and/or whether a medicament has been dispensed. In some embodiments, the cover (or any portion of a device housing) can include a label about the status apertures that minimizes the transmission of ultraviolet (UV) radiation therethrough. In this manner, the risk of exposing the medicament to UV radiation can be minimized.

For example, although electronic circuit systems are shown and described above as outputting one or more outputs directed towards a single, immediate user, in some embodiments, a locator device and/or monitoring device can output multiple outputs directed towards multiple different classes of users. For example, in some embodiments, the medicament delivery devices and systems can output a first output to the immediate user (e.g., via a short-range wireless output) and second output to a remotely located emergency response team. In such embodiments, the second output can be, for example, a phone call, SMS, a page, an e-mail or the like. For example, in some embodiments, the second output can be an e-mail to the parents and/or care-givers of a child. Moreover, such a second output can be transmitted either wirelessly or through a wired network. In some embodiments, such outputs can be managed, produced, and/or transmitted by any of the connected health medicament delivery systems shown and described herein, such as the systems 5800 and 6800 described herein.

Although the electronic circuit systems are shown and described above as outputting one or more outputs in response to one or more switches, in other embodiments an electronic circuit system can output an electronic output in response to any number of different inputs. For example, in some embodiments, an electronic circuit system can output an electronic output based on input from the user provided via a keyboard, a touch screen, a microphone or any other suitable input device. In this manner, the electronic outputs can be produced in response to direct feedback from the user. In other embodiments, the electronic outputs can be produced in response to signals produced by one or more sensors, such as the sensors 7970, or any of the sensors described in connection with the electronic circuit system 5900. For example, in some embodiments, any of the electronic outputs can be produced in response to a signal produced by an accelerometer, such as the accelerometer. In other embodiments, the electronic circuit system 5900 (or any of the electronic circuit systems described herein) can include a skin sensor used to detect placement of a portion of the medicament delivery device and send an output to the processor. For example, in some embodiments, a medicament delivery device can be a wearable device having a contact portion that is maintained in contact with the user's skin. In such embodiments, a contact sensor can be used to produce signals associated with the desired placement of the contact portion against the skin. Such skin sensors can include, for example, optical sensors, resistive skin sensors, capacitive touch sensors, or thermal-based skin sensors.

The medicament delivery devices and simulated medicament delivery devices are described herein as being configured to produce one or more wireless signals in accordance with the methods described herein. Although the methods and apparatus are described herein as being configured to modify the communication mode and/or the communication interval associated with such wireless signals in response to a change in the status and/or configuration of a device (e.g., a medicament delivery device or a simulated medicament delivery device), in other embodiments, any of the apparatus and methods described herein can modify any aspect of the wireless signals based on such change in status and/or configuration. For example, in some embodiments a method can include modifying a power level of a wireless signal in response to a change in status and/or configuration of a medicament delivery device or a simulated medicament delivery device. In other embodiments, a method can include modifying the information contained within a wireless signal in response to a change in status and/or configuration of a medicament delivery device or a simulated medicament delivery device. For example, in some embodiments, a wireless signal can include information associated with a signal power level (e.g., TX Power) and/or an identification of a device. Such information can be changed in response to a change in status and/or configuration of a medicament delivery device or a simulated medicament delivery device.

In some embodiments, information included within a signal can include instructions to initiate a natural language user interface associated with (or running on) another device. Thus, any of the apparatus and methods described herein can be configured to send and/or can include the sending of a signal to initiate a natural language user interface associated with a remote computing device. For example, in some embodiments, any of the electronic circuit systems coupled to or associated with any of the medicament delivery devices (or simulated devices), such as the device 4900, or 5900, can be configured to send a wireless signal to initiate a natural language user interface associated with a remote computing device, such as, for example, the computing devices 7801, 7802 described above. In such embodiments, the computing device can be, for example, a smart phone having a natural language user interface, such as, for example, Siri (from Apple) or any other "intelligent personal assistant." The electronic circuit system can be configured to initiate the user interface via the wireless connection by sending a signal. In some embodiments, the signal can be sent in response to a change in the status and/or configuration of the medicament delivery device and/or the simulated medicament delivery device. In this manner, the electronic circuit system can initiate the interface to provide the user with additional resources during a time of activity with the medicament delivery device and/or the simulated medicament delivery device.

In some embodiments, a computing device (e.g., the user's mobile phone, or any other device, such as the computing devices 7801, 7802 described above) can send signals based on and/or produced from a natural language interface that are received by a medicament delivery device, a cover, and/or a simulator of the types shown and described herein. For example, as described above, a connected health medicament delivery system can include a computing device, such as a cell phone that has a natural language interface, and a medicament delivery device, such as an auto-injector, an inhaler, wearable injector, or a patch pump. In such embodiments, a user can provide voice commands to natural language interface of the cell phone. Such commands can include, for example, instructions to administer an additional dose, instructions to call a healthcare professional or the like. In response, the cell phone can send, via a wireless connection of the types shown and described herein, a signal to the medicament delivery device. The device can then execute the instructions. In this manner, the capability of the cell phone can be leveraged to produce a voice-activated medicament delivery device.

Any of the radios, transmitters, receivers, and/or transceivers described herein can be operable to transmit, receive, repeat, and/or otherwise interact with electromagnetic signals. Electromagnetic signals can be of any suitable frequency. For example, the radios, transmitters, receivers, and transceivers can be operable to transmit and/or receive IEEE 802.11 signals, Bluetooth® signals, FM radio signals, AM radio signals, cellular telephone signals, satellite pager signals, RFID signals, GPS signals, and/or any other suitable electromagnetic signal.

Although the computing device 7801 is described above as including a user interface 7820 that can display any of the GUI elements described herein, in other embodiments, the electronic circuit system on any of the medicament delivery devices (e.g. the electronic circuit system 5900) can include a user interface than can display any of the GUI element described herein. For example, in some embodiments, a medicament delivery device (including either the housing of the device or the cover within which the device is contained, such as the cover 5200) can include a touch screen that can display GUI elements and receive input into the electronic circuit system of the medicament delivery device.

Although the medicament delivery devices are shown and described herein as establishing a short-range connection with a remote computing device (e.g., a smart phone) via the Bluetooth® wireless protocol, in other embodiments, any of the devices and methods described herein can employ any suitable short-range communication link, such as near field communication (NFC) or infrared (IR).

Although the medicament delivery devices are shown and described herein as including a radio (e.g., the radio 7951) and/or a communication module (e.g., the communication module 7981) that establish a short-range connection with a remote computing device (e.g., a smart phone), in other embodiments, any of the radios and/or communication modules of the medicament delivery devices described herein can establish any suitable wireless connection with any suitable communication device. For example, in some embodiments, any of the medicament delivery devices described herein can include a radio and/or communication module configured to establish a wireless connection within a cellular network. In this manner, the medicament delivery device can directly access any number of remote devices (e.g., the parent's phone 7802, the service platform 7870, or the like) without requiring a short-range connection with the user's remote device (e.g., the user's phone 7801). In other embodiments, any of the medicament delivery devices described herein can include a radio and/or communication module configured to establish a wireless connection via LTE Direct protocol or any other suitable protocols.

In some embodiments, a medicament delivery device is shown and described as an auto-injector. In other embodiments, the medicament delivery device can be a patch configured to adhere to the patient. The patch can release a medicament, for example, after receiving a signal that medical treatment is needed. The patch can receive the signal from, for example, a monitoring device. In other embodiments, the medicament delivery device can be an injector configured to be carried in a pocket of the patient's garments. The injector can be configured to inject a medicament, for example, after receiving a signal that medical treatment is needed.

In some embodiments, any of the electronic circuit systems and/or connected health medicament delivery systems can be used in conjunction with any suitable medicament delivery device or drug product. For example, in some embodiments, any of the electronic circuit systems and/or connected health medicament delivery systems can be used in conjunction with an inhaler, a tablet delivery system, an on-body delivery system, a nasal delivery system (e.g., an intranasal sprayer), or a nebulizer.

Although in some embodiments the electronic circuit systems are shown and described above as outputting a single output in response to an input (e.g., the removal of a medicament delivery device from a cover, the actuation of a medicament delivery device, etc.), in other embodiments, an electronic circuit system can output a sequence of electronic outputs in response to such an input. In some embodiments, for example, when a medicament delivery device is removed from a container, an electronic circuit system (e.g., the electronic circuit systems 1900, 4900, 5900) can output a predetermined sequence of use instructions over a predetermined time period. For example, upon removing the medicament delivery device, the first instruction can be an audible output indicating the type of medicament delivery device removed. After a predetermined time period, the electronic circuit system can then output a second instruction, which can be a visual output instructing the user in how to diagnose the patient and/or prepare the patient for the medicament. In a similar manner, the electronic circuit system can provide additional outputs to instruct the user in the use of the medicament delivery device. Moreover, in some embodiments, the electronic circuit system can output an output instructing the user in post-use procedures, such as for example, the disposal of the medicament delivery device, instructions for follow-up treatment or the like.

Although some embodiments describe a recorded message output in English, in other embodiments, the electronic circuit system can output recorded speech in any language.

In yet other embodiments, the electronic circuit system can output recorded speech in multiple languages. In yet other embodiments, the user can select the language in which the recorded speech is to be output.

Medicament delivery devices shown and described above can be single-use medical injectors, or any other suitable device for delivering one or more doses of a medicament into a patient's body. For example, in some embodiments, a medicament delivery device can be a pen injector containing multiple doses of a chronic-care medicament, such as, for example, insulin. In such embodiments, an electronic circuit system (of the types shown and described herein) can output instructions associated with not only an initial use of the medicament delivery device, but also associated with repeated uses, dosage monitoring or the like. In other embodiments, a medicament delivery device can include a transdermal medicament delivery device, a wearable injector or pump that dispenses drug over several hours or days, an inhaler or a nasal medicament delivery device.

For example, in some embodiments, a chronic-care medicament delivery device can include one or more sensors (e.g., the sensors 7970) that detect a status or use of the device, and can work in conjunction with a use module (e.g., the use module 7982, the use module 7812 or any of the use or "event detection" modules described herein) to produce outputs notifying a user of when certain medicament delivery events are due in accordance with a prescribed regimen. For example, in some embodiments, certain therapeutic agents (e.g., medicaments to treat diabetes, rheumatoid arthritis (RA), multiple sclerosis (MS), and/or Crohn's disease) are administered at regular intervals. Such intervals can be, for example, twice daily, once daily, once weekly, or the like. In such embodiments, a use (or event detection) module can detect an actual delivery, including a date and/or time stamp of the delivery. A notification module (e.g., the notification module 7817) or any of the other modules described herein can calculate a "next delivery" date (or time) and produce a reminder notification. The reminder notification can be similar to any of the GUI elements described herein. For example, in some embodiments, the next delivery date can be calculated based on the date and time stamp of the most recent detected usage of the medicament delivery device. The use module can then maintain a count of how many doses have been administered and determine, based on the detected use and the stored regimen, the next delivery date.

In other embodiments, a delivery interval can be irregular and/or based on information or data that is independent of a time interval. Such information can include, for example, physiological data of the patient (e.g., blood glucose levels or the like). In such embodiments, a use module (or any other module described herein) can receive information associated with the actual use (or delivery) of the device, the date and/or time stamp, and the additional information, and calculate a "next delivery" date (or time). For example, in some embodiments, a patient may log test data (e.g., blood glucose measurements) via a second application (i.e., an application executed by the processor 7810 or any other processor described herein, the application being separate from the connected health system application). In such embodiments, an application interface module (e.g., the application interface module 7818) can receive the information or test data from the second application. The information received can then be used to calculate the next delivery date or time. In this manner, the application interface module can automatically retrieve information (e.g., the patient's test data) used to accurately calculate the next delivery event.

In some embodiments, a chronic-care medicament delivery device can include a medicament container containing multiple doses of a medicament, and a dose adjustment mechanism with which the user can adjust the dosage amount to be delivered. Such dose adjustment mechanisms can include, for example, a dial adjustment mechanism that limits a stroke length of an injector plunger. In such embodiments, a notification module (e.g., the notification module 7817) or any of the other modules described herein can produce a notification reminding the user of the next delivery date, and also reminding the user of the desired dosage setting. The notification can be similar to any of the GUI elements described herein. In some embodiments, the notification can include one or more instructions for operating the dose adjustment mechanism. For example, the notification can include a video presentation that is displayed via a user interface (e.g., the user interface 7820) that guides a user step-by-step through the dose adjustment process. In other embodiments, the chronic-care medicament delivery device can include a sensor (e.g., included among the sensors 7970 described above) that senses the position of the dose adjustment mechanism, a position of the injector plunger, and/or a remaining stroke length of the injector plunger. In such embodiments, the notification can include information based on the actual position of the dose adjustment mechanism. For example, in some embodiments, a notification can indicate the current dosage setting based on feedback from the sensor (e.g., "The current setting is 0.5 mL"). In some embodiments, a duration for an audible countdown timer as described herein can be selected according to the current dosage setting based on the feedback from the sensor. Once the user has adjusted the dose adjustment mechanism to a desired dosage position, a corresponding countdown timer output script can be selected and executed to instruct the user on the duration of the injection procedure. For example, if it takes 10 seconds to complete an injection of 1.0 mL of medicament and the dosage adjustment mechanism has been adjusted to dispense 1.0 mL of medicament, a 10-second countdown timer output script can be selected and executed. By way of another example, if it takes 5 seconds to complete an injection of 0.5 mL of medicament and the dosage adjustment mechanism has been adjusted by the user to dispense 0.5 mL of medicament, a 5-second countdown timer output script can be selected and executed.

In some embodiments, the output script is selected from a plurality of output scripts, and each of the plurality of output scripts corresponds to a different position of the dose adjustment mechanism (e.g., a first dosage position and a second dosage position). The plurality of output scripts can include at least a first output script with a first countdown timer and a second output script with a second countdown timer. A time duration of the first countdown timer is different from a time duration of the second countdown timer.

In other embodiments, any of the medicament delivery devices described herein can include an actuator that limits movement of the dose adjustment mechanism. For example, in some embodiments, a chronic-care medicament delivery device can include an electronic actuator that, when actuated, can limit movement (i.e., can "lock out") the dose adjustment feature. In such embodiments, a dose control module (or any of the application modules described herein) can receive information associated with the prescribed dose and can limit movement of the dose adjustment mechanism in response to such information. In this manner, the medicament delivery device and/or the connected health system can "lock out" or otherwise prevent the user from setting the incorrect dose.

In yet other embodiments, any of the medicament delivery devices described herein can include a disarming mechanism that prevents the device from administering the medicament. For example, in some embodiments, a disarming device can reversibly prevent an activation mechanism from producing the force to deliver a dose of the medicament. This can be useful, for example, in a chronic-care application to prevent a dose from being administered before the desired delivery date or time. In such embodiments, a dose control module (or any of the application modules described herein) can receive information associated with the prescribed dose and can prevent actuation of the device in response to such information. In some embodiments, the disarming device can be a mechanism that prevents removal of a cover (e.g., the cover 4200 or the cover 5200), removal of a safety guard (e.g., the safety lock 4700 or the safety lock 5700) and/or movement of the actuator (e.g., the base 4300 or the base 5300).

In other embodiments, the disarming device can irreversibly and/or permanently prevent delivery of the medicament. For example, in some embodiments, the medicament delivery device can be irreversibly and/or permanently disabled in response to the temperature sensor indicating that the medicament has been stored above a predetermined temperature for a certain amount of time. In other embodiments, the medicament delivery device can be irreversibly and/or permanently disabled in response to a timer indicating that the medicament is expired or has been mixed for longer than a predetermined period of time. The disarming device can be any of the disarming devices shown and described in U.S. Pat. No. 8,361,026 entitled "Apparatus and Methods for Self-Administration of Vaccines and Other Medicaments," filed Nov. 19, 2009, which is incorporated herein by reference in its entirety.

Although various embodiments have been described as having particular features and/or combinations of components, other embodiments are possible having a combination of any features and/or components from any of embodiments where appropriate. For example, although some embodiments are described as having a processor, a radio, a sensor, etc. disposed on a particular portion of a device (e.g., on the electronics housing 4170), in other embodiments, any of the electronic circuit systems can be disposed on any suitable portion of a delivery device or simulated delivery. For example, in some embodiments, a removable outer cover of a medicament delivery device (such as the covers 4200 or 5200) or simulated medicament delivery device can include a processor and/or radio. Similarly, in some embodiments a kit can have a processor, audible output, etc. Any devices, structures, and/or modules associated with a medicament delivery device, therefore, can be associated with any suitable kit, adapter, cover, and/or simulated medicament delivery device.

The medicament delivery devices described herein, such as the medical injector 1000, and any others described herein, can be any suitable medicament delivery device. For example, a medicament delivery device according to an embodiment can include a pen injector, an auto-injector, a wearable injector or pump that dispenses drug over several hours or days, other body-worn drug delivery devices, an inhaler or a transdermal delivery device. Where medicament delivery devices are described, it should be understood that alternative embodiments including a simulated medicament delivery device are possible, for example, the simulated medicament delivery devices shown and described in U.S. Pat. No. 9,022,980, entitled "Medical Injector Simulation Device" filed Feb. 27, 2007, the disclosure of which is incorporated herein by reference in its entirety. A simulated medicament delivery device may be suitable to train a user in the operation of a medicament device.

The simulated medicament delivery device can simulate the actual medicament delivery device in any number of ways. For example, in some embodiments, the simulated medicament delivery device can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device can include components that correspond to the components of the actual medicament delivery device. In this manner, the simulated medicament delivery device can simulate the look, feel and sounds of the actual medicament delivery device. For example, in some embodiments, the simulated medicament delivery device can include external components (e.g., a housing, a needle guard, a sterile cover, a safety lock or the like) that correspond to external components of the actual medicament delivery device. In some embodiments, the simulated medicament delivery device can include internal components (e.g., an actuation mechanism, a compressed gas source, a medicament container or the like) that correspond to internal components of the actual medicament delivery device.

In some embodiments, however, the simulated medicament delivery device can be devoid of a medicament and/or those components that cause the medicament to be delivered (e.g., a needle, a nozzle or the like). In this manner, the simulated medicament delivery device can be used to train a user in the use of the actual medicament delivery device without exposing the user to a needle and/or a medicament. Moreover, the simulated medicament delivery device can have features to identify it as a training device to prevent a user from mistakenly believing that the simulated medicament delivery device can be used to deliver a medicament. For example, in some embodiments, the simulated medicament delivery device can be of a different color than a corresponding actual medicament delivery device. Similarly, in some embodiments, the simulated medicament delivery device can include a label clearly identifying it as a training device.

In some embodiments, the medicament delivery devices and/or medicament containers shown herein can include any suitable medicament, such as a vaccine. Such vaccines can include, for example, an influenza A vaccine, an influenza B vaccine, an influenza A (H1N1) vaccine, a hepatitis A vaccine, a hepatitis B vaccine, a *haemophilus* influenza Type B (HiB) vaccine, a measles vaccine, a mumps vaccine, a rubella vaccine, a polio vaccine, a human papilloma virus (HPV) vaccine, a tetanus vaccine, a diphtheria vaccine, a pertussis vaccine, a bubonic plague vaccine, a yellow fever vaccine, a cholera vaccine, a malaria vaccine, a cancer vaccine, a smallpox vaccine, a pneumococcal vaccine, a rotavirus vaccine, a varicella vaccine, a meningococcus vaccine and/or any combination thereof (e.g. tetanus, diphtheria and pertussis vaccine). In other embodiments, the medicament delivery devices and/or medicament containers shown herein can include epinephrine. In other embodiments, the medicament contained within any of the medicament delivery devices and/or medicament containers shown herein can be naloxone, including any of the naloxone formulations described in U.S. Pat. No. 8,627,816, entitled "Medicament Delivery Device for Administration of Opioid Antagonists Including Formulation for Naloxone," filed on Feb. 28, 2011.

In other embodiments, the medicament contained within any of the medicament delivery devices and/or medicament containers shown herein can include insulin, glucagon, human growth hormone (HGH), erythropoiesis-stimulating agents, adalimumab, risankizumab, sarilumab, upadacitinib, depatuxizumab mafodotin, elotuzumab, ibrutinib, mivebresib, navitoclax, rovalpituzumab tesirine, telisotuzumab vedotin, veliparib, venetoclax, levodopa, carbidopa, elezanumab, other monoclonal Antibodies (mAbs'), Interferon and other chronic therapies, or the like. Some such formulations can be produced using a general lyophilization process and can include any suitable solids (bulking agents or the like, as described herein). For example, some glucagon formulations can be in a solid form and can include glucagon (of recombinant or synthetic origin) using bulking agents, stabilizers, buffers, acidifying agents or other excipients comprising of, but not limited to, one or more of the following combinations: lactose, hydrochloric acid; glucose, histidine, hydrochloric acid; trehalose, mannitol, citrate; trehalose, mannitol, hydrochloric acid; trehalose, glycine, hydrochloric acid; Mannitol, ascorbic acid; and Glycine, hydrochloric acid.

In other embodiments, any of the medicament delivery devices and/or medicament containers described herein can be filled with and/or used to inject medicament formulations, including lyophilized biologics and/or biopharmaceuticals, such as, for example, canakinumab, certolizumab, golimumab, and/or interleukins, for the treatment of crypyrin associated periodic syndromes, hereditary angioedema, and other auto-immune diseases. In yet other embodiments, any of the medicament delivery devices and/or medicament containers described herein can be filled with and/or used to inject intranasal medicaments including small molecules such as epinephrine, naloxone, diazepam, midazolam, lorazepam or biologics, such as glucagon or human growth hormone, formulated for use in an auto injector, for the treatment of musculoskeletal diseases, growth disorders, diabetes or other disorders. Thus, although the medicament delivery devices shown herein are primarily injectors, in other embodiments, a medicament delivery device need not be a medical injector, but rather, can be an inhaler, a wearable pump, an intranasal delivery device or the like.

In other embodiments, any of the medicament delivery devices and/or medicament containers described herein can be filled with and/or used to inject an anti-thrombolytic, such as LMWH, ULMWH, Xa Inhibitors, biotinylated idraparinux, etc., for either the acute management and/or surgical prophylaxis of deep vein thrombosis and/or pulmonary embolism or for the management of other conditions which may require anticoagulation to prevent thromboembolism, such as its use in cardiovascular diseases including atrial fibrillation and ischemic stroke. In another example, in some embodiments an injector according to an embodiment can be filled with and/or used to inject formulations for the treatment of asthma and/or chronic obstructive pulmonary disease.

In other embodiments, any of the medicament delivery devices and/or medicament containers described herein can be filled with and/or used to inject recombinant hyaluronidase.

In other embodiments, any of the medicament delivery devices and/or medicament containers described herein can be filled with and/or used to inject depot medroxyprogesterone acetate for the treatment of infertility.

In other embodiments, any of the injectors described herein can be filled with and/or used to inject Benzodiazepines such as Midazolam, Anticoagulants, Hematopoietic agents, Adrenocortical steroids, Antidiabetic agents, Sex hormones, Somatostatin Analogs, Monoclonal Antibodies, Agents for Migraine, Antianxiety Agents, Antiemetic/Antivertigo Agents, Antipsychotic Agents, General Anesthetics, NSAIDs, Opioid Agonist-Antagonist, Opioid Analgesics, Skeletal Muscle Relaxants. Aminoglycosides, Antiprotozoals, Antiretroviral Agents, Antituberculosis Agents, Bacitracin, Cephalosporin and Related Antibiotics, Colistimethate sodium, Lincosamides, Monobactams, Penicillins, Polymyxin B Sulfate, Antirheumatologic Agents, Antimetabolites, Immune Globulins, Immulogic Agents, Monoclonal antibodies, Antimetabolites, Hematopoietic, and/or Hemin, and agents that block proprotein convertase subtilisin/kexin type 9 (PCSK9).

In other embodiments, any of the medicament delivery devices and/or medicament containers described herein can be filled with and/or used to inject environmental, food, and household allergen formulations for the treatment of allergic disease, specifically for use in immunotherapy.

Any of the devices and/or medicament containers shown and described herein can contain and/or deliver a wide array of large or macromolecular injectables that include carbohydrate-derived formulations, lipids, nucleic acids, proteins/peptides (e.g. monoclonal antibodies) and other biotechnologically-derived medicaments. For example, anti-tumor necrosis factor agents such as infliximab, etanercept, adalimumab, golimumab, natalizumab, vedolizumab, and certolizumab can be administered using the described auto-injector heroin, Other macromolecular injectable medications that can be administered using the device and/or medicament containers shown and described herein include viscous medicaments that target pro-inflammatory cytokines (e.g. IL-1, IL-2, IL-4, IL-5, IL-6, IL-12, IL-13, IL-23, IL-17, IL-21 and associated receptors) including dupilumab, sarilumab, mepolizumab, benralizumab, reslizumab, lebrikizumab, ustekinumab, anrunkinzumab, bertilimumab, and tralokinumab. Large anti-adhesion molecules to treat a variety of diseases may be administered using the device and/or medicament containers shown and described herein including etrolizumab and vatelizumab. Still other large and viscous monoclonal antibodies that may be administered using the device and/or medicament containers shown and described herein include tezepelumab, anifrolumab, omalizumab, and proprotein convertase subtilisin kexin type 9 (PCSK9) inhibitors including alirocumab and evolocumab.

In still other embodiments, the medicament contained within any of the medicament delivery devices and/or medicament containers shown herein can be a placebo substance (i.e., a substance with no active ingredients), such as water.

The medicament containers and/or medicament delivery devices disclosed herein can contain any suitable amount of any medicament. For example, in some embodiments, a medicament delivery device as shown herein can be a single-dose device containing an amount medicament to be delivered of approximately 0.4 mg, 0.8 mg, 1 mg, 1.6 mg or 2 mg. For example, in some embodiments, a connected health medicament delivery system (such as the systems 5800, 6800) can include an epinephrine auto-injector having a dosage suitable for the patient. Such epinephrine auto-injectors can include any of the injectors shown and described in U.S. application Ser. No. 15/850,157, entitled "Medicament Delivery Device and Methods for Delivering Drugs to Infants and Children," and filed on Dec. 23, 2016, which is incorporated herein by reference in its entirety. For example, in some embodiments, any of the medicament delivery devices, such as the device 5000 shown with reference to the system 5800, can be an "adult-dose" drug product configured to deliver 0.3 mL epinephrine. In other embodiments, any of the medicament delivery devices, such as the device 5000 shown with reference to the system 5800, can be a "pediatric-dose" drug product configured to deliver 0.15 mL epinephrine. In yet other embodiments, any of the medicament delivery devices, such as the device 5000 shown with reference to the system 5800, can be a "infant-dose" drug product configured to deliver 0.1 mL epinephrine. Although the phrases "adult-dose," "pediatric-dose," and "infant-dose" are used herein, it is understood that such devices and methods are applicable to any patient within the prescribed weight ranges, even if the patient may not be considered an "adult," a "pediatric patient," or an "infant" by some definitions. For example, the "infant-dose" methods, drug products, and devices described herein are applicable to a child weighing 14 kg, even if that child is considered a toddler or pediatric patient (i.e., is not considered an "infant").

As described above, the fill volume can be such that the ratio of the delivery volume to the fill volume is any suitable value (e.g., 0.4, 0.6 or the like). In some embodiments, an electronic circuit system can include a "configuration switch" (similar to any of the switches shown and described above) that, when actuated during the assembly of the delivery device, can select an electronic output corresponding to the dose contained within the medicament container. In addition, in the case of multiple-dose delivery, the user can activate, via physical movement, voice command or the like, a switch located on the medicament delivery device in order to select the specific dose required.

Although the battery assembly 5960 is shown and described as being coupled to the electronic circuit system of the medicament delivery device 5900, in other embodiments, the battery assembly 5960 can be coupled to any electronic device. For example, the battery assembly 5960 can be coupled to any medical device (e.g., diagnostic device, surgical device, etc.) or even non-medical devices.

What is claimed is:

1. A battery assembly, comprising:
   a battery housing having an outer surface and a first connector, the first connector defining a connector volume and a keyway, the keyway configured to be matingly coupled to a second connector of a battery wire;
   a battery contained within the battery housing, the battery having a positive terminal and a negative terminal;
   a first clip coupled about the battery housing and the battery, the first clip having a first contact portion, a second contact portion, and a first terminal, the first contact portion engaged with the outer surface of the battery housing, the second contact portion engaged with one of the positive terminal or the negative terminal of the battery, the first terminal being configured to move within the connector volume; and
   a second clip having a third contact portion and a second terminal, the third contact portion engaged with the other of the positive terminal or the negative terminal of the battery, the second terminal within the connector volume,
   wherein movement of the first terminal within the connector volume allows the first terminal and the second terminal to align when the second connector is coupled to the first connector; and
   wherein the battery assembly is configured to be coupled to any one of an auto-injector, a pen-injector, a medication pump, a prefilled syringe, a nasal delivery device, an inhaler, or a simulated medicament delivery device.

2. The battery assembly of claim 1, wherein:
   the second contact portion is engaged with the positive terminal of the battery; and
   the first contact portion is electrically isolated from the negative terminal of the battery by the battery housing.

3. The battery assembly of claim 1, wherein:
   the second terminal is maintained at a fixed position within the connector volume.

4. The battery assembly of claim 1, wherein the first clip is deformed to produce an interference fit when the first clip is coupled about the battery housing and the battery.

5. The battery assembly of claim 1, wherein the first contact portion is opposite from the second contact portion, the outer surface of the battery housing and the battery being between the first contact portion and the second contact portion.

6. The battery assembly of claim 5, wherein the first clip is u-shaped.

7. The battery assembly of claim 1, wherein the first connector defines a terminal opening through which a portion of the first clip is disposed.

8. The battery assembly of claim 1, wherein the battery includes a plurality of separate batteries including a first battery and a second battery.

9. The battery assembly of claim 1, wherein the battery is a first battery, the battery assembly further comprising:
   a second battery each contained within the battery housing, the second battery having a positive terminal and a negative terminal, the second battery stacked against the first battery such that the positive terminal of the second battery is in contact with the negative terminal of the first battery;
   the second contact portion engaged with the positive terminal of the first battery; and
   the third contact portion engaged with the negative terminal of the second battery.

10. The battery assembly of claim 1, wherein the battery assembly is configured to be coupled to at least one of a printed circuit board or an electronics housing of an electronic circuit system.

* * * * *